United States Patent
Francischelli et al.

(10) Patent No.: US 7,963,963 B2
(45) Date of Patent: Jun. 21, 2011

(54) ELECTROSURGICAL HEMOSTAT

(75) Inventors: David E. Francischelli, Anoka, MN (US); Roderick E. Briscoe, Rogers, MN (US); Paul T. Rothstein, Elk River, MN (US); David Jin Sung Kim, Maple Grove, MN (US); James R. Keogh, Maplewood, MN (US); Tom P. Daigle, Corcoran, MN (US); Adam A. Podbeliski, St. Paul, MN (US); Stephen J. Roddy, Maple Grove, MN (US); Steve Christian, New Brighton, MN (US); Brian Ross, Maple Grove, MN (US); James Skarda, Lake Elmo, MN (US); Scott E. Jahns, Hudson, WI (US); Alison Lutterman, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1213 days.

(21) Appl. No.: 11/040,663

(22) Filed: Jan. 21, 2005

(65) Prior Publication Data

US 2006/0041254 A1   Feb. 23, 2006

Related U.S. Application Data

(63) Continuation-in-part of application No. 10/621,893, filed on Jul. 17, 2003, now Pat. No. 7,083,620.

(60) Provisional application No. 60/422,330, filed on Oct. 30, 2002.

(51) Int. Cl.
*A61B 18/14* (2006.01)

(52) U.S. Cl. .............................. 606/51; 606/52; 606/205

(58) Field of Classification Search .................... 606/45, 606/46, 51, 52, 205–208
See application file for complete search history.

(56) References Cited

U.S. PATENT DOCUMENTS

| | | | |
|---|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner* — Michael Peffley

(57) ABSTRACT

A hemostat-type device for ablative treatment of tissue, particularly for treatment of atrial fibrillation, is constructed with features that provide easy and effective treatment. The device may include a swiveling head assembly that allows the jaws to be adjusted in pitch and/or roll. The device may include a malleable or articulating handle shaft, as well as, malleable or curved rigid jaws that can permit curved lesion shapes. A locking detent can secure the jaws in a closed position during the procedure. The device may include one or more remote actuators making the hemostat-type device useful for minimally invasive procedures.

42 Claims, 46 Drawing Sheets

U.S. PATENT DOCUMENTS

| | | |
|---|---|---|
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,514,157 A * | 5/1996 | Nicholas et al. ............... 606/206 |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |

| | | | |
|---|---|---|---|
| 5,735,280 A | 4/1998 | Sherman et al. | |
| 5,735,290 A | 4/1998 | Sterman et al. | |
| 5,755,760 A | 5/1998 | Maguire et al. | |
| 5,769,841 A * | 6/1998 | Odell et al. ................. 606/1 | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,802 A | 9/1998 | Panescu et al. | |
| 5,827,216 A | 10/1998 | Igo et al. | |
| 5,827,323 A * | 10/1998 | Klieman et al. ............ 606/205 | |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,871,523 A | 2/1999 | Fleischman et al. | |
| 5,871,525 A | 2/1999 | Edwards et al. | |
| 5,873,845 A | 2/1999 | Cline et al. | |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,893,848 A | 4/1999 | Negus et al. | |
| 5,895,417 A | 4/1999 | Pomeranz et al. | |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,916,213 A | 6/1999 | Haissaguerre et al. | |
| 5,916,214 A | 6/1999 | Cosio et al. | |
| 5,921,924 A | 7/1999 | Avitall | |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,954,661 A | 9/1999 | Greenspon et al. | |
| 5,971,980 A | 10/1999 | Sherman | |
| 5,971,983 A | 10/1999 | Lesh | |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,042,556 A | 3/2000 | Beach et al. | |
| 6,063,081 A | 5/2000 | Mulier | |
| 6,071,279 A | 6/2000 | Whayne et al. | |
| 6,088,894 A | 7/2000 | Oakley | |
| 6,096,037 A | 8/2000 | Mulier | |
| 6,113,592 A | 9/2000 | Taylor | |
| 6,117,101 A | 9/2000 | Diederich et al. | |
| 6,120,496 A | 9/2000 | Whayne et al. | |
| 6,132,441 A * | 10/2000 | Grace ......................... 606/147 | |
| 6,139,563 A * | 10/2000 | Cosgrove et al. ............ 606/205 | |
| 6,142,993 A | 11/2000 | Whayne et al. | |
| 6,142,994 A | 11/2000 | Swanson et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,270,471 B1 | 8/2001 | Hechel et al. | |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,312,435 B1 * | 11/2001 | Wallace et al. ............... 606/130 | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,736 B1 | 12/2001 | Mulier | |
| 6,332,881 B1 | 12/2001 | Carner et al. | |
| 6,358,248 B1 | 3/2002 | Mulier | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,440,130 B1 * | 8/2002 | Mulier et al. .................. 606/49 | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,956 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,484,727 B1 | 11/2002 | Vaska et al. | |
| 6,488,680 B1 | 12/2002 | Francischelli | |
| 6,502,575 B1 | 1/2003 | Jacobs et al. | |
| 6,514,250 B1 | 2/2003 | Jahns | |
| 6,527,767 B2 | 3/2003 | Wang et al. | |
| 6,537,248 B2 | 3/2003 | Mulier | |
| 6,537,272 B2 | 3/2003 | Hoey | |
| 6,558,382 B2 | 5/2003 | Jahns | |
| 6,584,360 B2 | 6/2003 | Francischelli | |
| 6,585,732 B2 | 7/2003 | Mulier | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,645,199 B1 | 11/2003 | Jenkins et al. | |
| 6,648,883 B2 | 11/2003 | Francischelli | |
| 6,656,175 B2 | 12/2003 | Francischelli | |
| 6,663,627 B2 | 12/2003 | Francischelli | |
| 6,685,698 B2 * | 2/2004 | Morley et al. ..................... 606/1 | |
| 6,692,450 B1 | 2/2004 | Coleman | |
| 6,692,491 B1 * | 2/2004 | Phan ............................. 606/41 | |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,773,433 B2 | 8/2004 | Stewart et al. | |
| 6,776,780 B2 | 8/2004 | Mulier | |
| 6,807,968 B2 | 10/2004 | Francischelli | |
| 6,827,715 B2 | 12/2004 | Francischelli | |
| 6,849,073 B2 | 2/2005 | Hoey | |
| 6,858,028 B2 | 2/2005 | Mulier | |
| 6,887,238 B2 | 5/2005 | Jahns | |
| 6,899,711 B2 | 5/2005 | Stewart et al. | |

| | | |
|---|---|---|
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0114850 A1* | 6/2003 | McClurken et al. ............ 606/50 |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): 536-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.
Gallagher et al., "Surgical Treatment of Arrhythmias," The American Journal of Cardiology 61:27A-44A, 1988.
Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery , vol. 1, No. 1 (Jul. 1989) pp. 67-73.
McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I-675,#3946.
Sie et al., "Radiofrequency Ablation of Atrial Fibrillation in Patients Undergoing Valve Surgery," Circulation (Nov. 1997) 84:I450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996;94(Supp 1):I-493, #2889.
Cox et al., "An 8 ½ Year Clinical Experience with Surgery for Atrial Fibrillation," Annals of Surgery, 1996;224(3):267-275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.
Cox, "Anatomic-Electrophysiologic Basis for the Surgical Treatment of Refractory Ischemic Ventricular Tachycardia," Annals of Surgery, Aug. 1983; 198:2;119-129.
Williams, et al., "Left atrial isolation," J Thorac Cardiovasc Surg; 1980; 80: 373-380.
Scheinman, "Catheter-based Techniques for Cure of Cardiac Arrhythmias," Advances in Cardiovascular Medicine, 1996, ISSN 1075-5527, pp. 93-100.
Sueda et al., "Efficacy of a Simple Left Atrial Procedure for Chronic Atrial Fibrillation in Mitral Valve Operations," Ann Thorac Surg, 1997;63:1070-1075.

* cited by examiner

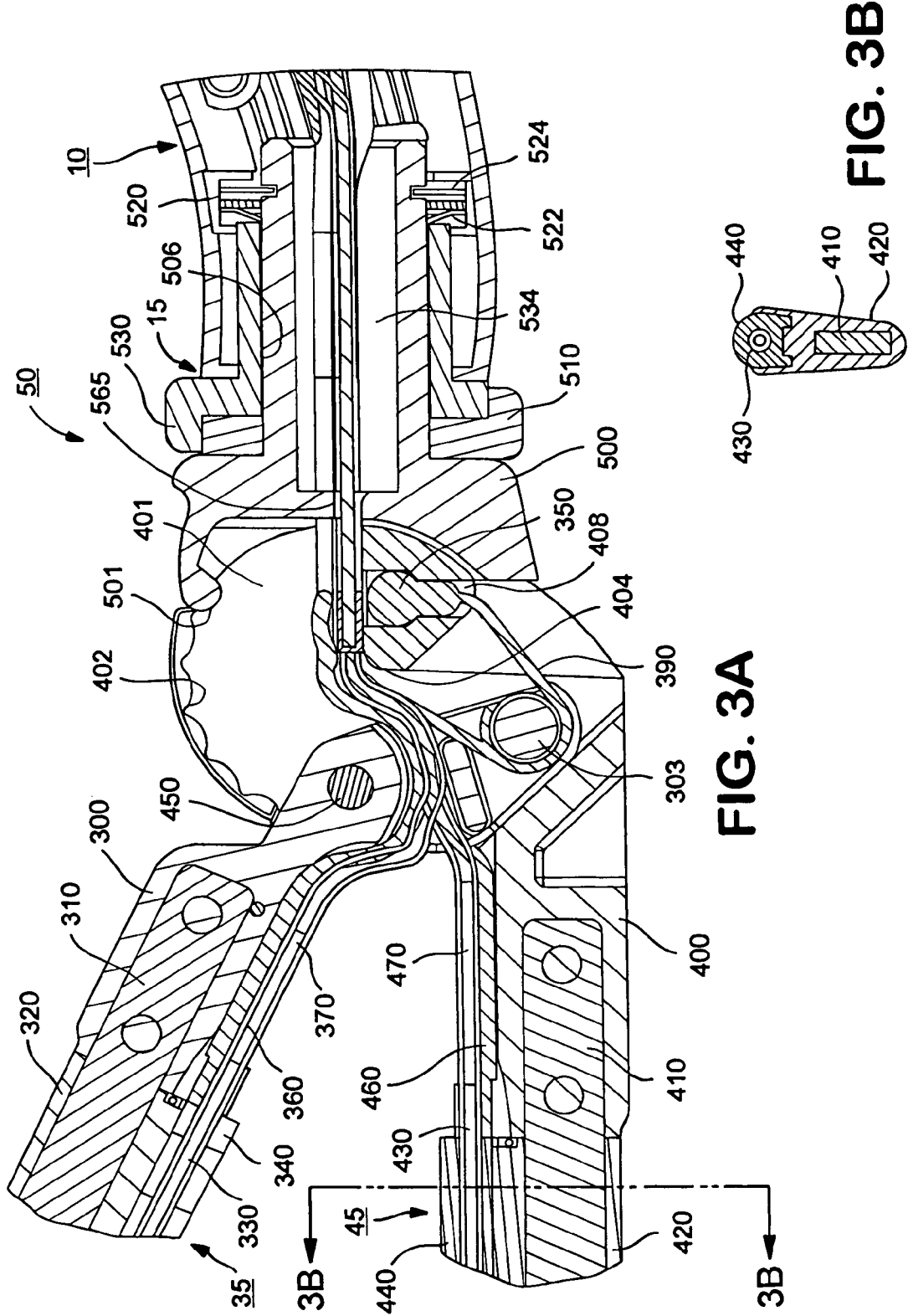

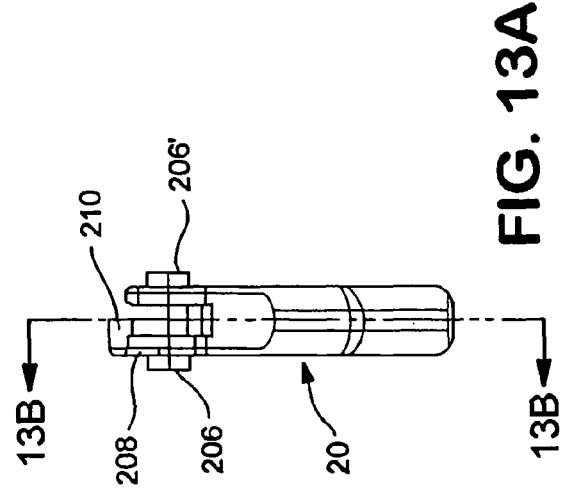
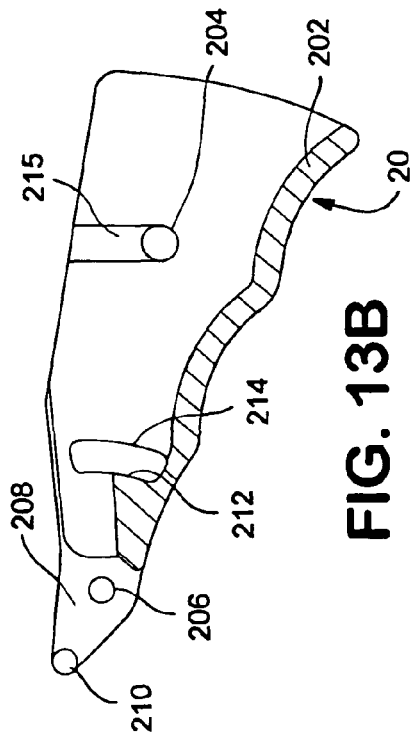
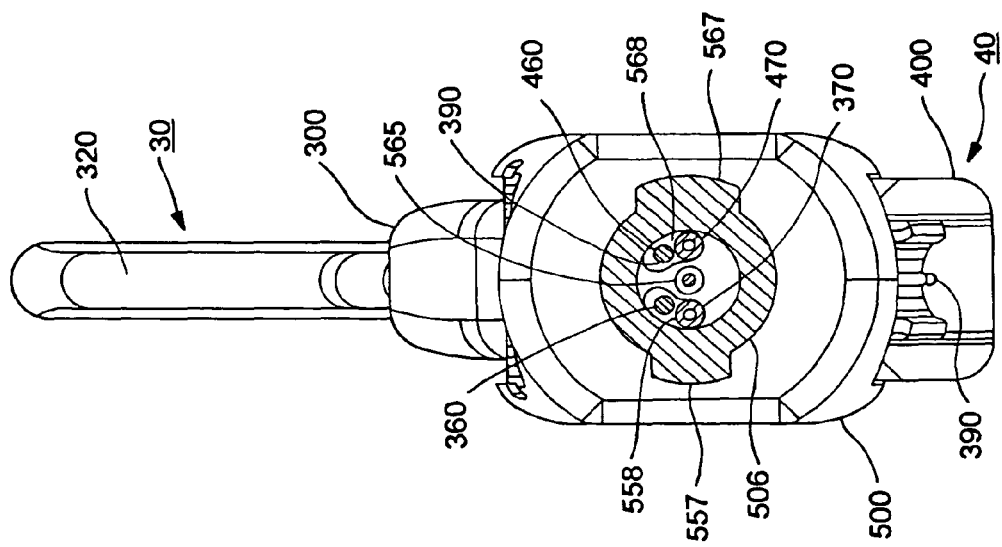

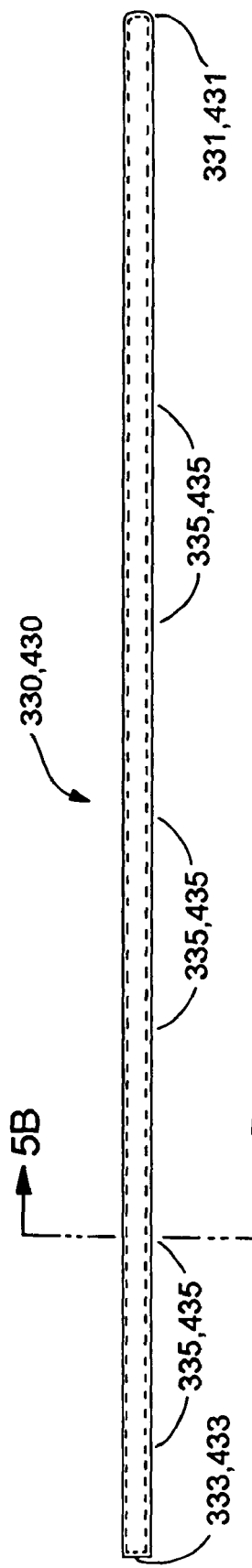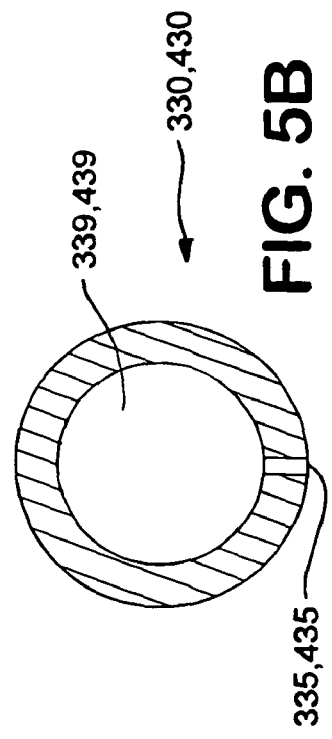
FIG. 5A
FIG. 5B

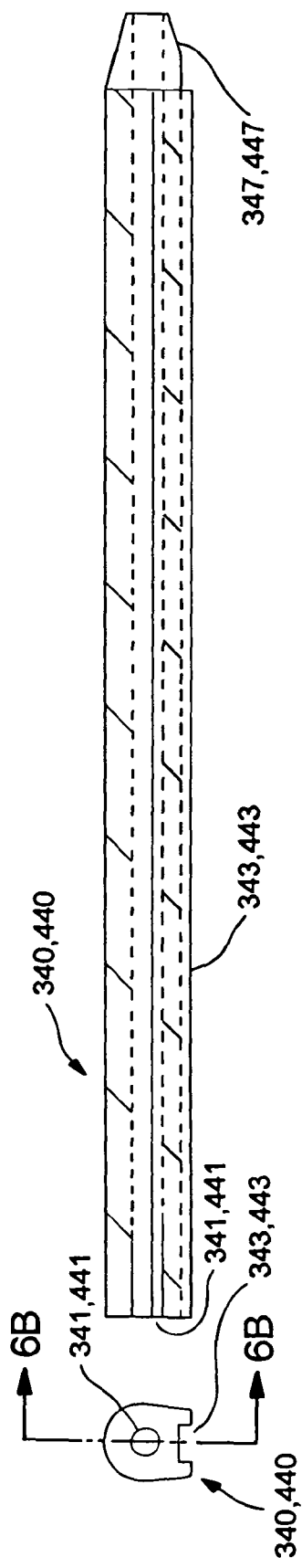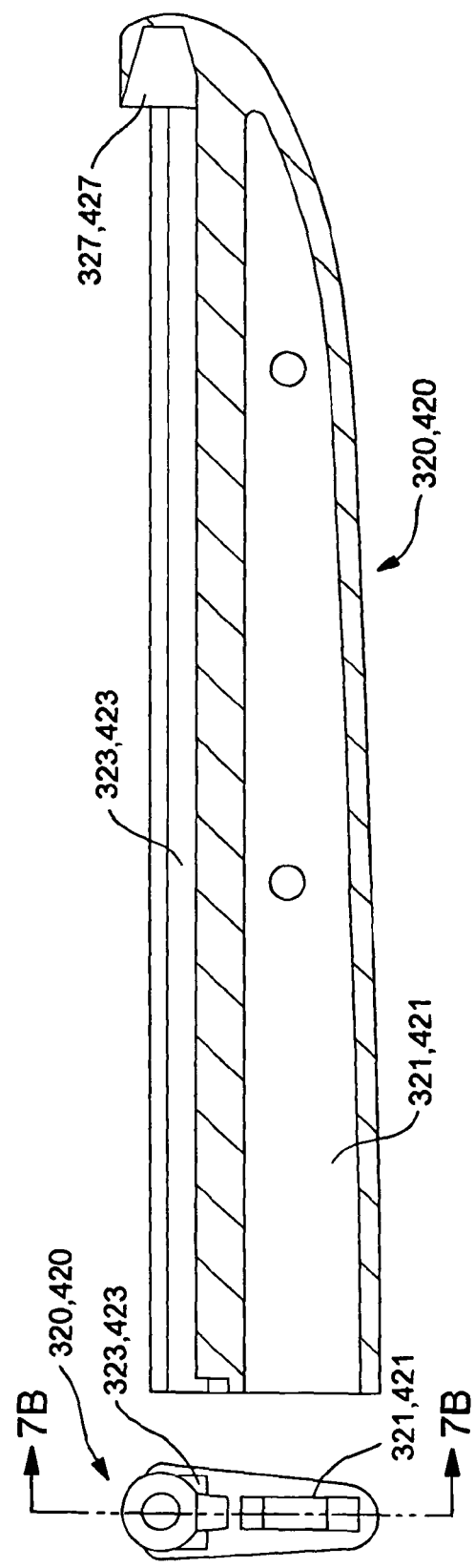

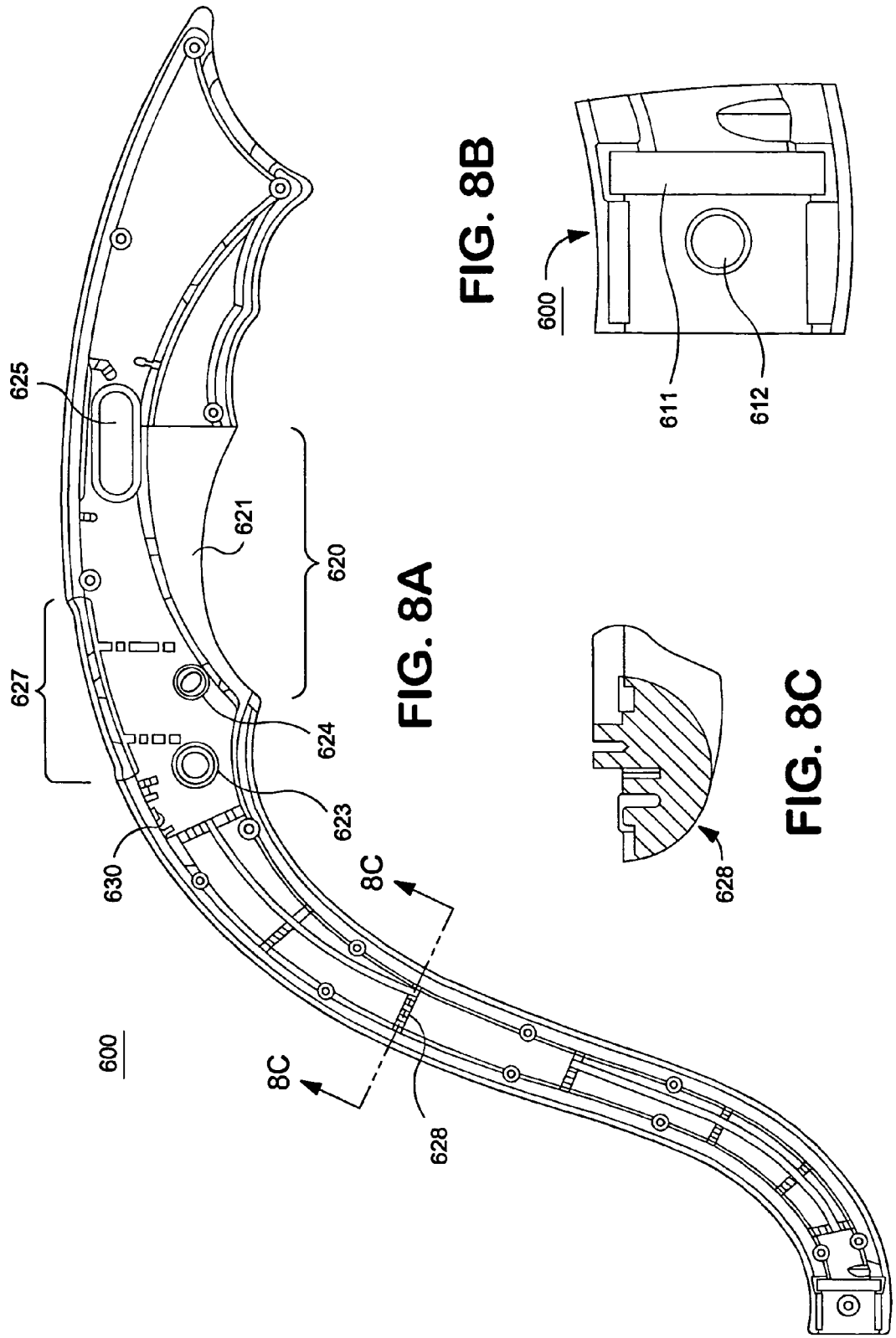

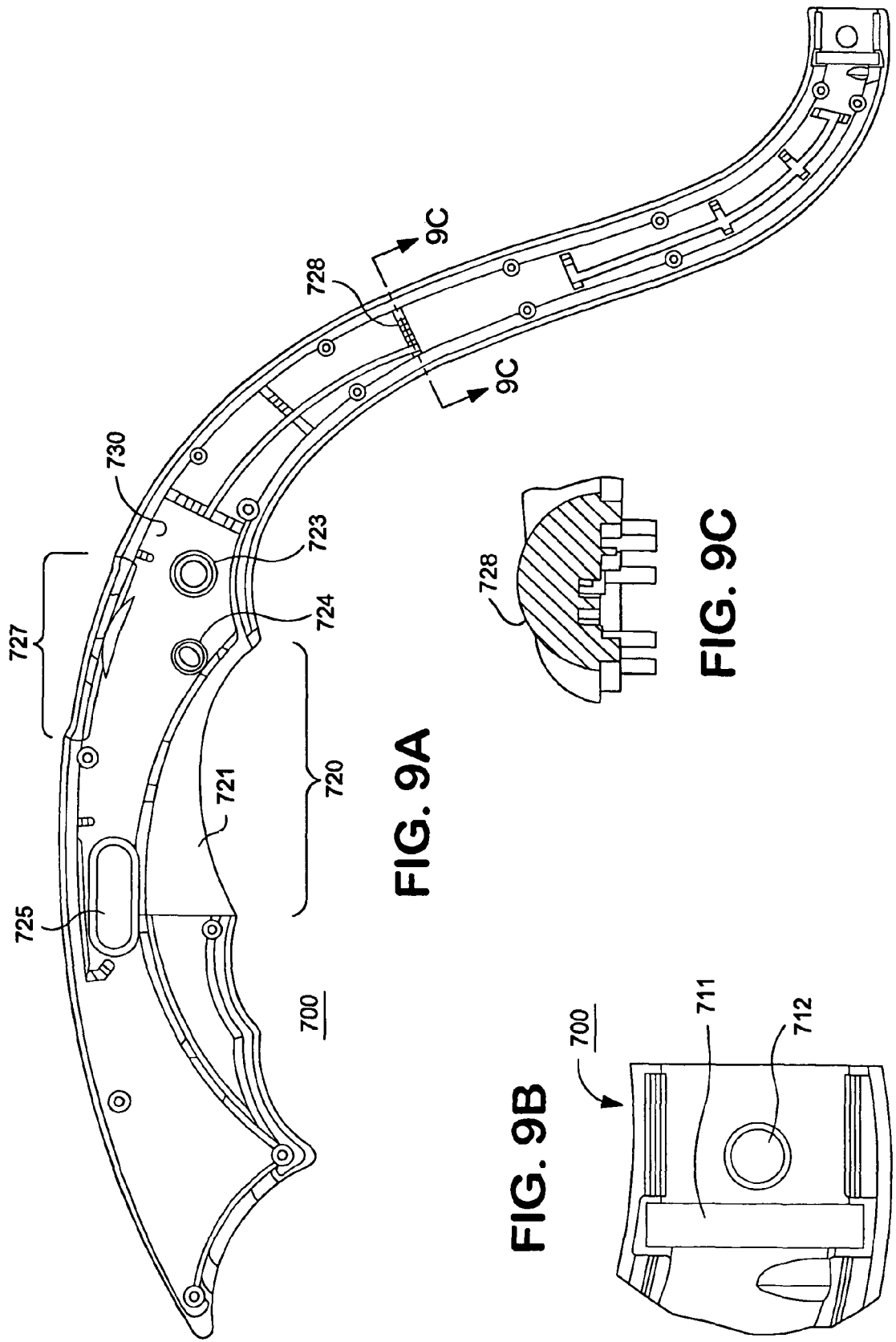

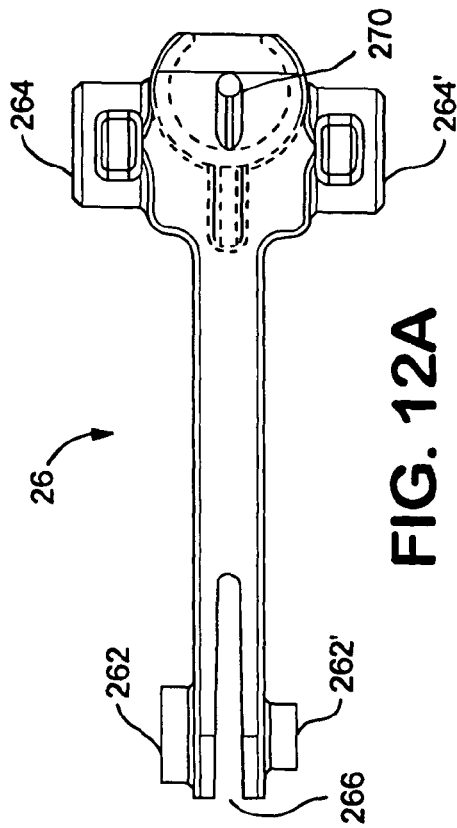
FIG. 12A
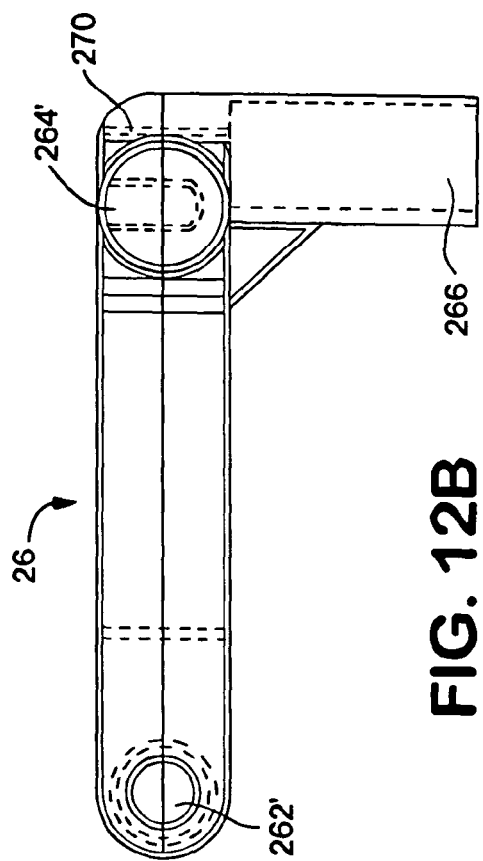
FIG. 12B
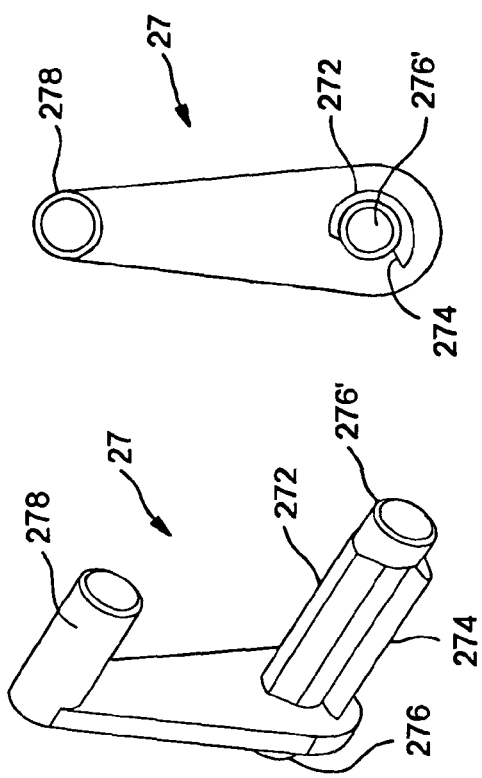
FIG. 11A
FIG. 11B

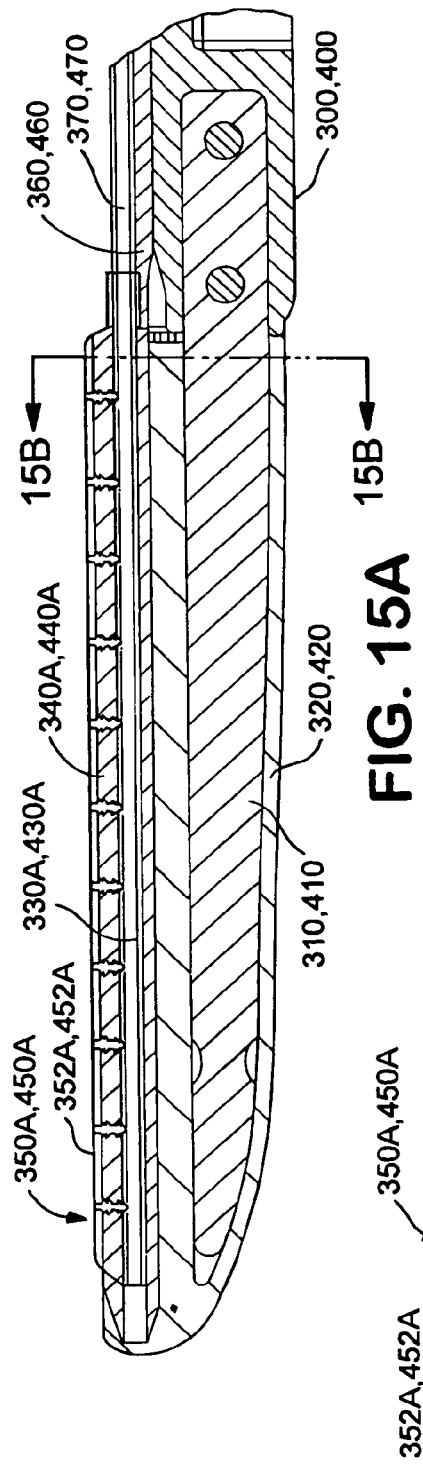
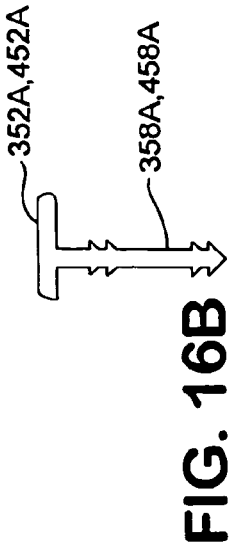
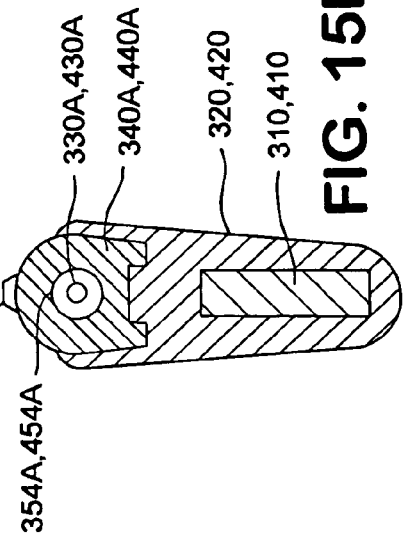
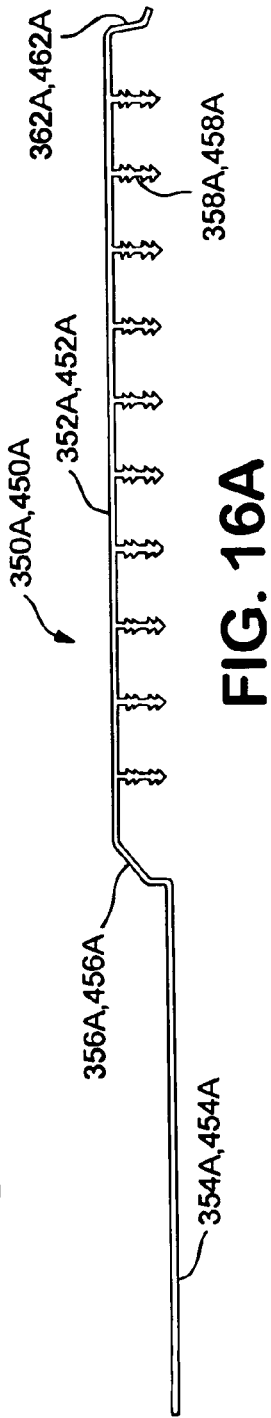
FIG. 15A
FIG. 15B
FIG. 16A
FIG. 16B

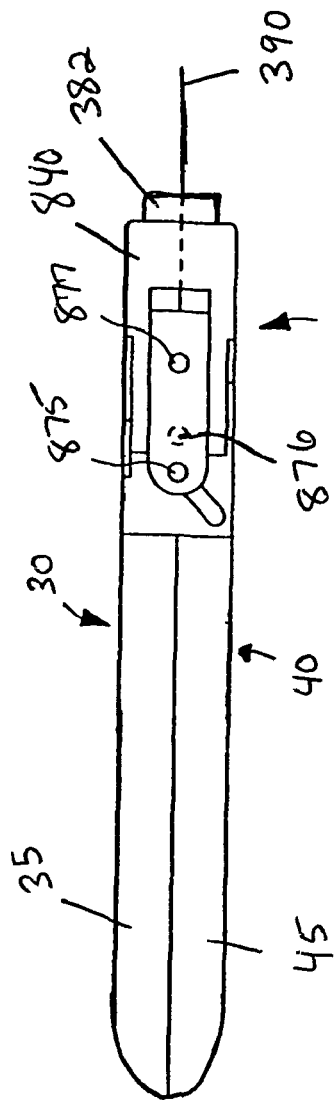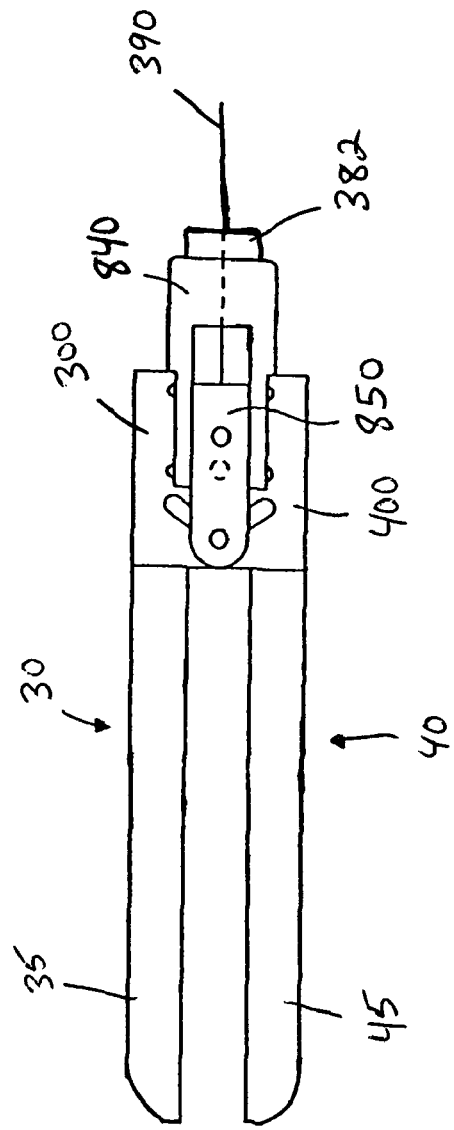
Fig. 42
Fig. 43

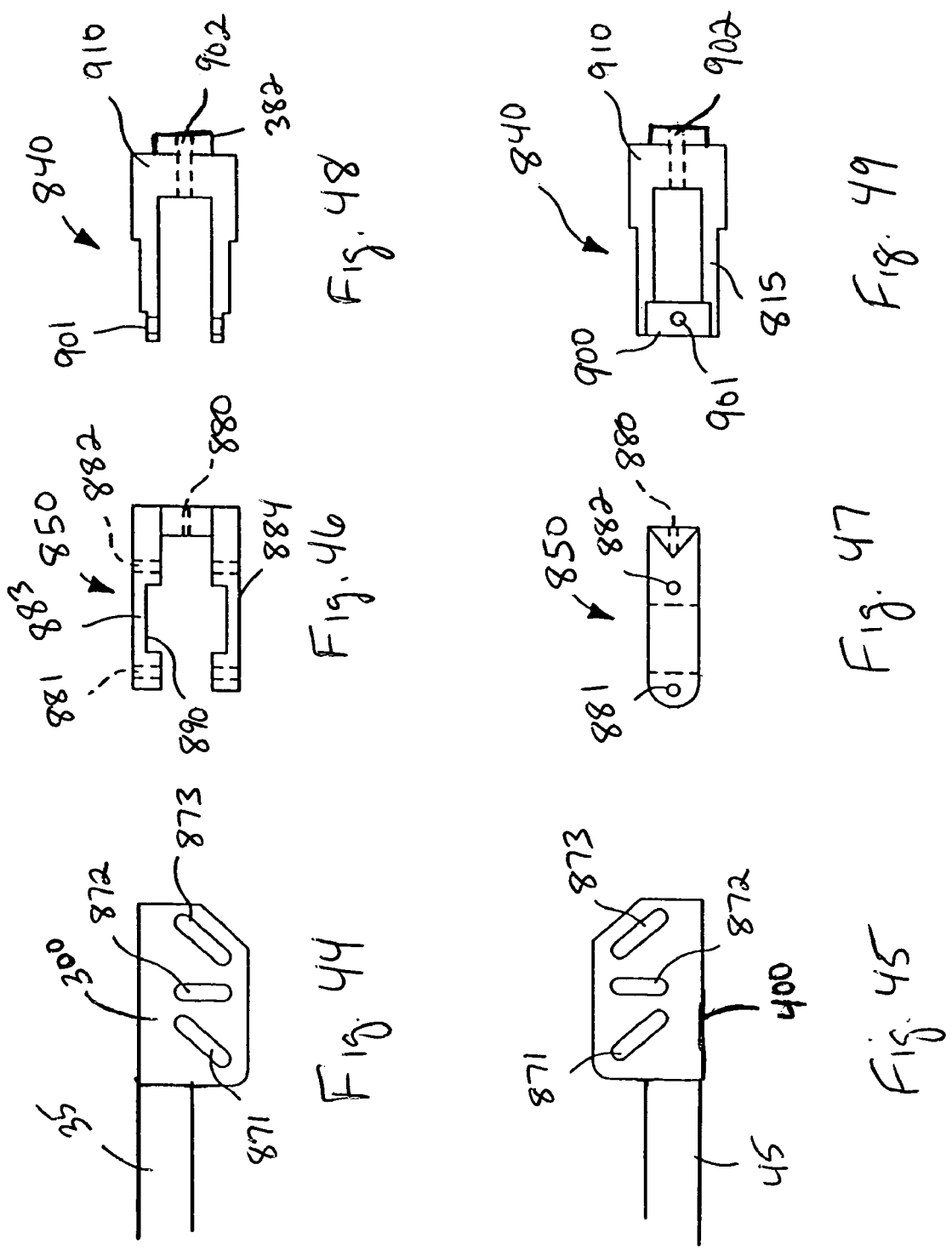

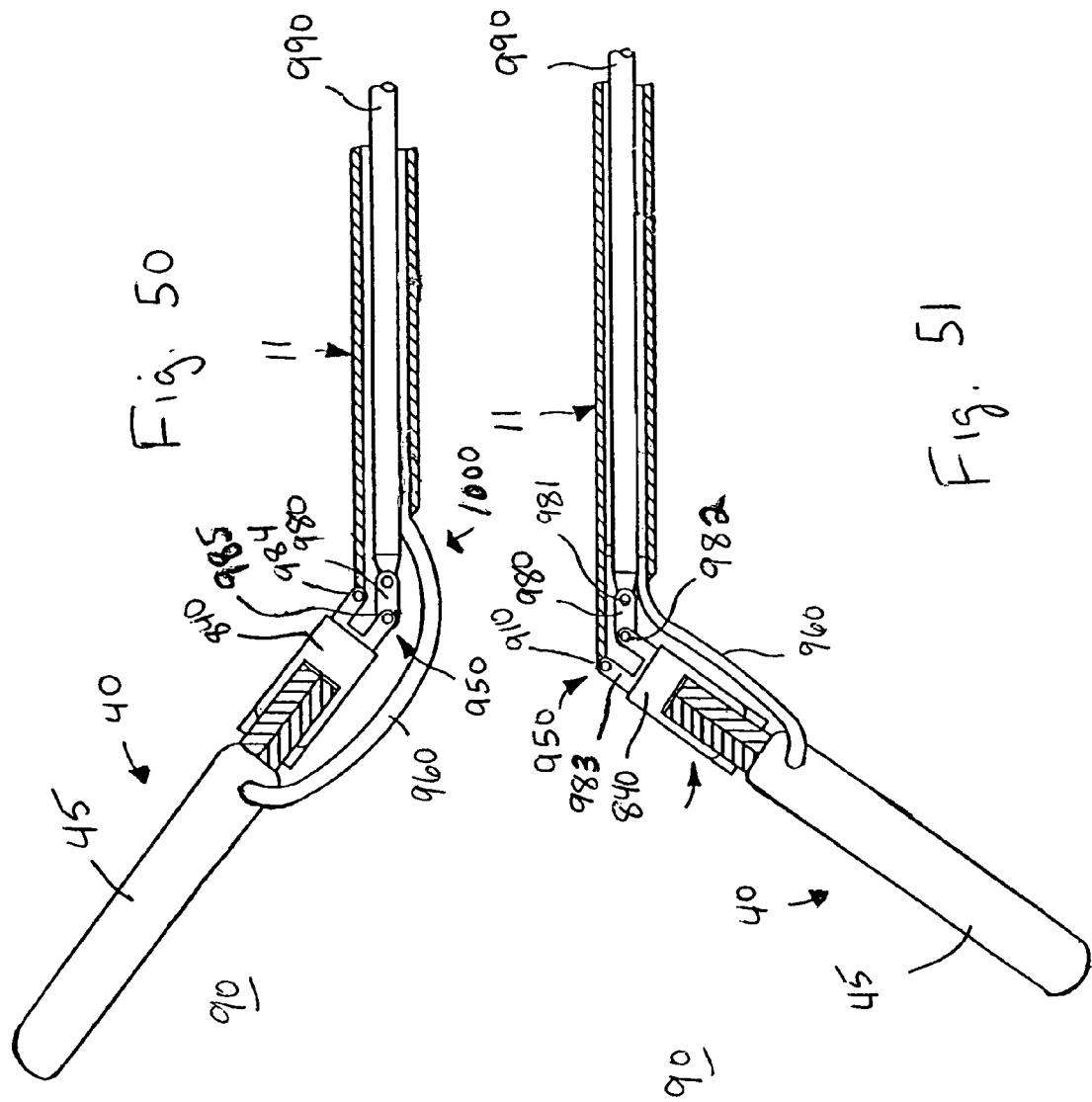

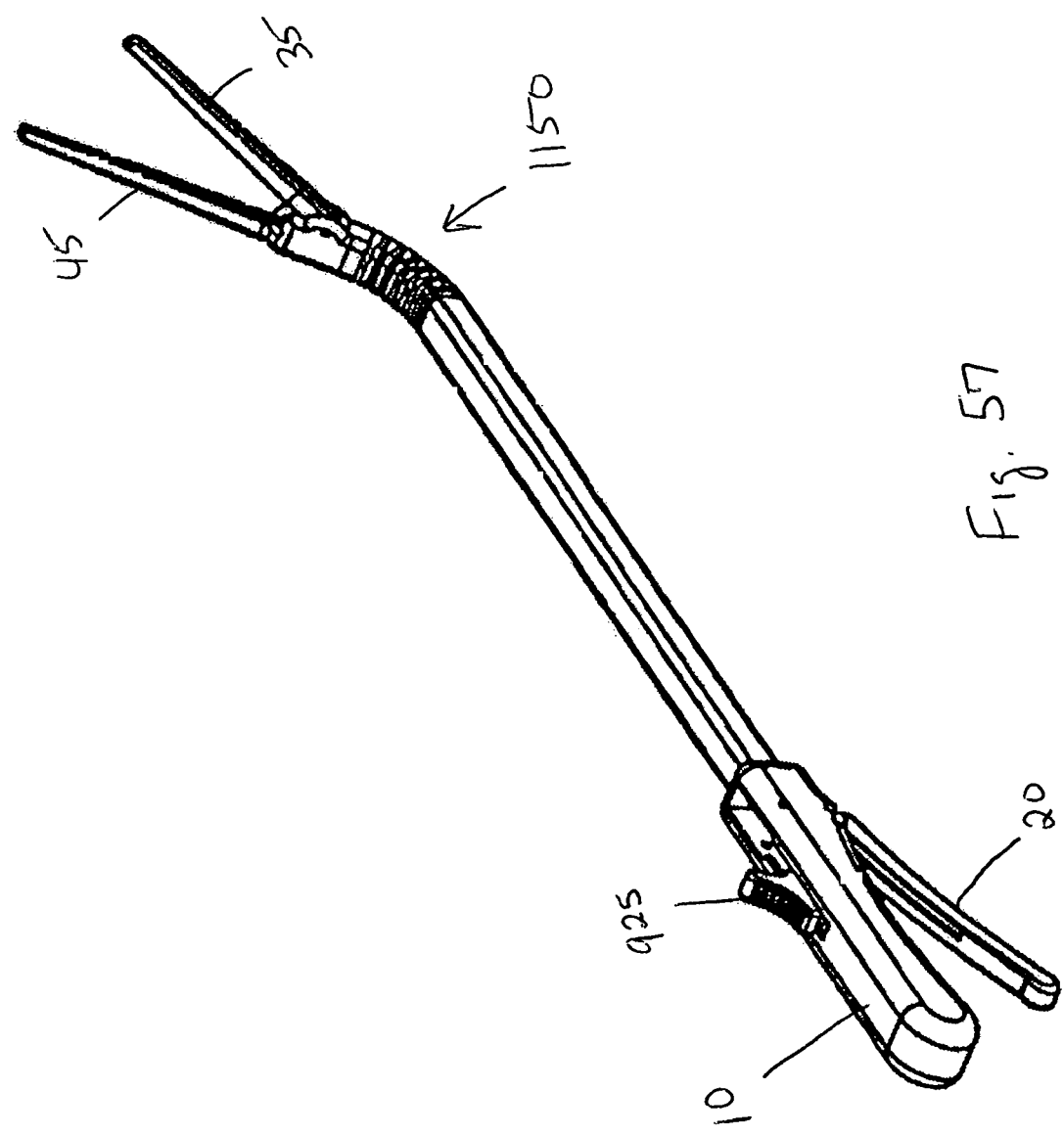

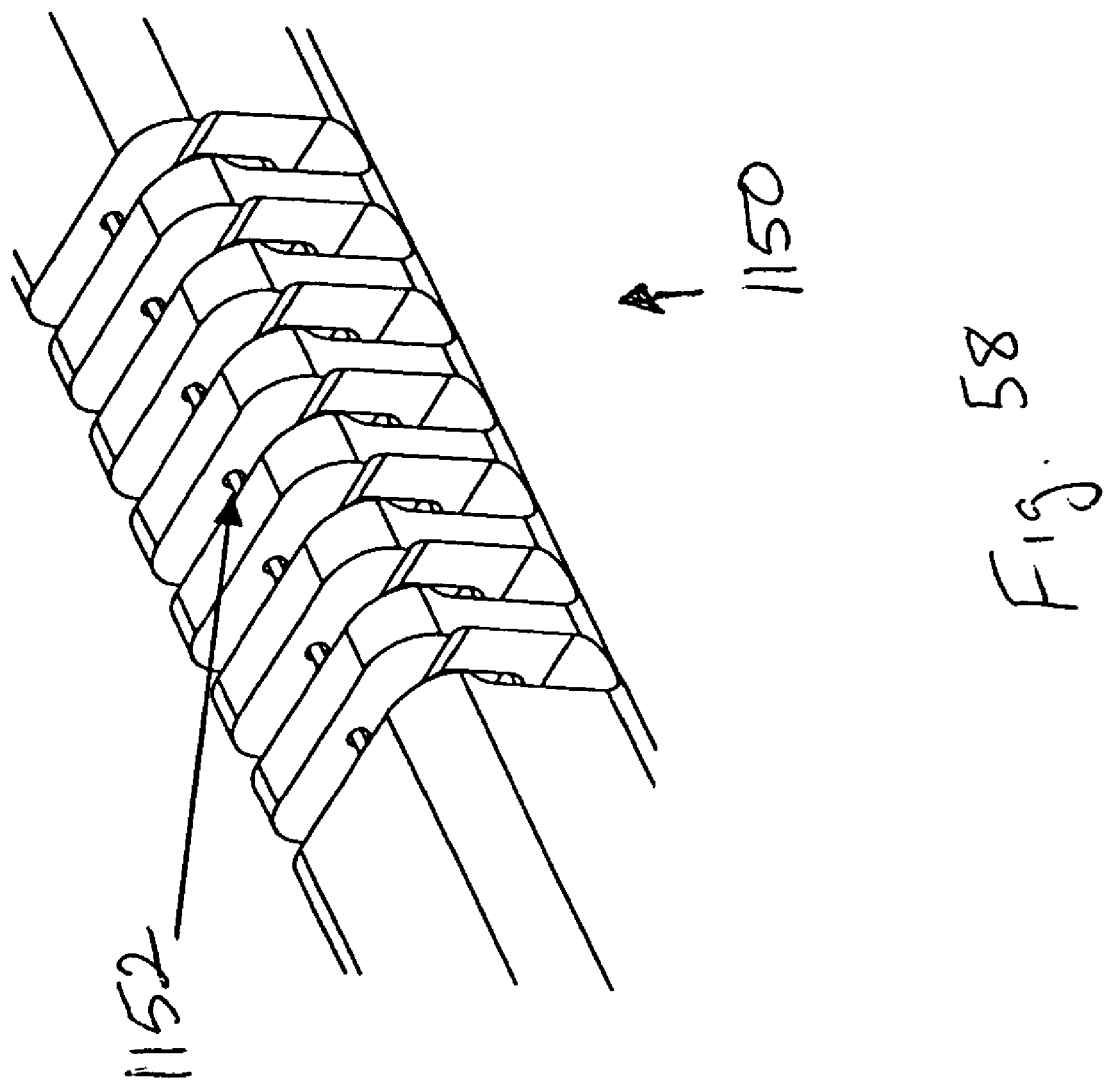

ELECTROSURGICAL HEMOSTAT

CROSS-REFERENCE TO RELATED APPLICATIONS

This application is a continuation-in-part of U.S. patent application. Ser. No. 10/621,893, filed Jul. 17, 2003, now U.S. Pat. No. 7,083,620, which claims priority from U.S. Provisional Patent Application No. 60/422,330 filed Oct. 30, 2002, incorporated herein by reference in their entirety.

BACKGROUND OF THE INVENTION

The present invention relates to surgical tools and procedures generally and relates more particularly to the use of electrosurgical ablation to treat atrial fibrillation.

In patients with chronic atrial fibrillation or having atrial tachycardia that is resistant to medical treatment, the Maze III procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring. While the Maze procedure is successful in treating atrial fibrillation, the procedure is quite complex and is currently practiced by only a few very skilled cardiac physicians in conjunction with other open-heart procedures. The procedure also is quite traumatic to the heart, as in essence the right and left atria are cut into pieces and sewed back together, to define lines of lesion across which the depolarization wavefronts will not propagate.

It has been suggested that procedures similar to the Maze procedure could be instead performed by means of electrosurgical ablation, for example, by applying radiofrequency (RF) energy to internal or external surfaces of the atria to create lesions across which the depolarization wavefronts will not propagate. Such procedures are disclosed in U.S. Pat. No. 5,895,417, issued to Pomeranz, et al., U.S. Pat. No. 5,575,766, issued to Swartz, et al., U.S. Pat. No. 6,032,077, issued to Pomeranz, U.S. Pat. No. 6,142,944, issued to Swanson, et al., U.S. Pat. No. 5,871,523, issued to Fleischman, et al. and U.S. Pat. No. 6,502,575, issued to Jacobs et al., all incorporated herein by reference in their entireties. Hemostat type, electrosurgical or cryo-ablation devices for use in performing such procedures are described in U.S. Pat. No. 5,733,280 issued to Avitall, U.S. Pat. No. 6,237,605 issued to Vaska, et al, U.S. Pat. No. 6,161,543, issued to Cox, et al., PCT published Application No. WO99/59486, by Wang and in pending U.S. patent application Ser. No. 09/747,609 filed Dec. 22, 2000 by Hooven, et al., all incorporated herein by reference in their entireties. In order for such procedures to be effective it is desirable that the electrosurgically created lesions are continuous along their length and extend completely through the tissue of the heart (i.e. transmural lesions). These goals may be difficult to accomplish employing dry ablation electrodes or electrodes applied only to the interior or exterior surfaces of the heart tissue. Electrosurgical hemostats configured to allow fluid-assisted tissue ablation are generally described in U.S. Pat. No. 6,096,037, issued to Mulier, also incorporated by reference in its entirety.

SUMMARY OF THE INVENTION

The present invention provides an ablation hemostat, particularly useful in performing a maze type procedure by applying ablation energy (e.g. RF energy) across the walls of the left and right atria by means of delivery means located on either side of the atrial walls. In a preferred embodiment of the invention, the hemostat is provided with elongated RF electrodes malleable to assume various straight and curved configurations to produce lesions that approximate the incisions that would occur during the Maze III procedure as described in the book '*Cardiac Surgery Operative Technique*' by Donald B. Doty, M.D. at pages 410-419, incorporated herein by reference in its entirety, or to allow creation of lines of lesion corresponding to the incisions that would be provided by other forms of the Maze procedure. The hemostat may be useful in conjunction with other procedures as well.

The hemostat of the present invention is provided with a number of useful features, particularly adapted to ease its use in conjunction with creating elongated lines of lesion. While the disclosed and most preferred embodiments of the invention employ a number of the of the improved features, each of the improved features discussed below is believed valuable in and of itself to improve the performance and ease of use of prior art electrosurgical hemostats.

In order to allow the hemostat, in one embodiment of the invention, to produce straight and curved elongated lesions, the jaws of the hemostat are malleable to allow the physician to set the specific jaw configuration. The jaws are fabricated of a flexible plastic sheath enclosing elongated bendable or malleable backbones and electrodes to achieve this result. The backbones and electrodes may be shaped by the physicians' fingers into a desired curvature and serve to retain the curvature imparted to them until reshaped for creation of a subsequent lesion. The backbones take the form of elongated plates having thicknesses substantially less than their widths to encourage bending of the jaws within a single plane so that the opposed electrodes can more readily be maintained in alignment along their lengths. The backbones are also preferably tapered along their length such that the width of the backbones diminishes as they approach the tips of the jaws, in turn making it easier to provide the jaws with the curvature extending over the entire length of the jaws.

In one embodiment of the invention, the hemostat includes an elongated handle portion or handle and a jaw assembly mounted at the distal end of the handle. The elongated handle portion may include one or more malleable and/or articulating components. The jaw assembly preferably includes two elongated jaws carrying RF electrodes or other ablation elements, extending along the lengths of the jaws and arranged so that they are located on opposite sides of tissue compressed between the jaws. In preferred embodiments, the electrodes take the form of fluid irrigated RF electrodes, however, other ablation mechanisms such as cyroablation, direct current ablation, microwave ablation, ultrasound ablation, and the like may be substituted for RF ablation electrodes.

The jaw assembly may include a swiveling head assembly adapted to allow the jaws to be rotated relative to the axis of the handle (roll) and/or allowing the jaws to pivot around an axis perpendicular to the axis of the handle (pitch). Adjustment of the jaws relative to the handle (pitch and/or roll) is made manually by the physician, and the jaws are retained in their desired orientation relative to the handle by means of detent mechanisms.

The jaws may be mounted to one another at a pivot point and are opened and closed by means of a trigger, mounted to the handle, which applies tensile force to a cable or other tension member extending along the handle. The cable, when pulled, pulls the jaws toward one another to compress tissue between them. In the particular embodiments disclosed, the cable is anchored offset from the pivot point to a first one of the jaws. The first jaw is fixed, i.e. retains its location during jaw closure regardless of the pitch and/or roll adjustment made to the jaw assembly. The second, pivoting jaw, is mounted to the fixed jaw at a pivot point and the cable passes around an internal boss within the pivoting jaw, also offset from the pivot point. Application of tension to the tension member pulls the internal boss in the pivoting jaw toward the cable mounting point in the fixed jaw and thereby causes movement of the jaws toward one another. Tissue placed between the jaws can thus be engaged by the jaws and compressed between the jaws as the jaws close.

A cable may enter the jaw assembly along its rotational (roll) axis, so that rotation of the jaw assembly about the roll axis does not alter the operation of the cable. The cable may extend around a shoulder internal to the fixed jaw, which shoulder remains essentially in the same location regardless of the pitch adjustment of the jaw assembly, so that pitch adjustment of the jaw assembly does not significantly effect operation of the cable to close the jaws.

In some embodiments, the trigger mechanism is provided with a locking detent mechanism which may be engaged or disengaged and which, when engaged, retains the trigger in its position, in turn maintaining compression of the jaws against tissue located there between. The detent mechanism in a preferred embodiment is activated or deactivated by means of a sliding button, mounted to the handle.

In some embodiments, irrigation fluid is provided to the electrodes by means of plastic tubing that is provided with in-line flow limiters, controlling the delivery rate of irrigation fluid to the electrodes. This feature allows the use of a simplified fluid pumping mechanism and also provides balanced, even fluid flow to the electrodes. In one embodiment, the trigger, when released, also serves to block fluid flow to the electrodes, preventing irrigation while the hemostat is not in use.

In one embodiment, the RF electrode assembly can take the form of an elongated porous material coupled to the fluid delivery lines and carrying elongated electrode wires on their inner, facing services. The electrode wires may be coupled to the porous material by means of a series of spikes extending from the electrode wires into the porous material. Other alternative electrode designs may of course be substituted, including electrodes comprised of elongated coil electrodes or perforated tubular electrodes with porous material located either inside of or surrounding the electrodes. For example, a perforated tubular electrode can be seated inside a porous polymeric support such the electrode is entirely within the support. In this embodiment, conductive fluid flows through the interior of the electrode, out of perforations in the electrode and through the porous support to facilitate ablation such that the polymeric support, not the electrode, is on the facing surfaces of the jaws to contact the tissue to be ablated.

The hemostat may optionally also include a thermocouple, located along the jaws allowing for temperature controlled feedback of power provided to the RF electrodes and may also preferably include an indicator LED mounted to the handle, activated to indicate that delivery of RF energy is underway. The hemostat may be useable with conventional RF generators. Alternatively, the hemostat may be used in conjunction with an RF generator system, which incorporates a transmurality measurement and automatic shut off of ablation energy.

In some embodiments of the invention, the jaws or portions thereof may be rigidly straight and/or curved. One or more portions of the jaw assemblies might be replaceable or interchangeable. The upper and/or lower jaw of the jaw assembly may include one or more pivots. In some embodiments of the invention, the device includes a means for opening and/or closing the lower jaw of the jaw pair while maintaining the upper jaw in a stationary position. In alternative embodiments of the invention, the device includes a means for opening and/or closing the upper jaw of the jaw pair while maintaining the lower jaw in a stationary position. In alternative embodiments of the invention, the device includes a means for opening and/or closing the upper and lower jaws of the jaw pair while neither jaw is maintained in a stationary position. In some embodiments of the invention, the device may include one or more sensors. In some embodiments of the invention, the device includes one or more remote actuators for remotely actuating one or more components of the device. In some embodiments of the invention, the device includes one or more shapeable or malleable components. In some embodiments of the invention, the device includes one or more components that actuated via a cable or rod mechanism.

BRIEF DESCRIPTION OF THE DRAWINGS

FIG. 3A is a cross-section view through the jaw assembly of the hemostat of FIG. 1.

FIG. 3B is a cross-section view through lines 3B-3B of FIG. 3A.

FIG. 4 is an end view in partial cross-section of the proximal end of the knuckle portion of the jaw assembly of the hemostat of FIG. 1.

FIG. 5A is a plan view of an elongated tubular electrode used in the hemostat of FIG. 1.

FIG. 5B is an enlarged cross-section view taken along lines 5B-5B of the electrode illustrated in FIG. 5A.

FIG. 6A is an end view of an electrode support as used in the jaw assembly of the hemostat of FIG. 1.

FIG. 6B is a cross-section view taken along lines 6A-6A of FIG. 6A illustrating the electrode support.

FIG. 7A is an end view of an electrode sheath as included in the jaw assembly of the hemostat of FIG. 1.

FIG. 7B is a cross-section view taken along lines 7B-7B of FIG. 7A illustrating the electrode sheath.

FIG. 8A is a plan view of the right half of the handle employed in the hemostat of FIG. 1.

FIG. 8B is an enlarged plan view of the distal portion of the right handle half illustrated in FIG. 8A.

FIG. 8C is a cross-section view taken along lines 8C-8C through the right handle half of the hemostat of FIG. 1.

FIG. 9A is a plan view of the left half of the handle employed in the hemostat of FIG. 1.

FIG. 9B is an enlarged plan view of the distal portion of the left handle half illustrated in FIG. 9A.

FIG. 9C is a cross-section view taken along lines 9C-9C through the left handle half of the hemostat of FIG. 1.

FIG. 11A is a perspective view of a trigger lock as employed in the trigger assembly of the hemostat as in FIG. 1.

FIG. 11B is a plan view of the trigger lock of FIG. 11A.

FIG. 12A is a top plan view of a link arm as employed in the trigger assembly of an assembled hemostat as in FIG. 1.

FIG. 12B is a side plan view of the link arm of FIG. 12A.

FIG. 13A is a side plan view from the distal end of the trigger employed in the trigger assembly of the hemostat of FIG. 1.

FIG. 13B is a cross-section view taken along lines 13B-13B through the trigger of FIG. 13A.

FIG. 15A is a sectional view through an alternative embodiment of an upper and lower jaw for use with a hemostat otherwise as in FIG. 1.

FIG. 15B is a cross-sectional view taken along lines 15B-15B of FIG. 15A.

FIG. 16A is a plan view of an electrode extension employed in the alternative embodiment of the upper and lower jaw depicted in FIGS. 15A and 15B.

FIG. 16B is an expanded view of a barb of the electrode extension depicted in FIG. 16A.

FIG. 26 is a view of a portion of the hemostat according to one embodiment of the present invention.

FIG. 42 is a view of the jaw assembly of one embodiment of the present invention.

FIG. 43 is a view of the jaw assembly of one embodiment of the present invention.

FIG. 44 is a view of a portion of the jaw assembly of one embodiment of the present invention.

FIG. 45 is a view of a portion of the jaw assembly of one embodiment of the present invention.

FIG. 46 is a view of a portion of the jaw assembly of one embodiment of the present invention.

FIG. 47 is a view of a portion of the jaw assembly of one embodiment of the present invention.

FIG. 48 is a view of a portion of the jaw assembly of one embodiment of the present invention.

FIG. 49 is a view of a portion of the jaw assembly of one embodiment of the present invention.

FIG. 50 is a view of a portion of a hemostat according to one embodiment of the present invention.

FIG. 51 is a view of a portion of a hemostat according to one embodiment of the present invention.

FIG. 57 is a view of a hemostat according to one embodiment of the present invention.

FIG. 58 is a view of a portion of a hemostat according to one embodiment of the present invention.

DETAILED DESCRIPTION OF THE PREFERRED EMBODIMENTS

Figure 1:
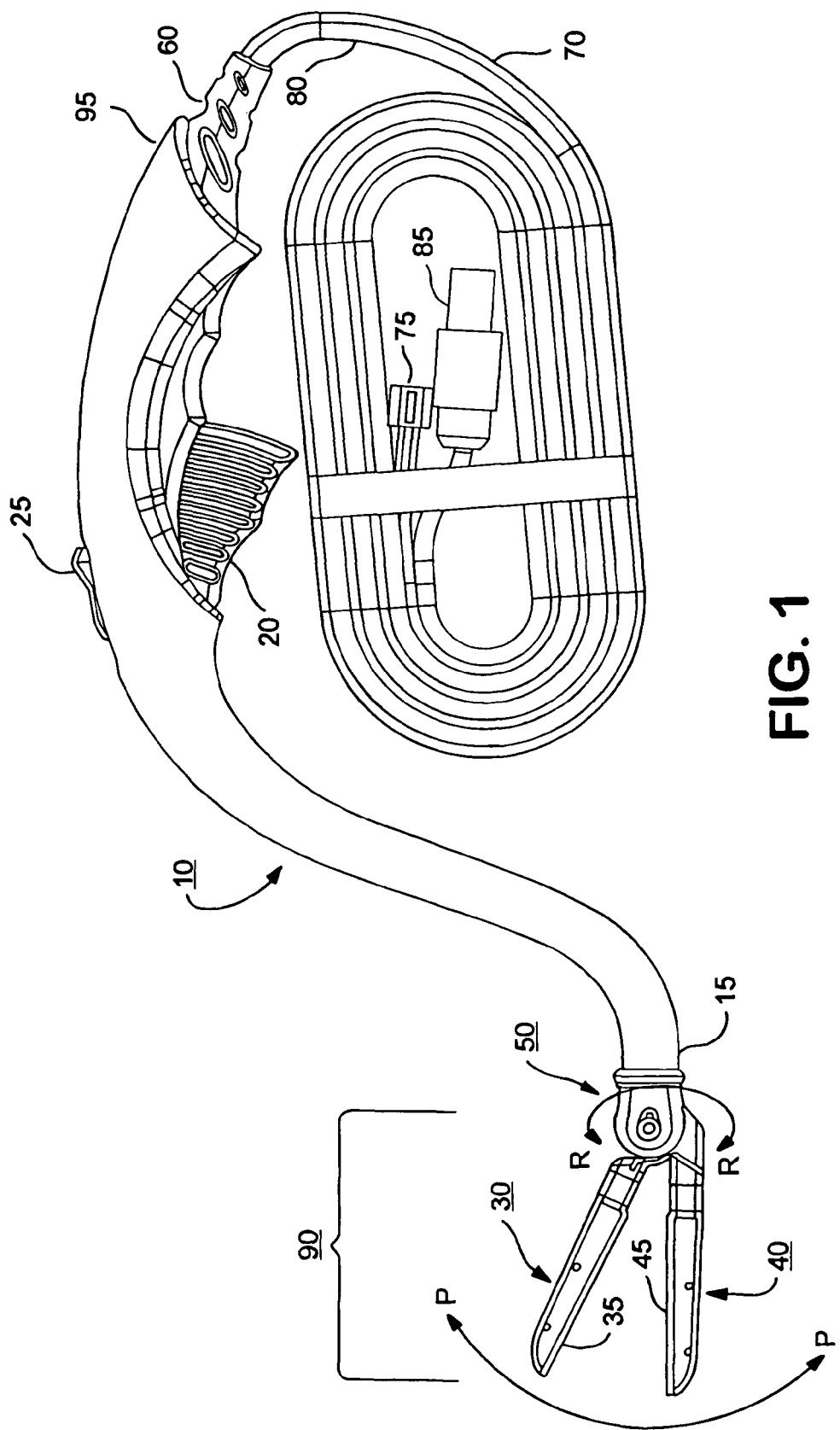
FIG. 1 is a plan view of an assembled hemostat according to one embodiment of the present invention.

In reference to FIG. 1, one embodiment of the hemostat of the present invention generally comprises an elongated handle assembly or handle 10 having a jaw assembly 90 mounted at handle distal end 15, a trigger 20 intermediate the handle proximal and distal ends 95 and 15, and a strain relief 60 located at handle proximal end 95. An elongated cable is coupled to the strain relief 60 and comprises a fluid conduit 70 extending to a proximal fluid fitting 75 adapted to be coupled to a source of conductive fluid and a multi-conductor electrical cable 80 extending to a proximal electrical connector 85 adapted to be coupled to an electrosurgical unit. The trigger 20 is employed to move the jaws of the first or lower jaw assembly 40 with respect to the second or upper jaw assembly 30 of the jaw assembly 90 together to compress tissue therebetween to allow for creation of a linear RF ablation by electrically conductive fluid emitted from electrodes and contacting tissue or direct contact of the electrodes located along the upper and lower jaws 35 and 45.

The jaw assembly 90 includes an upper jaw assembly 30, a lower jaw assembly 40, and a swivel assembly 50, discussed in more detail below. The upper jaw and lower jaw assemblies 30 and 40 have opposed upper and lower jaws 35 and 45, respectively, each comprising a fluid assisted elongated electrode assembly. The upper and lower jaw assemblies 30 and 40 support elongated electrodes, discussed in more detail below, each coupled to one of the insulated conductors within conduit 80 extending proximately through the strain relief 60 to electrical connector 85. Each of the jaws 35 and 40 of respective upper and lower jaw assemblies 30 and 40 are also coupled to fluid conduit 70 enabling delivery of saline or other conductive fluid from a source coupled to fitting 75 along the lengths of the opposed jaws 35 and 45.

The swivel assembly 50, provides the physician with the opportunity to position the jaw assembly 90 in a variety of orientations relative to the handle 10, to facilitate placing the 35 and 45 jaws against tissue to form desired lines of lesions, e.g., the heart wall in performance of the above-described Maze procedure. In one embodiment, the physician may manually grasp and rotate the swivel assembly 50 and the jaw assembly 90 to provide a roll adjustment R, preferably through an arc of at least 300 degrees, relative to the axis of the distal end 15 of the handle 10 through interaction of components of the handle and swivel assembly described further below. In one embodiment, the physician may manually grasp the jaw assembly 90 and adjust it in pitch P relative to the swivel assembly 50 through the interaction of components of the jaw assembly 90 and the swivel assembly 50 described further below. In one embodiment, the available arc of pitch P adjustment extends over at least 90 degrees. Moreover, the upper and lower jaws 35 and 45 may be malleable as described further below. The combination of these features make the hemostat highly versatile in use. In one embodiment, the trigger 20 is employed to open (separate apart) and close (draw together) the jaws 35 and 45 and to compress tissue between the jaws 35 and 45 prior to application of RF energy to create an elongated lesion. A thumb slide 25 may be provided in conjunction with an internal trigger lock, allowing the position of the trigger 20 and the jaws 35, 45 to be locked. After the trigger 20 is drawn toward the handle 10 to close the jaws 35 and 45, the thumb slide 25 is moved distally relative to the handle 10 to cause an internal trigger lock to engage one of a series of ratcheting lock points that define a set of locking locations for the jaws 35, 45, as described further below. Movement of the thumb slide 25 proximally relative to the handle 10 releases the trigger 20 and the jaw assembly 90, allowing the jaws 35, 45 to return to a fully open position. The interaction of the trigger 20, thumb slide 25 and the associated trigger lock mechanism frees the physician from the need to maintain pressure on the trigger 20 to compress tissue between the jaws 35, 45 during the ablation, simplifying operation of the hemostat.

Figure 2:
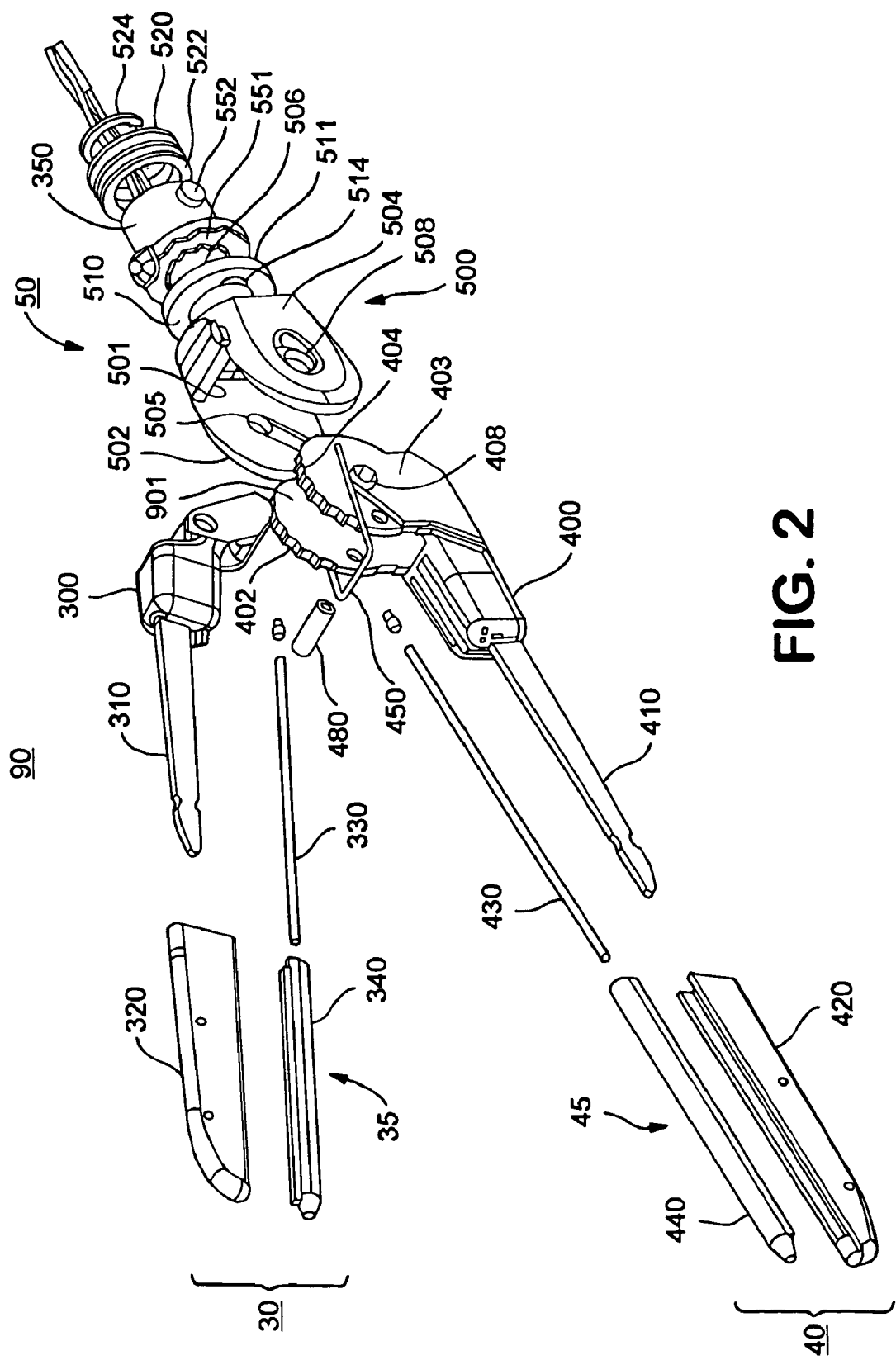
FIG. 2 is an exploded view of the jaw assembly of the hemostat of FIG. 1.

Referring to FIG. 2, the upper jaw assembly 30, in one embodiment of the invention, includes a pivotable, relatively rigid, upper jaw mount 300, an elongated backbone 310, an elongated insulated electrode sheath 320, an elongated conductive electrode 330, and an elongated electrode support 340. Upper jaw mount 300 may be fabricated of plastic or other insulated material, and in preferred embodiments may be fabricated of Teflon filled polycarbonate plastic. Backbone 310 is preferably fabricated of malleable stainless steel or other malleable metal and is attached at a proximal end to upper jaw mount 300. An insulated electrode sheath 320 is fitted over spine 310 with its proximal end located adjacent upper jaw mount 300. The elongated conductive electrode 330 comprises a length of malleable conductive metal tubing as shown in FIGS. 5A and 5B fitted into a lumen of the elongated electrode support 340. The insulated electrode sheath 320 is formed with a channel that receives the subassembly of the elongated conductive electrode 330 and electrode support 340 disposed along the jaw 35. Electrode sheath 320 may be fabricated of a flexible, electrically insulating, material, for example, silicone rubber. Elongated electrode support 340 is preferably fabricated of a porous material, such as Porex™ plastic, allowing for conductive fluid infiltration through its sidewall along its length and correspondingly delivery of conductive fluid along the length of jaw 35. The jaw 35 can therefore be bent laterally with respect to the upper jaw mount 300 to form a curve along the length thereof.

The lower jaw assembly 40 also includes a relatively rigid, lower jaw mount 400, an elongated backbone 410, an elongated insulated electrode sheath 420, an elongated conductive electrode 430, and an elongated electrode support 440 that are all formed of the same materials as the corresponding elements of the upper jaw assembly 30. The assembly of the elongated backbone 410, elongated insulated electrode sheath 420, elongated conductive electrode 430, and elongated electrode support 440 is also shown in FIG. 3B.

The jaw 45 can therefore also be bent laterally with respect to the lower jaw mount 400 to form a curve along the length thereof. In use, the physician manually forms a lateral curve in both the upper and lower jaws 35 and 45 to fit the contour of the tissue, e.g., the heart wall.

The lower jaw mount 400 is formed with a pair of spaced apart, parallel, plates or flanges 401 and 403 each bearing a series of notches 402 and 404, respectively, along the edges thereof. When assembled, a proximal portion of the upper jaw mount 300 is fitted between the flanges 401 and 403. A pin 480 extends through aligned holes through the proximal portion of upper jaw mount 300 and the flanges 401 and 403. The ends of pin 480 are fixed to the flanges 401 and 403 allowing the proximal portion of the upper jaw mount 300 to be rotated about the pin 480, thereby allowing jaws 35 and 45 to open and close. The upper and lower jaws 35 and 45 are separated apart a predetermined distance in the fully closed positions although the electrically insulated distal ends of the insulated electrode sheaths 320 and 420 may contact one another. A spring 450 urges the upper and lower jaws 35 and 45 apart from one another, facilitating opening of the jaws 35 and 45 upon release of the trigger 20 after application of RF energy.

As shown in FIGS. 2 and 3A, the swivel assembly 50 includes a swivel 500 that may also be fabricated of Teflon filled polycarbonate plastic to have a tubular proximal swivel portion 506, a pair of parallel plates or flanges 502 and 504 extending distally from swivel proximal portion 506 and a extending detent 501 extending laterally between flanges 502 and 504. The jaw assembly 90 is mounted to the swivel assembly 50 by outwardly and laterally extending bosses 405 on the outer surfaces of flanges 401 and 403 that are fitted into bores 503 through swivel flanges 502 and 504. The upper jaw mount 300 is mounted to the lower jaw mount 400 by pin 480 as described above, and the lower jaw mount is 400 pivotably mounted relative to the swivel 500. Therefore, the upper and lower jaw assemblies 30 and 40 may be pivoted together relative to the swivel 500, allowing for movement of the jaws 35 and 45 together through the range of pitch P adjustment. The selected pitch P adjustment is maintained by the engagement of the detent 501 into an opposed pair of notches 402 and 404, stabilizing the upper and lower jaws 35 and 45 in a desired orientation relative to the swivel assembly 50. In use, the physician adjusts the relative positions of the jaws 35 and 45 relative to the swivel assembly 50 by simply manually moving the jaw assemblies 30 and 40 in the pitch P direction around the pivot axis defined by bosses 405 within the corresponding bores 505 in swivel flanges 502 and 504. The detent 501 simply rides over the ridges separating adjacent notches 402 and 404.

As noted above, the swivel assembly 50 and the upper and lower jaw assemblies 30 and 40, in one embodiment of the invention, may be rotated around the axis of the distal end 15 of the handle 10 to a desired roll adjustment R to facilitate positioning the jaws 35 and 45 for creation of elongated lesions. The proximal portion 506 of swivel 500 is rotatably mounted within a collar 550 that is mounted fixedly to the distal end 15 of the handle 10 as shown in FIG. 3A. The collar 550 has a wavy or sinusoidal distally facing surface 551 of collar 550. A washer-shaped insert 510 having a wavy or sinusoidal proximally facing surface 511 is fitted over the elongated proximal portion 506 of swivel 500 and attached to the swivel 500 through notches 514, engaging corresponding bosses 557 and 567 (shown in FIG. 4) formed on swivel 500. A C-clip 524 mounted in a circumferential groove formed in the proximal portion 506 of swivel 500 maintains the proximal portion 506 within the lumen of collar 550. A spring washer 522 and a flat washer 520 are interposed between the C-clip 524 and the proximal end of collar 550. Spring washer 522 urges the wavy or sinusoidal surfaces of collar 550 and insert 510 against one another, whereby a plurality of detent locations are defined that maintain a selected roll R adjustment relative to the distal end 15 of the handle 10. In use, the physician may adjust the roll R of the jaw assembly 90 by simply turning the swivel assembly 50 relative to the handle 10. The detent mechanism maintains the swivel assembly 50 in the selected desired roll R adjustment prior to and during closure of the jaws 35, 45 to compress tissue during application of RF energy.

A cable 390 is also shown in FIGS. 3A and 4 that extends from the trigger 20 and that is employed to open and close the jaws 35 and 45. Cable 390 passes through the internal lumen of proximal swivel portion 502, through cable bore 565, around shoulder 404 of lower jaw mount 400, around boss 303 in upper jaw mount 300 and then upward into bore 408 in lower jaw mount 400. The distal end of the cable 390 is maintained within bore 408 by ball 350. When the cable 390 is pulled proximally by squeezing trigger 25, boss 303 of upper jaw 300 is pulled toward bore 408 in lower jaw 400, thereby pulling upper jaw 35 toward lower jaw 45, allowing for compression of tissue there between. It should be noted that during this operation, the lower jaw mount 400 remains fixed relative to the swivel assembly 50 and only upper jaw mount 300 moves relative to the swivel assembly 50 or the handle 10. Proximal movement of cable 380 does not affect the position of the lower jaw 45 relative to the handle 10, nor does it affect the selected roll R adjustment of swivel 500. Rotation of the jaw assembly 90 and swivel 500 about the roll axis does not affect the operation of the cable 390 because the cable 390 passes through the swivel 500 and enters the jaw assembly 90 along the roll axis. Pitch P adjustment of the jaw assembly 90 does not significantly effect operation of the cable 390 in opening or closing the jaws 35, 45 because shoulder 404 is at the center of rotation of lower jaw mount 400 relative to swivel 500 and remains essentially in the same location regardless of the pitch P adjustment.

FIGS. 3A and 4 also internal electrical wiring and fluid delivery conduits of this embodiment of the invention including, insulated conductors 360 and 460 and fluid conduits 370 and 470 that both terminate at connections with the proximal ends of the upper and lower electrodes 330 and 430, respectively. The fluid conduits 370 and 470 deliver conductive fluid into the lumens of the tubular upper and lower electrodes 330 and 430, respectively. As shown in FIG. 4, the upper insulated conductor 360 and the upper fluid conduit 370 are routed to one side of the cable 390, and the lower insulated conductor 460 and the lower fluid conduit 470 are routed to the other side of the cable 390 while passing through the lumen 534.

The elongated tubular electrodes 330 and 430 are illustrated in FIGS. 5A and 5B. The tubular electrodes 330 and 430 are preferably formed of thin-walled, malleable stainless steel tubing extending between a proximal open end 331, 431 and a distal closed end 333, 433. A series of fluid ports 335, 435 are formed, e.g., by laser drilling, through the sidewall of the tubing from the lumen 339, 439 and extending in a single line, although the fluid ports could be formed in any selected array extending around the circumference of the sidewall of the tubing. The proximal ends 331, 431 are notched in alignment with the series of fluid ports 335, 435 to assist in assembly so that the fluid ports 335, 435 are directed in a particular alignment with the porous electrode support 340, 440.

The porous electrode support 340, 440, depicted in FIGS. 6A and 6B, comprises a length of non-conductive, porous, malleable tubing having a channeled side 343, 443 adapted to fit within an elongated channel 323, 423 of the insulated electrode sheath 320, 420, depicted in FIGS. 7A and 7B. The porous electrode support 340, 440 is conically shaped at the support distal end 347, 447 to fit within a conically shaped terminus 327, 427 of the elongated channel 323, 423 of the insulated electrode sheath 320, 420. During assembly, the elongated tubular electrode 330, 430 is inserted into the elongated lumen 341, 441 of the porous electrode support 340, 440. Preferably, the series of fluid ports 335, 435 are oriented toward the channeled side 343, 443 so that the conductive fluid emitted from the lumen through the series of fluid ports 335, 435 then migrates laterally through the pores of the porous electrode support 340, 440 and around its circumference to thoroughly and uniformly wet the porous electrode support 340, 440 along the upper and lower jaws 35 and 45.

The sub-assembly so formed is fitted into the shaped terminus 327, 427 and the elongated channel 323, 423 of the insulated electrode sheath 320, 420 as also shown in FIGS. 3A and 3B. Adhesive is applied to the contacting surfaces 323, 343 and 423, 443 to maintain the sub-assembly of the elongated tubular electrode 330, 430 inserted into the elongated lumen 341, 441 of the porous electrode support 340, 440 affixed to the insulated electrode sheath 320, 420. The adhesive does not block migration of conductive fluid around the porous electrode support 340, 440. Electrode sheathe 320, 420 is also formed having an elongated tapered internal recess 421 441 that receives the malleable backbone 310, 410 as shown in FIGS. 2 and 3. Again, adhesive may be applied to the contacting surfaces of the backbone 310, 410 and the elongated tapered internal recess 421 441.

Figure 10:
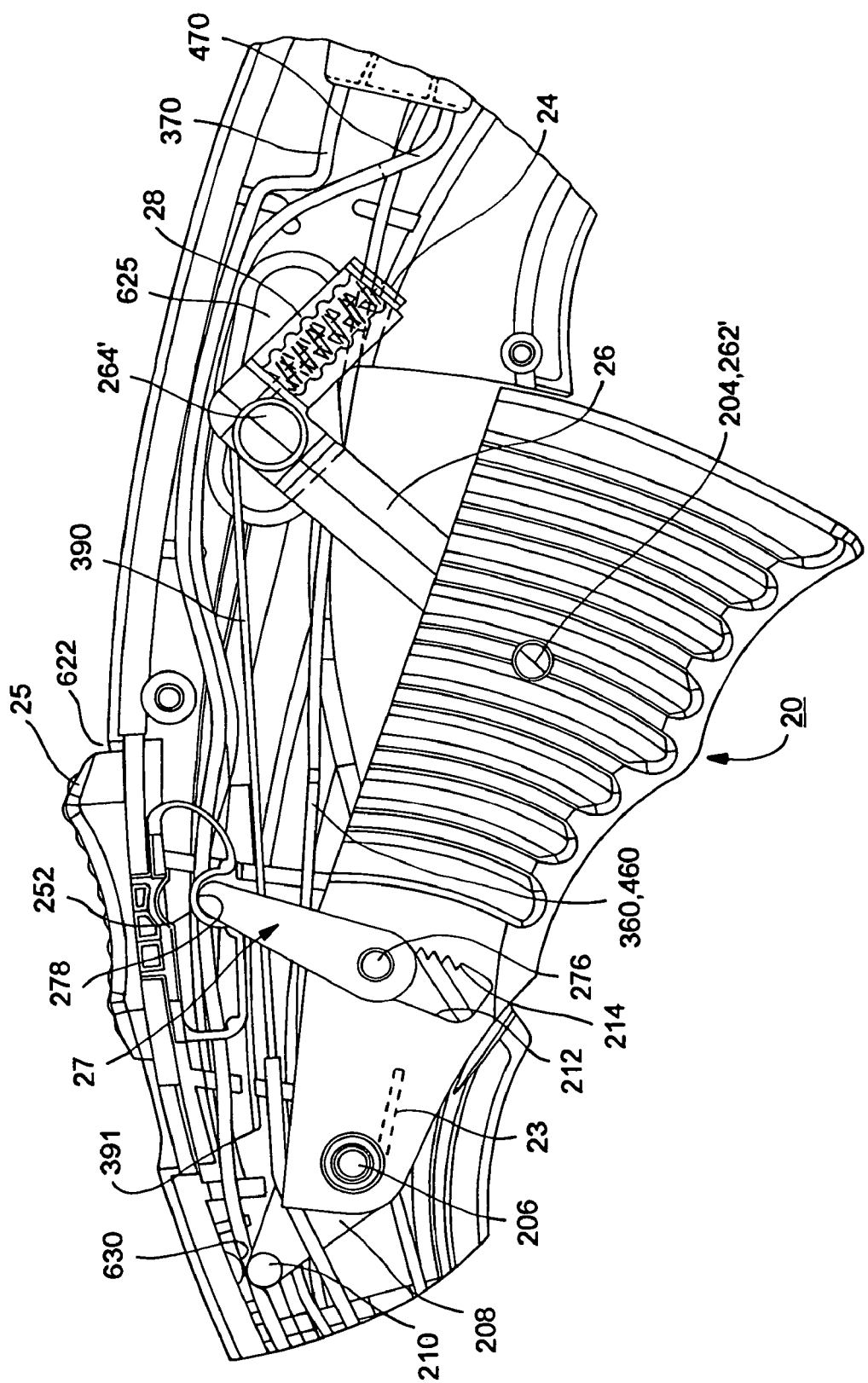
FIG. 10 is an enlarged view of the trigger portion of a hemostat as in FIG. 1 with the left handle half removed.

The handle 10 is formed of a right handle half 600 depicted in FIGS. 8A-8C and a left handle half 700 depicted in FIGS. 9A-9C. Trigger sections 620 and 720 of the respective right and left handle halves 600 and 700 include downwardly opening recesses 621 and 721 in which trigger 20 is mounted (as shown in FIGS. 1 and 10) to pivot inward to apply tension on cable 390 or outward to release tension on cable 390. Upward openings 627 and 727 in respective right and left handle halves 600 and 700 receive the thumb slide 25. Inwardly extending projections 630 and 730 are also formed in respective right and left handle halves 600 and 700 that function to constrict the fluid conduits 370 and 470 to prevent conductive fluid flow therethrough when the trigger 20 is released as described further below.

A set of circular matching, laterally opposed, sockets 623 and 723 are formed in the interior surfaces of the respective right and left handle halves 600 and 700. The set of sockets 623, 723, receive a pair of pivot bosses 206, 206' of trigger 20 (shown in FIG. 13A) about which the trigger 20 pivots as described further below. A set of matching, laterally opposed, and slightly elongated or oblong, sockets 624 and 724 are formed in the interior surfaces of the respective right and left handle halves 600 and 700. The set of sockets 624, 724 receive and guide a trigger lock 27 (shown in FIGS. 11A and 11B) that interacts with trigger 20 as described further below. The oblong shape of the set of sockets 624, 724 assists in allowing the trigger 20 to ratchet along the trigger lock 27 when trigger is drawn inward to tension the cable 390 during closing of the jaws 35, 45 as described further below.

A further set of matching, laterally opposed, elongated sockets 625 and 725 are also formed in the interior surfaces of the respective right and left handle halves 600 and 700. The set of sockets 625, 725 receive and guide a link arm 26 (shown in FIGS. 12A and 12B) that interacts with trigger 20 as described further below.

As shown in FIGS. 8B and 9B, the distal portions of right and left handle halves 600 and 700 are formed with internal cylindrical recesses or sockets 612 and 712 that receive the laterally extending bosses 552 of collar 550 (FIG. 2). Internal grooves 611 and 711 are also formed within the distal portions of right and left handle halves 600 and 700 in which the c-clip 524, flat washer 520 and spring washer 522 (FIGS. 2 and 3A) are fitted.

As shown in FIGS. 8C and 9C, the right and left handle halves 600 and 700 are also provided with a series of laterally extending, perpendicular internal walls 628 and 728 that include slots and recesses for routing the fluid conduits or tubes 370 and 470, the cable 390 and the insulated wire conductors 360 and 460 that extend through the length of handle 10.

The trigger 20, thumb slide 25, and the associated link arm 26 and trigger lock 27 are shown assembled to the right handle half 600 in FIG. 10 with the trigger 20 in the released position and the thumb slide 25 in the unlocked distal or retracted position. The trigger lock 27 is shown in greater detail in FIGS. 11A-11B, the link arm 26 is shown in greater detail in FIGS. 12A-12B, and the trigger 20 is shown in isolation in FIGS. 13A-13B.

Trigger 20 is provided with laterally extending cylindrical pivot bosses 206, 206' that are mounted into sockets 723 and 623, respectively. When released, trigger 20 extends outward through downwardly opening recesses 621 and 721. When pulled, trigger 20 is pivoted inwardly into the handle recesses 621 and 721 about pivot bosses 206, 206' to apply tension to the cable 390 that draws the upper and lower jaws 35 and 45 together. Cable 390 is mounted within a lubricious tube 391, extending from the proximal wall 628 to the distal end 15 of the handle 10, to allow the cable 390 to move freely within the handle 10 when trigger 20 is pulled or released.

Trigger 20 is coupled to the proximal end of cable 390 through link arm 26, illustrated in isolation in FIGS. 12A and 12B. Link arm 26 is provided at a distal end with two laterally extending bosses 262 and 262' that are received in circular sockets 204 (one of which is shown in FIG. 13B) formed on the interior walls of the internal chamber 202 of trigger 20 to thereby pivotally mount the distal end of the link arm 26 to the trigger 20. Link arm 26 is formed with a longitudinally extending slot 266, allowing compression of the distal end of the link arm 26 to facilitate positioning of cylindrical bosses 262 and 262' within the corresponding sockets 204 within the trigger 20. As also shown in FIG. 13B, longitudinal slots 215 are provided in the interior 202 to assist insertion of the bosses 262, 262' on link arm 26 into sockets 204 in trigger 20 during assembly. Link arm 26 is provided at its proximal end with two laterally extending, circular bosses 264 and 264' that are received within the elongated slots 625 and 725, respectively, in the respective right and left handle halves 600 and 700. When trigger 20 is released, the circular bosses 264 and 264' are disposed at the distal ends of the opposed elongated slots 625 and 725, respectively. When trigger 20 is pulled inward, the proximal end of the link arm 26 is moved proximally within the opposed slots 625 and 725, applying tension to cable 390.

Cable 390 is coupled to the link arm 26 by means of a swaged retainer 24, mounted within a coil spring 28. Coil spring 28 is fitted within a generally cylindrical chamber 266 formed extending at 90 degrees to the proximal end of link arm 26. Cable 390 passes through an upwardly facing slot 270 in link arm 26 and through the interior of spring 28 to retainer 24. Spring 28 is normally extended within chamber 266 but is compressed to provide protection against over tensioning of the cable 390, if the upper and lower jaws 35 and 45 encounter significant resistance to further movement toward one another. The configuration of the trigger 20, link arm 26 and slots 625 and 725 provide a mechanism whereby, the cable 390 is pulled proximally relatively quickly during initial upward movement of the trigger 20 to facilitate initial rapid closing of the jaws 35 and 45. The cable 390 is pulled relatively more slowly during further upward movement of the trigger 20 to provide increased control to the physician during final compression of the jaws 35 and 45 against the tissue to be ablated.

Trigger 20 is also provided with a distally extending projection 208 terminating with a laterally extending, generally cylindrical, boss 210 shown best in FIG. 13B. As illustrated in FIG. 10, when the trigger 20 is released and in its most downward position (corresponding to the point of maximum jaw opening), the fluid conduits or tubes 370 and 470 are disposed side by side and compressed between cylindrical boss 210 and the inwardly extending projections 630 and 730. This compression of the fluid conduits or tubes 370 and 470 prevents flow of conductive fluid from the fluid source and out of the electrodes 330 and 430 and the electrode mounts 340 and 440 when the hemostat is not in use.

The trigger 20 is also formed with a laterally extending slot 212 having an array of teeth 214 formed along one side of the slot 212. A trigger lock mechanism is provided involving the interaction of the thumb slide 25 with the trigger 20 through a trigger lock 27 that is coupled at one end with the thumb slide 25 and selectively engages the teeth 214 to retain the upper and lower jaws 35 and 45 at a fixed position adjacent tissue to be ablated without requiring the physician to continually apply pressure to trigger 20. Distal or forward movement of the thumb slide 25 causes the trigger lock 27 to engage the teeth 214, and proximal or rearward movement of the thumb slide 25 releases the engagement. The trigger 20 can be operated freely by the physician to open or close the upper and lower jaws 35 and 45 when the thumb slide 25 is in the rearward position. With the thumb slide 25 in the forward position, the trigger 20 can be moved inward ratcheting over the teeth 214 to close the upper and lower jaws 35 and 45, but the trigger 20 will not move outward upon release by the physician.

The trigger lock 27 depicted in isolation in FIGS. 11A and 11B comprises an elongated link arm 275 having rods 272 and 278 laterally extending parallel to one another from opposed ends of the link arm 275. As shown in FIG. 10, the rod 272 is inserted through the slot 202 so that the link arm 275 extends alongside the trigger 20 within the recess 721. The rod 278 extends into a generally centrally located notch 252 of a resilient beam section 250 of the thumb slide 25. Cylindrical pivot bosses 276 and 276' extend laterally on either side of the link arm 275 in alignment with rod 272 and are inserted into sockets 724 and 624, respectively.

The rod 272 inserted through the slot 212 extending through the trigger 20 is formed with a laterally extending ramped tooth 274 that is selectively engagable with one of the ramped teeth 214 formed along the proximal edge of slot 212, when the trigger lock 27 is pivoted forward from the position illustrated in FIG. 10 by distal or forward movement of the thumb slide 25 by the physician. Movement of the trigger 20 inwardly into the handle recess with the trigger lock 27 advanced forward from the position illustrated in FIG. 10 causes the interaction of the tooth 274 on the trigger lock 27 with the teeth 214 to retain the trigger 20 in position when pressure is released. The oblong configuration of sockets 624 and 724 that receive bosses 276' and 276 of the trigger lock 27 allow the trigger lock 27 to move slightly forward during inward movement of the trigger 20 so that the tooth 276 on trigger lock 27 may ratchet along the ramped teeth 214 of trigger 20. Interaction of the teeth 214 with the ramped tooth 274 on the trigger lock 27 prevents outward movement of the trigger 20 as long as the thumb slide 25 remains in the forward position in the slot formed by openings 627 and 727.

Release of the trigger 20 is accomplished by proximal or rearward movement of thumb slide 25, pivoting the ramped tooth 274 out of engagement with a tooth of the teeth 214 along slot 212 which allows the upper and lower jaws 35 and 45 to open unless the physician holds the trigger 20 in position. The trigger 20 is urged outwardly out of the recess in handle 10 by spring 23 upon release of the trigger 20 and rearward movement of the thumb slide 25. When the trigger 20 reaches its full outward position, flow of conductive fluid through fluid conduits 370 and 470 is terminated as the tubing is compressed between the laterally extending boss 210 and the inwardly extending projections 630 and 730, as discussed above.

The thumb slide 25 is provided with a resilient beam section 250, having a generally centrally located notch 252 which engages the laterally extending rod 278 on trigger lock 27, coupling the thumb slide 25 to the trigger lock 27. The thumb slide 25 is preferentially retained at either the proximal, rearward or distal, forward point of its travel, without the necessity of the physician manually maintaining pressure on the thumb slide 25 due to the resilience of the beam 250 and the arcuate path of travel of the rod 278.

Figure 14:
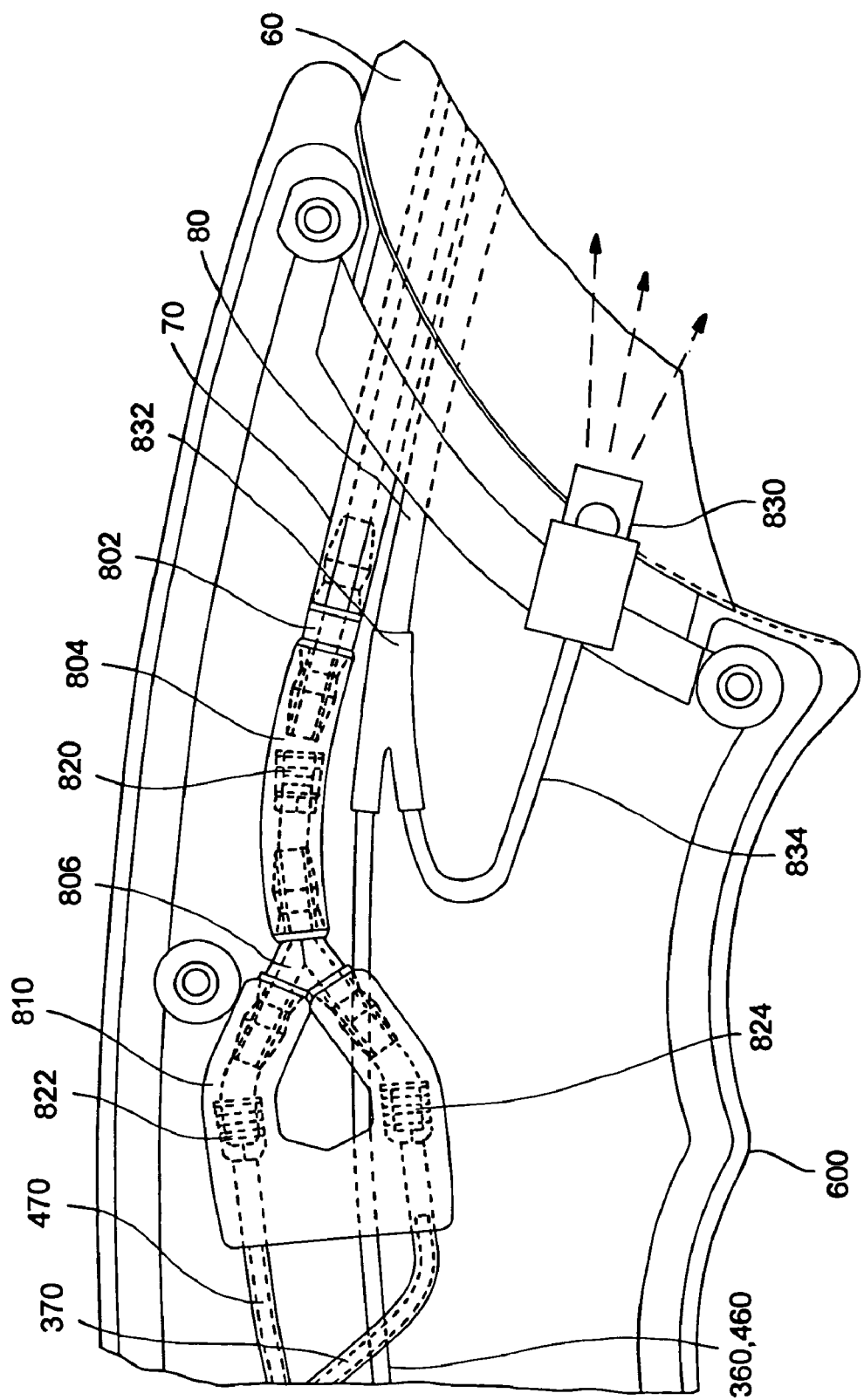
FIG. 14 is a cut-away view of the proximal portion of the hemostat of FIG. 1 with the left handle half removed.

FIG. 14 illustrates a proximal portion of the assembled hemostat of FIG. 1 with the left handle half 700 removed to show the multi-conductor cable 80 and fluid conduit 70 extending through the strain relief 60 and their joinder to the wire conductors 360, 460 and the fluid conduits 370, 470.

The distal end of the fluid conduit 80 is coupled through a fitting 802 to proximal end of flexible tubing 804. The distal end of flexible tubing 804 is coupled to the trunk of a Y-connector 806, and the distal legs of the Y connector 806 are coupled to arms of a D-connector 810. The D connector 810 is formed of a flexible plastic, e.g., silicone rubber, providing spaced apart fluid channels that are coupled to the proximal ends of the fluid conduits 370 and 470.

The fitting 804 supports a proximal flow controller or regulator 820 that has a precisely sized orifice that limits conductive fluid flow into the Y-connector 806. The flow regulator 820 establishes a fixed flow rate and pressure within the Y-connector 806 regardless of the pressure of the fluid source that is available in the surgical theatre. The flow rate is established depending upon the upper and lower electrode area and design.

The D connector 810 supports a pair of downstream flow regulators 822 and 824 that have equal, precisely sized orifices that further reduce the fluid flow rate and pressure of the conductive fluid entering the fluid conduits 370 and 470. The downstream flow regulators 822 and 824 ensure that an even flow of conductive fluid is provided from within the Y connector 806 into the fluid conduits 370 and 470. By this mechanism, the hemostat may be operated without the necessity of an associated pressurized fluid source and still provide controlled and even fluid flow to the upper and lower jaws 35 and 45 that contact the tissue to be ablated.

An optional light emitter, e.g., an LED 830, is depicted in FIG. 14 located within the strain relief 60 and coupled through an electrical junction 832 with the insulated wire conductors 360 and 460. The wire conductors 360 and 460 can take the form of a twisted wire cable that extends distally from the electrical junction 832 through the length of the handle to the swivel assembly 50 where they are separated as shown in FIGS. 3A and 4. Separate wire conductors within a cable 834 extend from the electrical junction 832 to the LED 830. In use, the LED 830 is illuminated in response to activation of an associated RF electrosurgical generator, and the LED illumination illuminates the strain relief 60, which is preferably fabricated of a translucent flexible material, such as silicone rubber or the like. The physician will typically hold the handle 10 in orientations that make the strain relief 60 visible, and illumination of the LED 830 indicates to the physician that RF energy is being applied to the electrodes The proximal portion of the handle 10 may also optionally carry other electronic components including circuitry containing calibration information, for example calibrating a thermocouple if provided to sense electrode or tissue temperature. Circuitry containing identification information or providing re-use prevention may also be included, however such features are not believed to be essential to or a part of the present invention.

FIGS. 15A and 15B illustrate an alternative embodiment of the electrode described above that can be employed in modified upper and lower jaw assemblies 30A and 40A corresponding generally to upper and lower jaw assemblies 30 and 40. The upper and lower jaw assemblies 30A, 40A have a malleable backbone 310, 410 and a sheath 320, 420 as described above that are attached to the respective upper and lower jaw mounts 300 and 400 as shown in FIGS. 2 and 3. However, electrode 330A, 430A incorporates an exposed elongated electrode extension 350A, 450A extending to the outer surface of porous electrode support 340A, 440A and along the jaw 35, 45 that is intended to directly contact the tissue to be ablated. In this embodiment, conductive fluid is delivered as described above into the lumen of the internal tubular electrode 330A, 430A, which may be substantially the same as the tubular electrodes 330, 430. An elongated electrode surface 352A, 452A of the electrode extension 350A, 450A and the contacted tissue are irrigated by conductive fluid emitted through the fluid ports of the internal tubular electrode 330A, 430A and conducted through the pores of the electrode support 340A, 440A.

The electrode extension 350A, 450A is depicted prior to assembly with the electrode support 340A, 440A and the elongated tubular electrode 330A, 430A in FIGS. 16A and 16B. As formed, the electrode extension 350A, 450A includes an elongated straight portion 352A, 452A that is mounted against the exposed to the exterior of the electrode support 340A, 440A. A distally extending portion 360A, 460A is adapted to be inserted into the lumen of the electrode support 340A, 440A to extend alongside the elongated tubular electrode 330A 430A as shown in FIG. 15B.

A series of barbed projections 354A, 454A extend laterally away from the elongated straight portion 352A, 452A. The electrode extension 350A, 450A is adapted to be bent back at junction 356A, 456A to enable insertion of the series of barbed projections 358A, 458A into the electrode support 340A, 440A. The proximal end 362A, 462A is electrically connected to the proximal ends of the tubular electrodes 330A, 430A and the distal ends of the wire conductors 360, 460.

This alternative exposed electrode embodiment can be formed by modifying the tubular electrode 330, 430 to have a conductive electrode band extending from the tubular electrode along the surface of the electrode support 340, 440.

Alternatively, this alternative electrode design can be accomplished without use of the tubular electrode 330, 430, whereby conductive fluid is delivered to a lumen of the electrode support 340, 440 or to a fluid channel between the electrode support 340, 440 and the sheath 320, 420, and the exposed electrode band is supported by the electrode support 340, 440.

Figure 17:
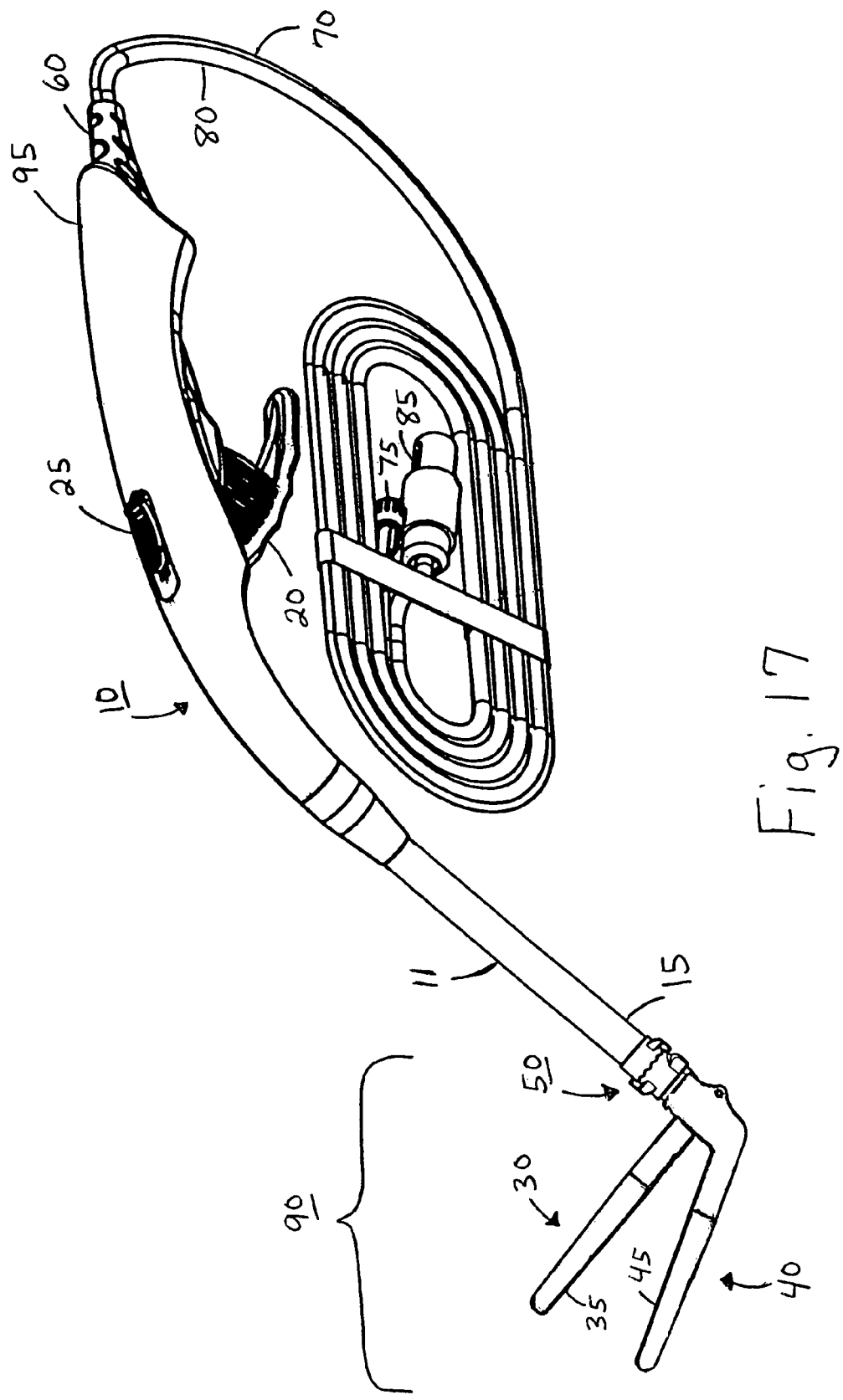
FIG. 17 is a view of an assembled hemostat according to one embodiment of the present invention.

In reference to FIG. 17, one embodiment of the hemostat of the present invention generally comprises an elongated handle assembly or handle 10 having a jaw assembly 90 mounted at handle distal end 15, a trigger 20 intermediate the handle proximal and distal ends 95 and 15, and a strain relief 60 located at handle proximal end 95. An elongated cable is coupled to the strain relief 60 and comprises a fluid conduit 70 extending to a proximal fluid fitting 75 adapted to be coupled to a source of conductive fluid and a multi-conductor electrical cable 80 extending to a proximal electrical connector 85 adapted to be coupled to an electrosurgical unit. The trigger 20 is employed to move the jaws of the first or lower jaw assembly 40 with respect to the second or upper jaw assembly 30 of the jaw assembly 90 together to compress tissue therebetween to allow for creation of a linear RF ablation by electrically conductive fluid emitted from electrodes and contacting tissue or direct contact of the electrodes located along the upper and lower jaws 35 and 45.

The jaw assembly 90 includes an upper jaw assembly 30, a lower jaw assembly 40, and a swivel assembly 50, discussed in more detail below. The upper jaw and lower jaw assemblies 30 and 40 have opposed upper and lower jaws 35 and 45, respectively, each comprising a fluid assisted elongated electrode assembly. The upper and lower jaw assemblies 30 and 40 support elongated electrodes, discussed in more detail below, each coupled to one of the insulated conductors within conduit 80 extending proximately through the strain relief 60 to electrical connector 85. Each of the jaws 35 and 40 of respective upper and lower jaw assemblies 30 and 40 also may be coupled to fluid conduit 70 enabling delivery of saline or other conductive fluid from a source coupled to fitting 75 along the lengths of the opposed jaws 35 and 45.

The swivel assembly 50, provides the physician with the opportunity to position the jaw assembly 90 in a variety of orientations relative to the handle 10, to facilitate placing the 35 and 45 jaws against tissue to form desired lines of lesions, e.g., the heart wall in performance of the above-described Maze procedure. In one embodiment, the physician may manually grasp and rotate the swivel assembly 50 and the jaw assembly 90 to provide a roll adjustment R, preferably through an arc of at least 300 degrees, relative to the axis of the distal end 15 of the handle 10 through interaction of components of the handle and swivel assembly described further below. Moreover, the upper and lower jaws 35 and 45 may be rigid in a straight or curved configuration or the upper and lower jaws 35 and 45 may be malleable as described further below. The combination of these features make the hemostat highly versatile in use.

In one embodiment, the trigger 20 is employed to open (separate apart) and close (draw together) the jaws 35 and 45 and to compress tissue between the jaws 35 and 45 prior to application of RF energy to create an elongated lesion. A thumb slide 25 may be provided in conjunction with an internal trigger lock, allowing the position of the trigger 20 and the jaws 35, 45 to be locked. After the trigger 20 is drawn toward the handle 10 to close the jaws 35 and 45, the thumb slide 25 is moved distally relative to the handle 10 to cause an internal trigger lock to engage one of a series of ratcheting lock points that define a set of locking locations for the jaws 35, 45, as described further below. Movement of the thumb slide 25 proximally relative to the handle 10 releases the trigger 20 and the jaw assembly 90, allowing the jaws 35, 45 to return to a fully open position. The interaction of the trigger 20, thumb slide 25 and the associated trigger lock mechanism frees the physician from the need to maintain pressure on the trigger 20 to compress tissue between the jaws 35, 45 during the ablation, simplifying operation of the hemostat.

Figure 18:
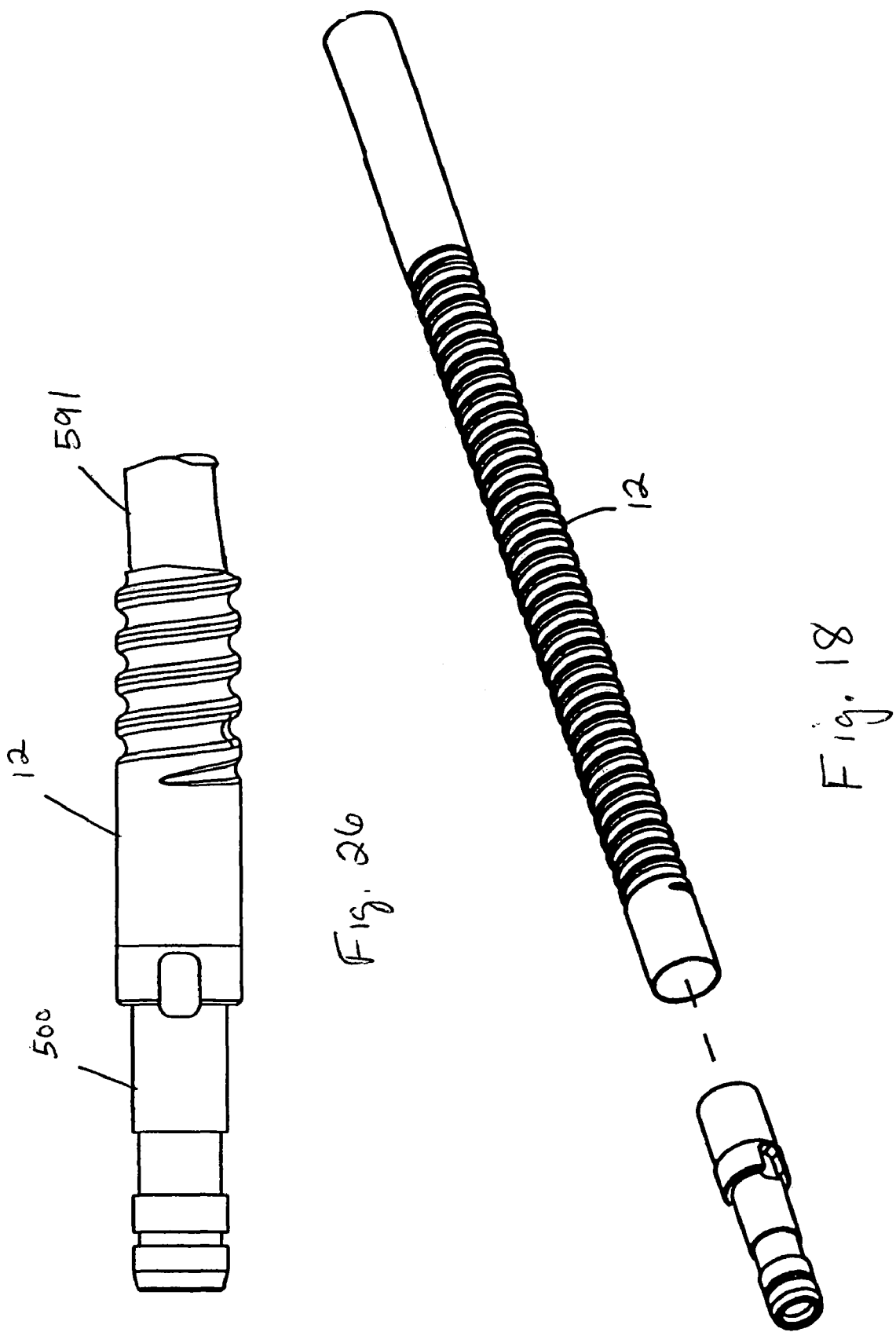
FIG. 18 is a view of a portion of a hemostat according to one embodiment of the present invention.

The handle 10 may include an elongated shaft portion 11 proximal the handle distal end 15. One or more portions of elongated shaft 11 may be straight, curved, rigid and/or malleable. For example, as shown in FIG. 18, elongated shaft 11 may comprise a malleable corrugated tube member 12, thereby providing the physician with the opportunity to manually position the jaw assembly 90 in a variety of orientations, relative to the distal portion of handle 10, to facilitate placing the 35 and 45 jaws against tissue to form desired lines of lesions. For example, the physician may manually grasp and bend or shape malleable corrugated tube member 12 to adjust the orientation of jaw assembly 90 relative to the distal portion of handle 10. Elongated shaft member 11 may comprise one or more lumens or a multi-lumen member, e.g., a multi-lumen plastic tube, may be placed within elongated shaft member 11. One or more portions of elongated member 11 may comprise one or more cross sectional shapes, e.g., round, oval, triangular, rectangular or square. The cross sectional area of elongated member 11 may very along its length. For example, elongated member may comprise ridges and grooves. Elongated member 11 may comprise one or more materials, e.g. plastic materials, metal materials, rigid materials, malleable materials, etc. For example, one or more portions of elongated member 11 may comprise malleable stainless steel. One or more portions of elongated member 11 may be covered, for example with a sheath material such as a plastic material.

Figure 19:
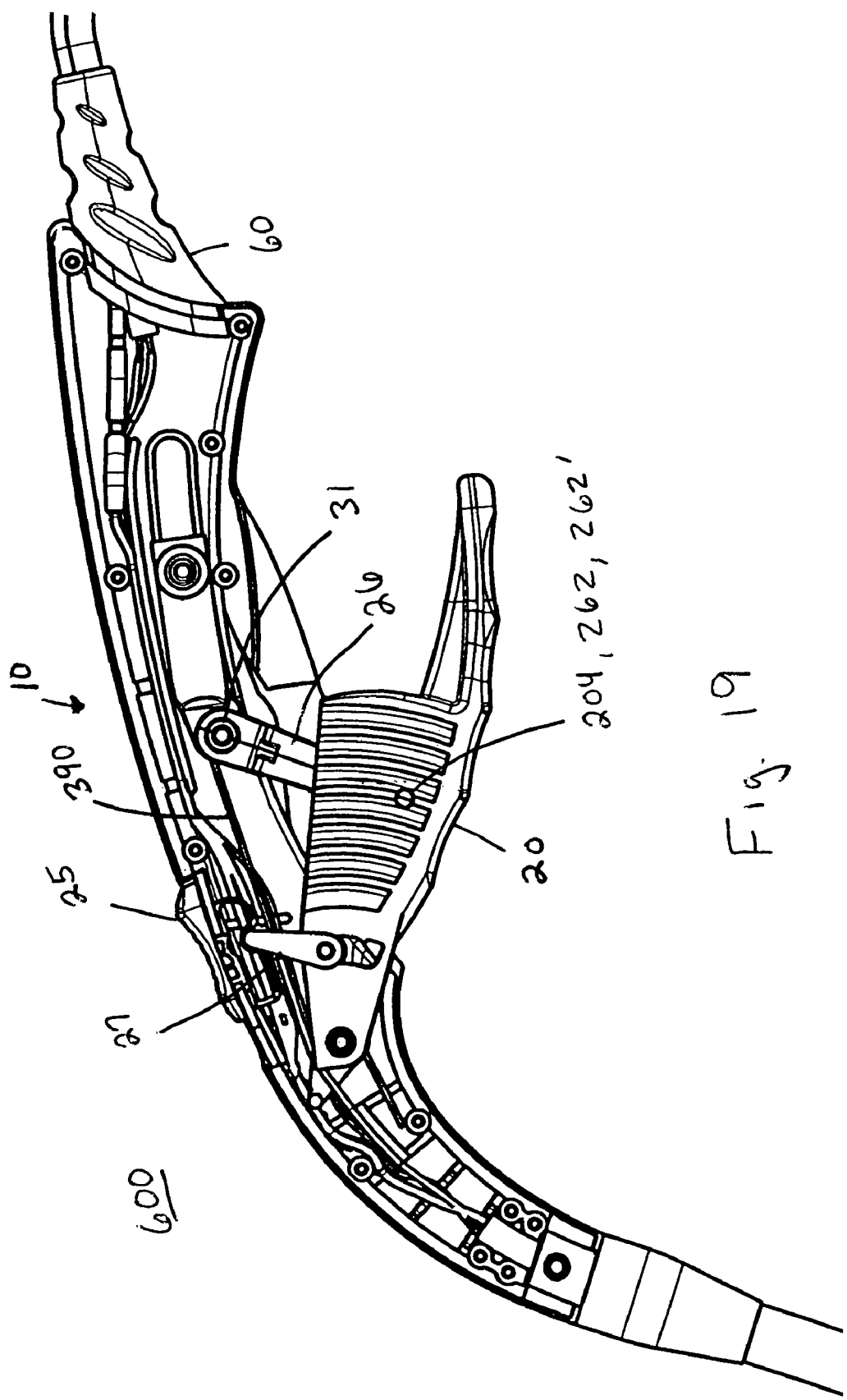
FIG. 19 is a cross-section view taken of a portion of the right handle half of one embodiment of the present invention.

As shown in FIG. 19, trigger 20 is mounted to handle 10 to pivot inward to apply tension on cable 390 or outward to release tension on cable 390. Upward openings in respective right and left handle halves receive the thumb slide 25. The trigger 20, thumb slide 25, and the associated link arm 26 and trigger lock 27 of one embodiment of the invention are shown assembled to the right handle half 600 in FIG. 19 with the trigger 20 in the released position and the thumb slide 25 in the unlocked distal or retracted position. The trigger 20, thumb slide 25, and trigger lock 27 are shown in greater detail in FIG. 20, a portion of link arm 26 is shown in greater detail in FIG. 21.

Trigger 20 is provided with laterally extending cylindrical pivot bosses that are mounted into sockets, respectively. When released, trigger 20 extends outward through downwardly opening recesses. When pulled, trigger 20 is pivoted inwardly into the handle recesses about the pivot bosses to apply tension to the cable 390 that draws the upper and lower jaws 35 and 45 together. Cable 390 is mounted to move freely within the handle 10 when trigger 20 is pulled or released.

Figure 21:
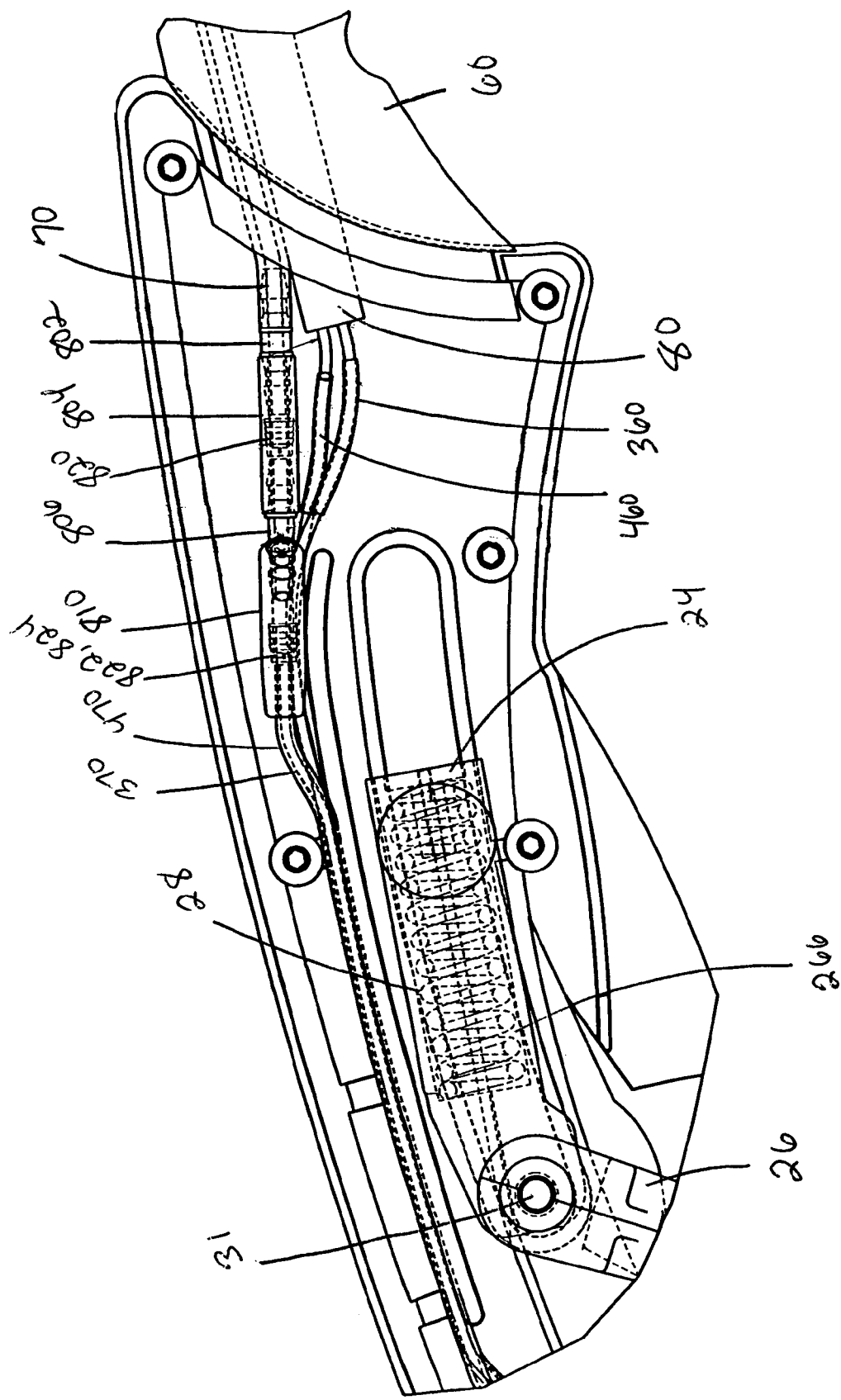
FIG. 21 is a cross-section view taken of a portion of the right handle half of one embodiment of the present invention.

Trigger 20 is coupled to the proximal end of cable 390 through link arm 26, illustrated in FIGS. 19 and 21. Link arm 26 is provided at a distal end with two laterally extending bosses 262 and 262' that are received in circular sockets 204 formed on the interior walls of the internal chamber of trigger 20 to thereby pivotally mount the distal end of the link arm 26 to the trigger 20. When trigger 20 is pulled inward, the proximal end of the link arm 26 is moved proximally thereby applying tension to cable 390.

Cable 390 is coupled to the link arm 26 by means of a swaged retainer 24, mounted within a coil spring 28. Coil spring 28 is fitted within a generally cylindrical chamber or spring cage 266 pivotally coupled at 31 to the proximal end of link arm 26. Cable 390 passes through the interior of spring 28 to retainer 24. Spring 28 is normally extended within chamber 266 but is compressed to provide protection against over tensioning of the cable 390, if the upper and lower jaws 35 and 45 encounter significant resistance to further movement toward one another.

Figure 20:
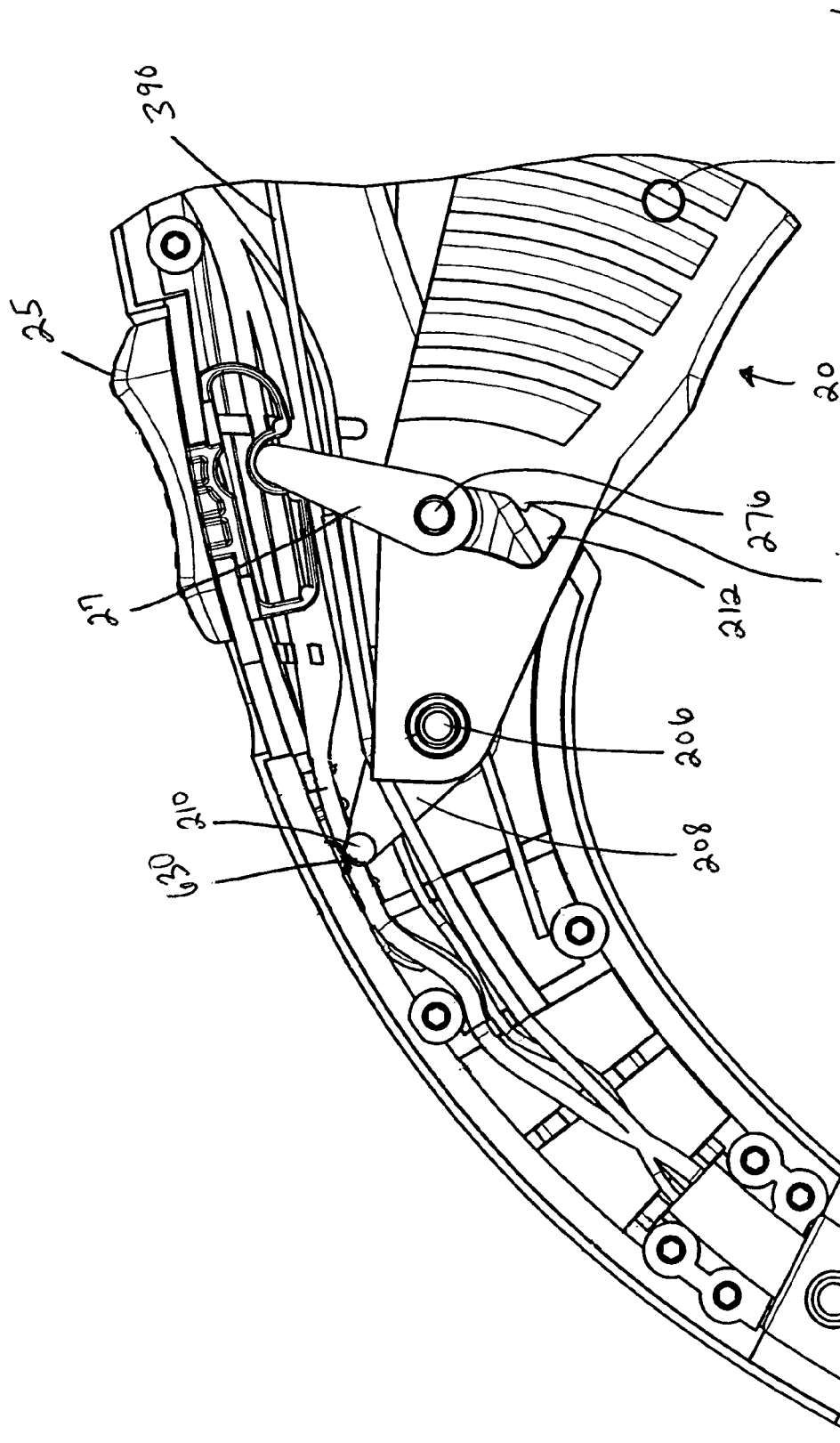
FIG. 20 is a cross-section view taken of a portion of the right handle half of one embodiment of the present invention.

Trigger 20 is also provided with a distally extending projection 208 terminating with a laterally extending, generally cylindrical, boss 210 as shown in FIG. 20. As illustrated in FIG. 20, when the trigger 20 is released and in its most downward position (corresponding to the point of maximum jaw opening), the fluid conduits are compressed between cylindrical boss 210 and the inwardly extending projections 630. This compression of the fluid conduits prevents flow of conductive fluid from the fluid source and out of the electrodes when the hemostat is not in use.

The trigger 20 is also formed with a laterally extending slot 212 which may have an array of teeth formed along one side of the slot 212. A trigger lock mechanism may be provided involving the interaction of the thumb slide 25 with the trigger 20 through a trigger lock 27 that is coupled at one end with the thumb slide 25 and may selectively engage the teeth 214 to retain the upper and lower jaws 35 and 45 at a fixed position adjacent tissue to be ablated without requiring the physician to continually apply pressure to trigger 20. Distal or forward movement of the thumb slide 25 causes the trigger lock 27 to engage the teeth 214, and proximal or rearward movement of the thumb slide 25 releases the engagement. The trigger 20 can be operated freely by the physician to open or close the upper and lower jaws 35 and 45 when the thumb slide 25 is in the rearward position. With the thumb slide 25 in the forward position, the trigger 20 can be moved inward ratcheting over the teeth 214 to close the upper and lower jaws 35 and 45, but the trigger 20 will not move outward upon release by the physician. Release of the trigger 20 is accomplished by proximal or rearward movement of thumb slide 25.

FIG. 21 illustrates a proximal portion of the assembled hemostat of FIG. 17 with the left handle half removed to show the multi-conductor cable 80 and fluid conduit 70 extending through the strain relief 60. The distal end of the fluid conduit 80 is coupled through a fitting 802 to proximal end of flexible tubing 804. The distal end of flexible tubing 804 is coupled to the trunk of a Y-connector 806, and the distal legs of the Y connector 806 are coupled to arms of a D-connector 810. The D connector 810 is formed of a flexible plastic, e.g., silicone rubber, providing spaced apart fluid channels that are coupled to the proximal ends of the fluid conduits 370 and 470.

The fitting 804 supports a proximal flow controller or regulator 820 that has a precisely sized orifice that limits conductive fluid flow into the Y-connector 806. The flow regulator 820 establishes a fixed flow rate and pressure within the Y-connector 806 regardless of the pressure of the fluid source that is available in the surgical theatre. The flow rate is established depending upon the upper and lower electrode area and design.

The D connector 810 supports a pair of downstream flow regulators 822 and 824 that have equal, precisely sized orifices that further reduce the fluid flow rate and pressure of the conductive fluid entering the fluid conduits 370 and 470. The downstream flow regulators 822 and 824 ensure that an even flow of conductive fluid is provided from within the Y connector 806 into the fluid conduits 370 and 470. By this mechanism, the hemostat may be operated without the necessity of an associated pressurized fluid source and still provide controlled and even fluid flow to the upper and lower jaws 35 and 45 that contact the tissue to be ablated.

Figure 22:
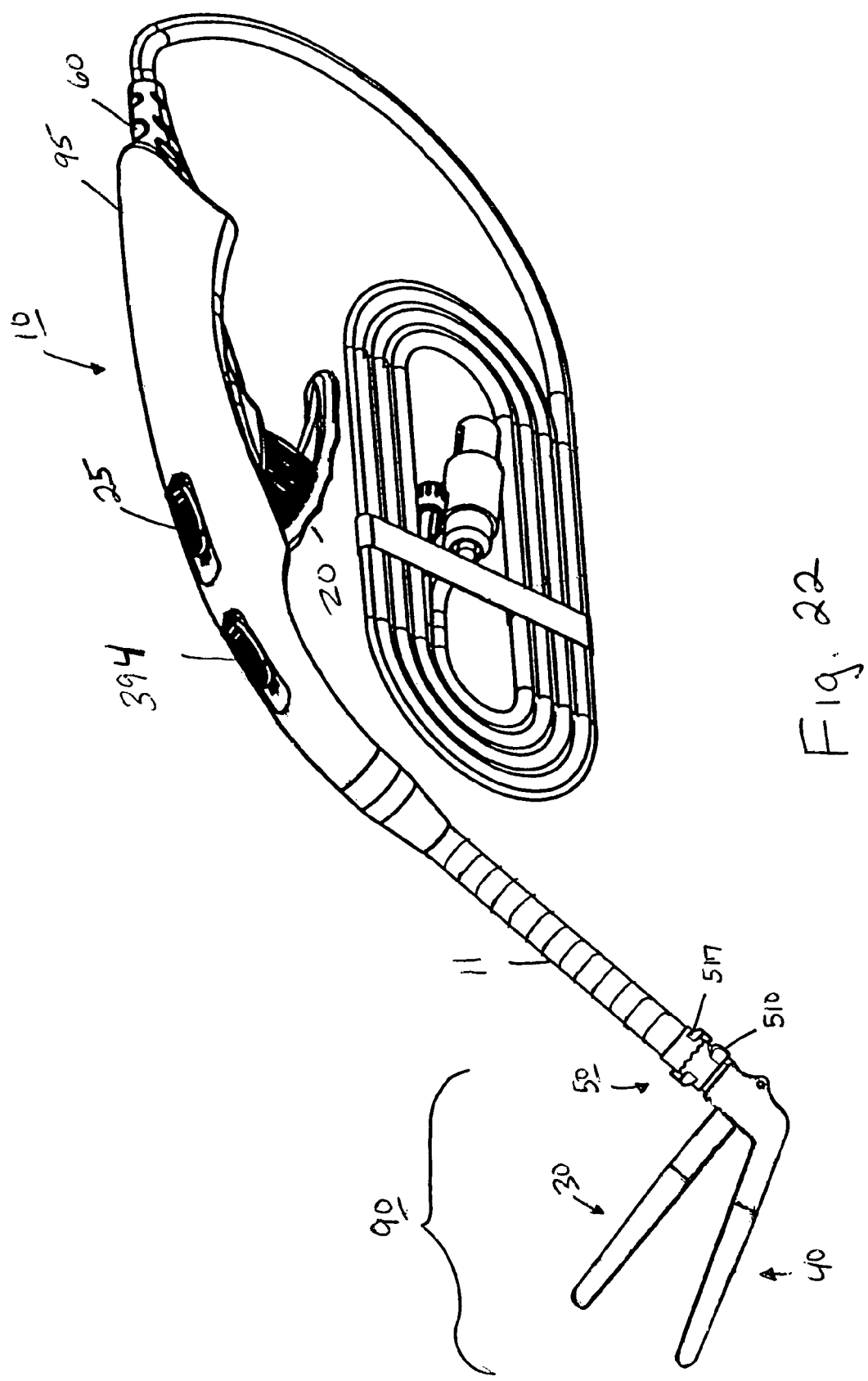
FIG. 22 is a view of an assembled hemostat according to one embodiment of the present invention.
Figure 23:
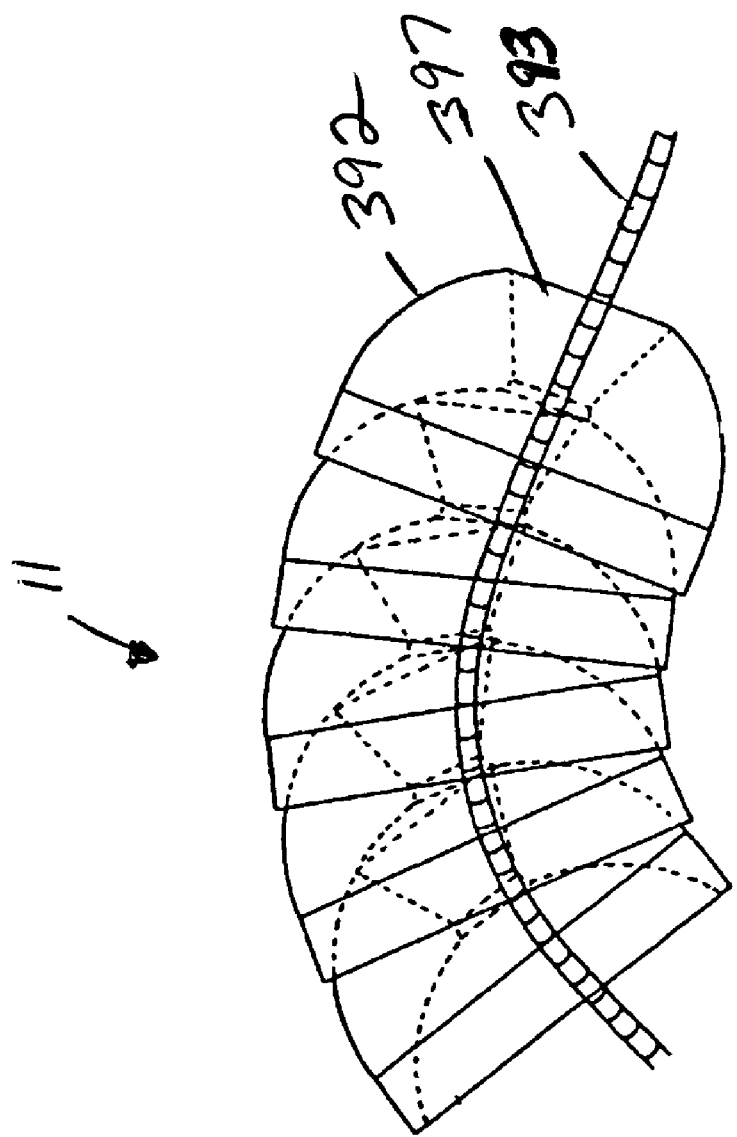
FIG. 23 is a view of a portion of the hemostat according to one embodiment of the present invention.

In reference to FIG. 22, elongated shaft portion 11 may comprise an articulating portion in one embodiment of the invention. As shown in FIG. 23, articulating shaft 11 may comprise a plurality of "ball and socket" links, for example. FIG. 23 is a partial view of a section of links 392 and cable 393. Each link may have a hole 397 that passes through it center. Each link may comprise, on its distal end, a hemispherical protrusion, and on its proximal end, a hemispherical indentation. The hemispherical shapes of adjacent links may be nearly identical, such that the links rotate smoothly against one another provided they are not under undue tension with each other. FIG. 23 shows the engagement of the cable 393 with the side wall of the links as the arm is bent. Cable 393 passes through hole of all the links and is connected between the distal end of handle 10 and the tightening mechanism 394. Tightening mechanism 394 may comprise a thumb slide thereby allowing a physician to tighten and loosen cable 393 by moving a mechanism proximally and distally, for example. Alternatively, tightening mechanism 394 may comprise a screw or handle mechanism that allows cable 393 to be tighten and loosened via a rotation motion. Alternatively, other types of tightening mechanisms may be used to tighten and loosen cable 393 thereby locking and unlocking the articulating section of handle 10. Tightening of the cable 393 causes the links to hold against each other in place. Immobilization of the links relative to each other during tightening of the cable is facilitated by the shape of the hole 397. As seen hole 397 is flared, having a larger opening with the surface of the hemispherical protrusion and a smaller opening through the surface of the hemispherical indentation. The links may very along the length of elongate member 11. The links may comprise one or more plastics and/or metals. For example, the links may be fabricated out of highly rigid engineered thermoplastics such as glass filled Ultem™. The cable may be a multi-stranded stainless steel cable. The links and cable may also be manufactured from other materials, including any other suitable highly engineered polymers or plastics including any number of liquid crystal polymers for the links, as well as many other types of cables, including bundle stranded, braided or cabled titanium as well as Kevlar™ for the cable.

A textured surface molded or otherwise formed into the hemispherical features of the links may be employed to increase the friction between adjacent surfaces when the links are pulled together. Alternatively, texture may be provided through a symmetrical structure, such as a series of interlocking dimples and hemispheres. Other geometries may also be used, including both surfaces having the same elements, such as hemispheres, as well as other shapes, including notches or grooves, for example.

Figure 24:
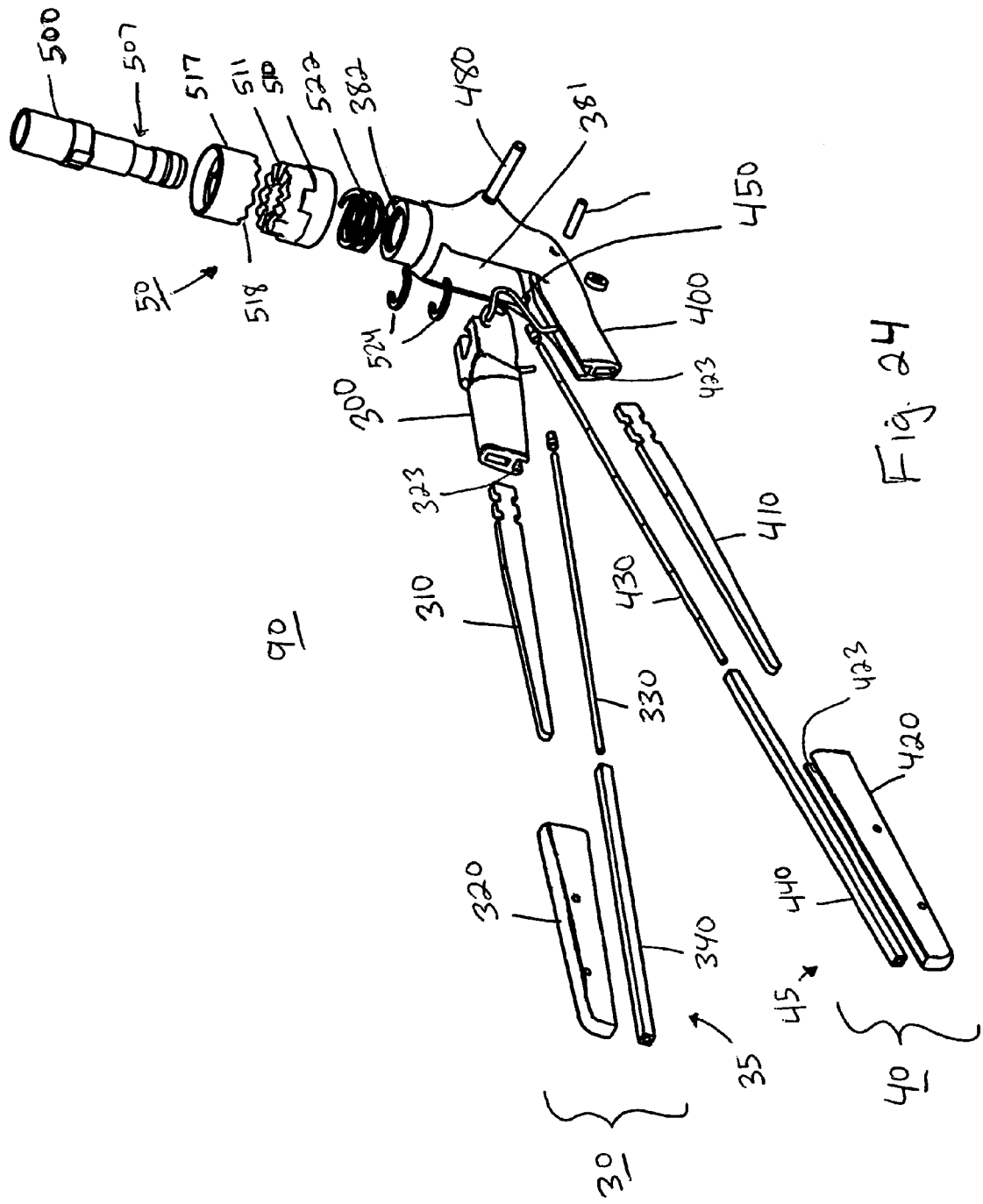
FIG. 24 is an exploded view of a jaw assembly of one embodiment of the present invention.

Referring to FIG. 24, the upper jaw assembly 30, in one embodiment of the invention, includes a pivotable, relatively rigid, upper jaw mount 300, an elongated backbone 310, an elongated insulated electrode sheath 320, an elongated conductive electrode 330, and an elongated electrode support 340. Upper jaw mount 300 may be fabricated of plastic or other insulated material, and in preferred embodiments may be fabricated of Teflon filled polycarbonate plastic. Backbone 310 is preferably fabricated of malleable stainless steel or other malleable metal and is attached at a proximal end to upper jaw mount 300. An insulated electrode sheath 320 is fitted over spine 310 with its proximal end located adjacent upper jaw mount 300. The elongated conductive electrode 330 comprises a length of malleable conductive metal tubing fitted into a lumen of the elongated electrode support 340. The insulated electrode sheath 320 is formed with a channel that receives the sub-assembly of the elongated conductive electrode 330 and electrode support 340 disposed along the jaw 35. Electrode sheath 320 may be fabricated of a flexible, electrically insulating, material, for example, silicone rubber or PVC. Elongated electrode support 340 is preferably fabricated of a porous material, such as Porex™ plastic, allowing for conductive fluid infiltration through its sidewall along its length and correspondingly delivery of conductive fluid along the length of jaw 35. The jaw 35 can therefore be bent laterally with respect to the upper jaw mount 300 to form a curve along the length thereof.

The lower jaw assembly 40 also includes a relatively rigid, lower jaw mount 400, an elongated backbone 410, an elongated insulated electrode sheath 420, an elongated conductive electrode 430, and an elongated electrode support 440 that are all formed of the same materials as the corresponding elements of the upper jaw assembly 30.

The jaw 45 can therefore also be bent laterally with respect to the lower jaw mount 400 to form a curve along the length thereof. In use, the physician may manually form a lateral curve in both the upper and lower jaws 35 and 45 to fit the contour of the tissue, e.g., the heart wall, to be ablated.

The lower jaw mount 400 is formed with an opening 381 for receiving the proximal end of upper jaw mount 300. When assembled, a proximal portion of the upper jaw mount 300 is fitted within the opening 381. A pin 480 extends through aligned holes through the proximal portion of upper jaw mount 300 and the lower jaw mount 400. The ends of pin 480 are fixed to the lower jaw 400 thereby allowing the proximal portion of the upper jaw mount 300 to be rotated about the pin 480, thereby allowing jaws 35 and 45 to open and close. A spring 450 urges the upper and lower jaws 35 and 45 apart from one another, facilitating opening of the jaws 35 and 45 upon release of the trigger 20 after application of RF energy.

Figure 25:
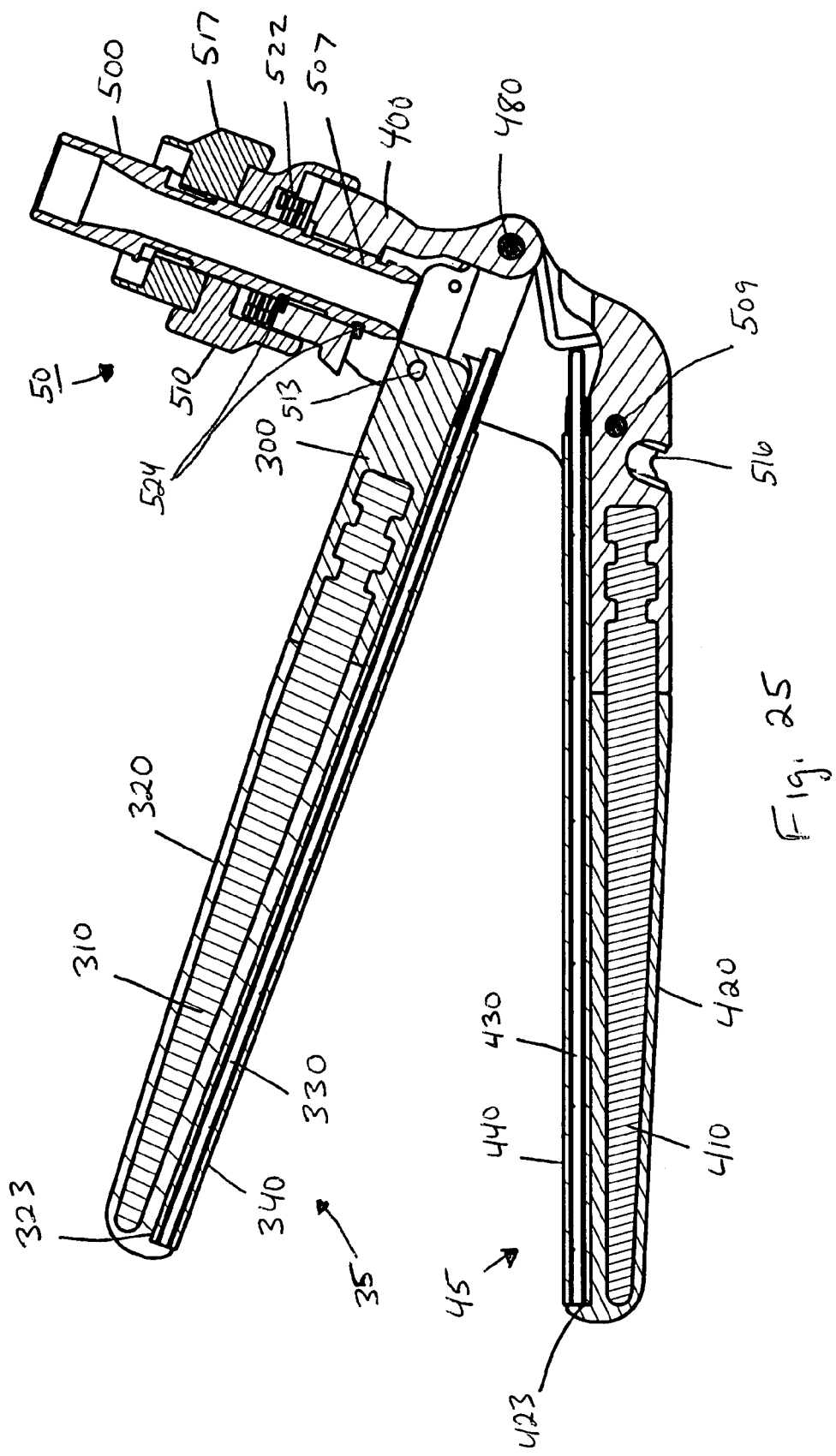
FIG. 25 is a cross-section view through the jaw assembly of one embodiment of the present invention.

As shown in FIGS. 24 and 25, the swivel assembly 50 includes a swivel 500 that may be fabricated of Teflon filled polycarbonate plastic to have a tubular structure. The jaw assembly 90 is mounted to the swivel assembly 50 by fitting the distal end of swivel 500 into collar 382 of lower jaw mount 400. The upper jaw mount 300 is mounted to the lower jaw mount 400 by pin 480 as described above, and the lower jaw mount is 400 rotatably mounted relative to the swivel 500. Therefore, the upper and lower jaw assemblies 30 and 40 may be rotated together relative to the swivel 500, allowing for movement of the jaws 35 and 45 together to be rotated around the axis of the distal end 15 of the handle 10 to a desired roll adjustment R to facilitate positioning the jaws 35 and 45 for creation of elongated lesions. The distal portion 507 of swivel 500 is rotatably mounted within collar 382 of lower jaw mount 400.

Figure 29:
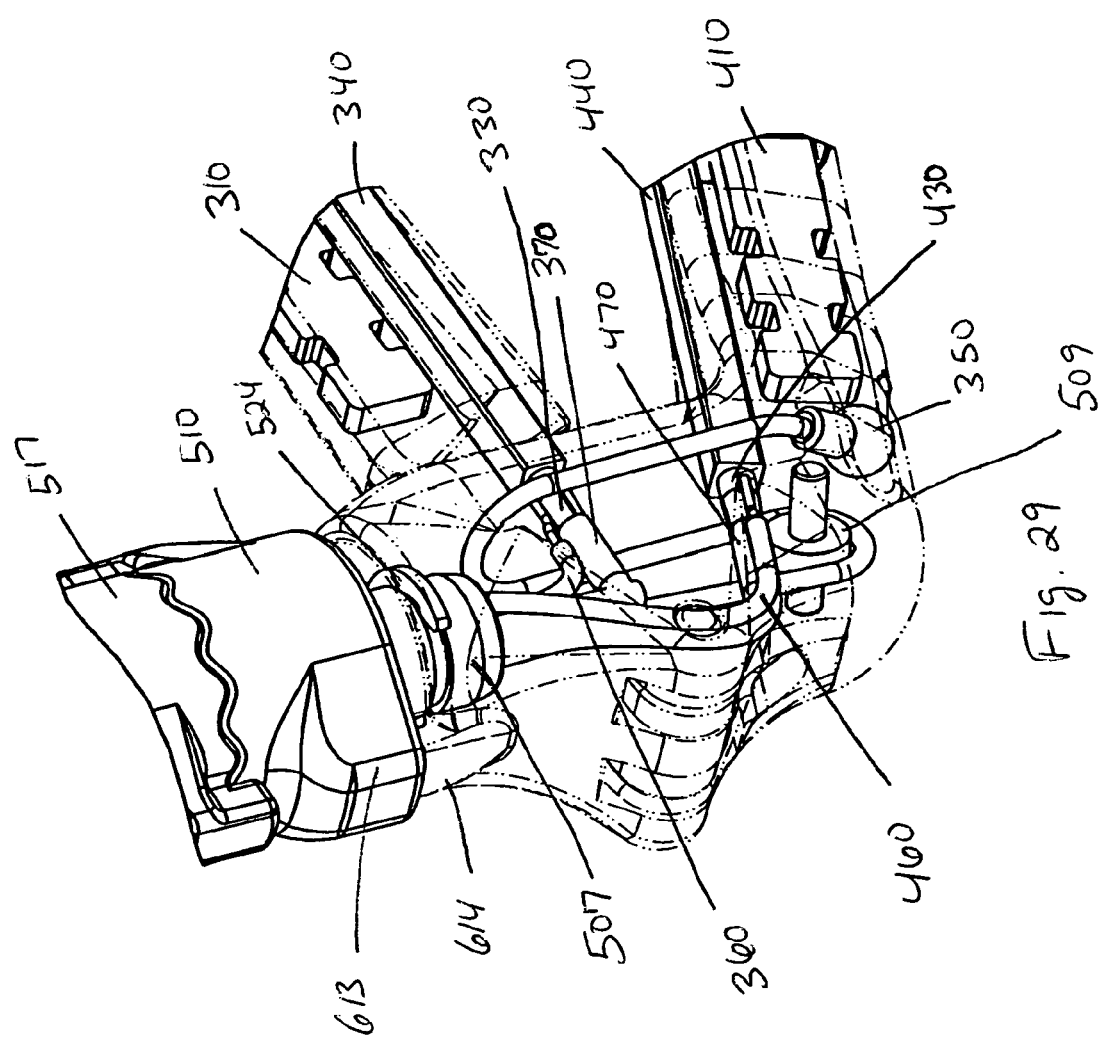
FIG. 29 is a view of a portion of the jaw assembly of one embodiment of the present invention.

A washer-shaped member 510 having a wavy or sinusoidal proximally facing surface 511 is fitted over the elongated distal portion 507 of swivel 500 and attached to the lower jaw mount 400. C-clips 524 mounted in a circumferential grooves formed in the distal portion 507 of swivel 500 maintain the distal portion 507 within the lumen of collar 382. Washer-shaped member 510 is prevented from rotating relative to lower jaw mount 400 through notch 613, engaging corresponding boss 614 formed on lower jaw mount 400 as shown in FIG. 29. A washer-shaped member 517 having a wavy or sinusoidal distally facing surface 518 is fitted over the elongated distal portion 507 of swivel 500 and attached to the distal end 15 of handle 10. Washer-shaped member 517 is prevented from rotating relative to swivel 500 through a notch engaging a corresponding boss of member 517 and swivel 500. A spring washer 522 is interposed between the proximal end of collar 382 and the washer-shaped member 510. Spring washer 522 urges the wavy or sinusoidal surfaces of washer-shaped members 510 and 517 against one another, whereby a plurality of detent locations are defined that maintain a selected roll R adjustment relative to the distal end 15 of the handle 10. In use, the physician may adjust the roll R of the jaw assembly 90 by simply turning the swivel assembly 50 relative to the handle 10. The detent mechanism maintains the swivel assembly 50 in the selected desired roll R adjustment prior to and during closure of the jaws 35 and 45 to compress tissue during application of RF energy.

Figure 27:
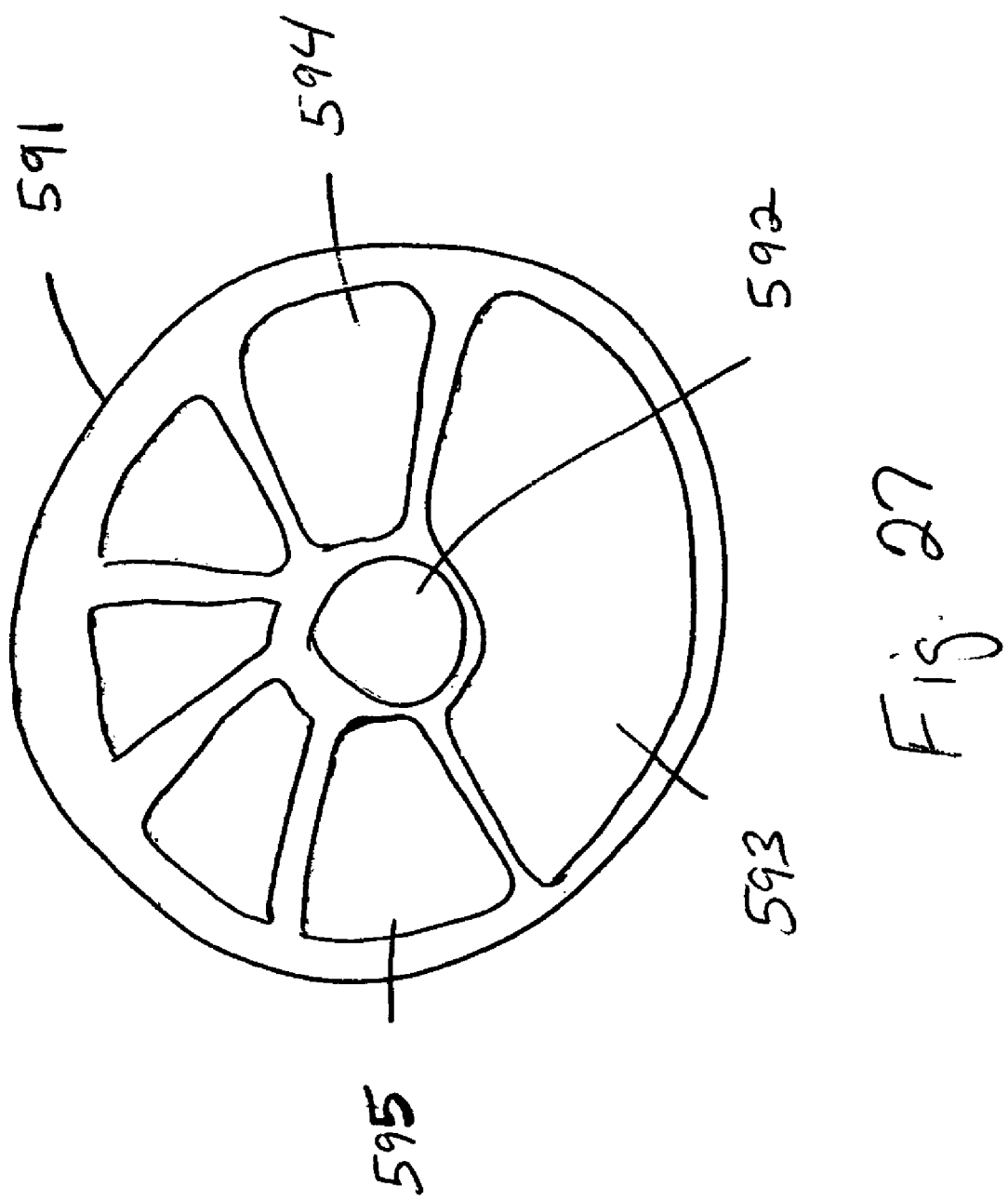
FIG. 27 is a cross-section view of a portion of the hemostat according to one embodiment of the present invention.

As shown in FIG. 26, in one embodiment of the invention, elongated malleable member 12 may be coupled to swivel member 500. Plastic tube 591 may reside within the lumen of elongated member 12. Plastic tube 591 may be made of a Pebax™ plastic material. As shown in FIG. 27, plastic tube 591 may comprise multiple lumens. In one embodiment of the invention, cable 390 passes through the center lumen 592 of tube 591. Insulated conductors 360 and 460 pass through lumen 593 whereas fluid conduits 370 and 470 pass through lumens 594 and 595, respectively. Tube 591 may be made of material that allows cable 390 to move or slide easily back and forth within lumen 593. A lubricant may be used to reduce friction between lumen 593 and cable 390.

Figure 28:
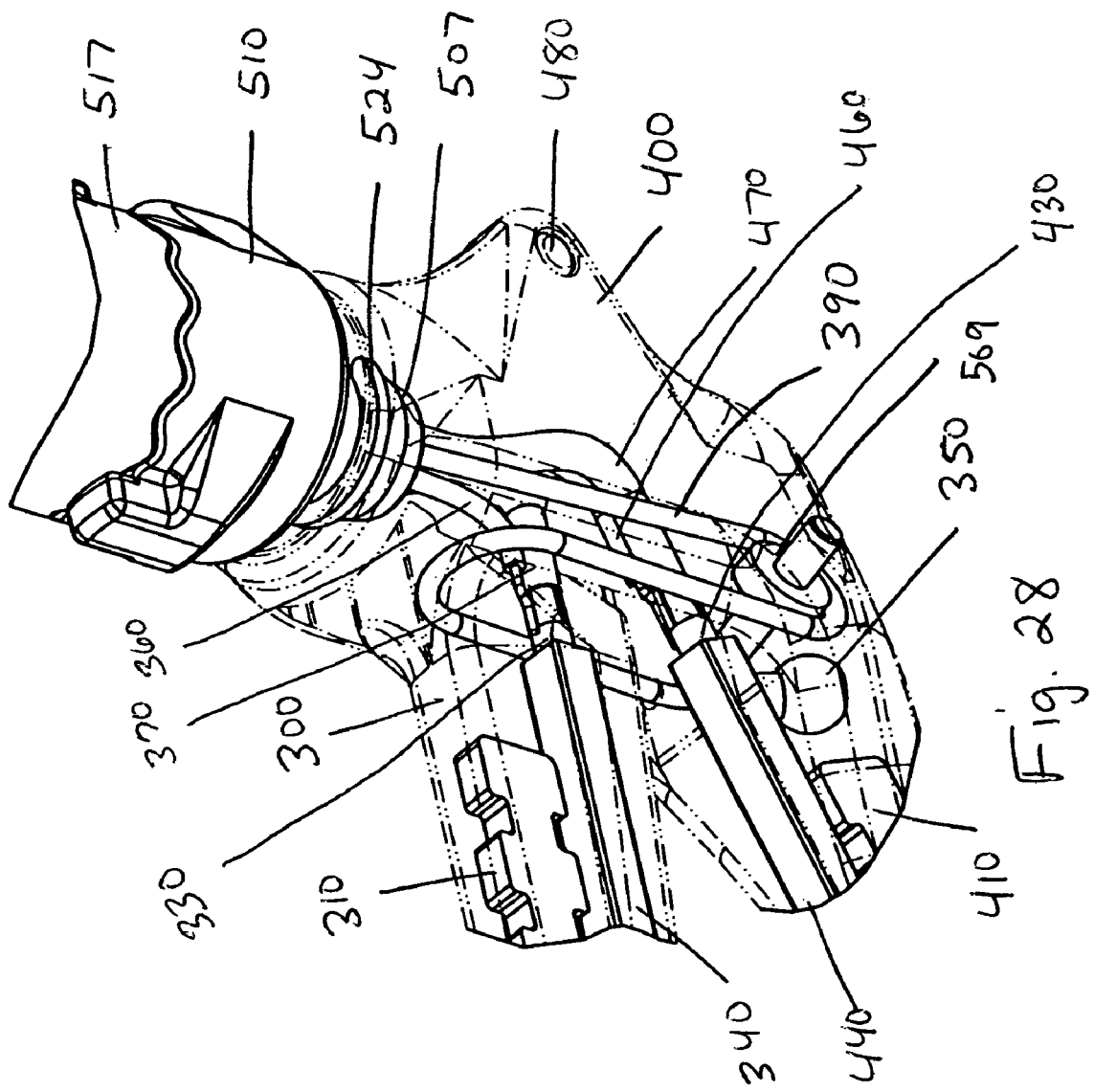
FIG. 28 is a view of a portion of the jaw assembly of one embodiment of the present invention.

The distal end of cable 390 is shown in FIGS. 28 and 29. Cable 390 extends from the trigger 20 and is employed to open and close the jaws 35 and 45. Cable 390 passes through the internal lumen of distal swivel portion 507, around pulley 509 comprising a roller and a pin in lower jaw mount 400, then upward through channel 513 (shown in FIG. 25) of upper jaw mount 300, and then back downward through bore 516 (shown in FIG. 25) in lower jaw 400. The distal end of the cable 390 is maintained within bore 516 by ball 350. When the cable 390 is tensioned by squeezing trigger 25, cable 390 is pulled through channel 513 and around pulley 509, thereby pulling upper jaw 35 toward lower jaw 45, allowing for compression of tissue therebetween. It should be noted that during this operation, the lower jaw mount 400 remains fixed relative to the swivel assembly 50 and only upper jaw mount 300 moves relative to the swivel assembly 50 or the handle 10. Proximal movement of cable 390 does not affect the position of the lower jaw 45 relative to the handle 10, nor does it affect the selected roll R adjustment of swivel 500. Rotation of the jaw assembly 90 and swivel 500 about the roll axis does not affect the operation of the cable 390 because the cable 390 passes through the swivel 500 and enters the jaw assembly 90 along the roll axis.

FIGS. 28 and 29 also show internal electrical wiring and fluid delivery conduits of this embodiment of the invention including, insulated conductors 360 and 460 and fluid conduits 370 and 470 that both terminate at connections with the proximal ends of the upper and lower electrodes 330 and 430, respectively. The fluid conduits 370 and 470 deliver conductive fluid into the lumens of the tubular upper and lower electrodes 330 and 430, respectively.

In one embodiment of the invention, the porous electrode supports 340 and 440, depicted in FIGS. 24 and 25, comprise a length of non-conductive, porous, malleable material adapted to fit within elongated channels 323 and 423 of the insulated electrode sheaths 320 and 420 and upper and lower jaw mounts 300 and 400. In one embodiment of the invention, porous electrode supports 340 and 440 have a relatively square cross sectional area. During assembly, the elongated tubular electrodes 330 and 430 are inserted into elongated lumens of the porous electrode supports 340 and 440. In one embodiment of the invention, the series of fluid ports alternate along two rows that are 90 degrees relative to each other. In one embodiment, each electrode has twelve ports arranged so that the two rows each include six alternating ports. The fluid ports of the tubular electrodes of upper and lower jaws 35 and 45 are oriented away from each other so that the conductive fluid emitted from the lumen through the series of fluid ports then migrates laterally through the pores of the porous electrode supports 340 and 440 and around its circumference to thoroughly and uniformly wet the porous electrode supports 340 and 440 along the upper and lower jaws 35 and 45.

The sub-assemblies so formed are fitted into the elongated channels 323 and 423 of the insulated electrode sheaths 320 and 420 and the upper and lower jaw mounts 300 and 400 as shown in FIG. 25. Adhesive may be used to affix the sub-assembly of the elongated tubular electrodes 330 and 430 inserted into the porous electrode supports 340 and 440 to the insulated electrode sheaths 320 and 420. The adhesive does not block migration of conductive fluid around the porous electrode supports 340 and 440. Electrode sheaths 320 and 420 are formed having an elongated tapered internal recess that receives the malleable backbones 310 and 410, respectively, as shown in FIGS. 24 and 25.

Figure 30:
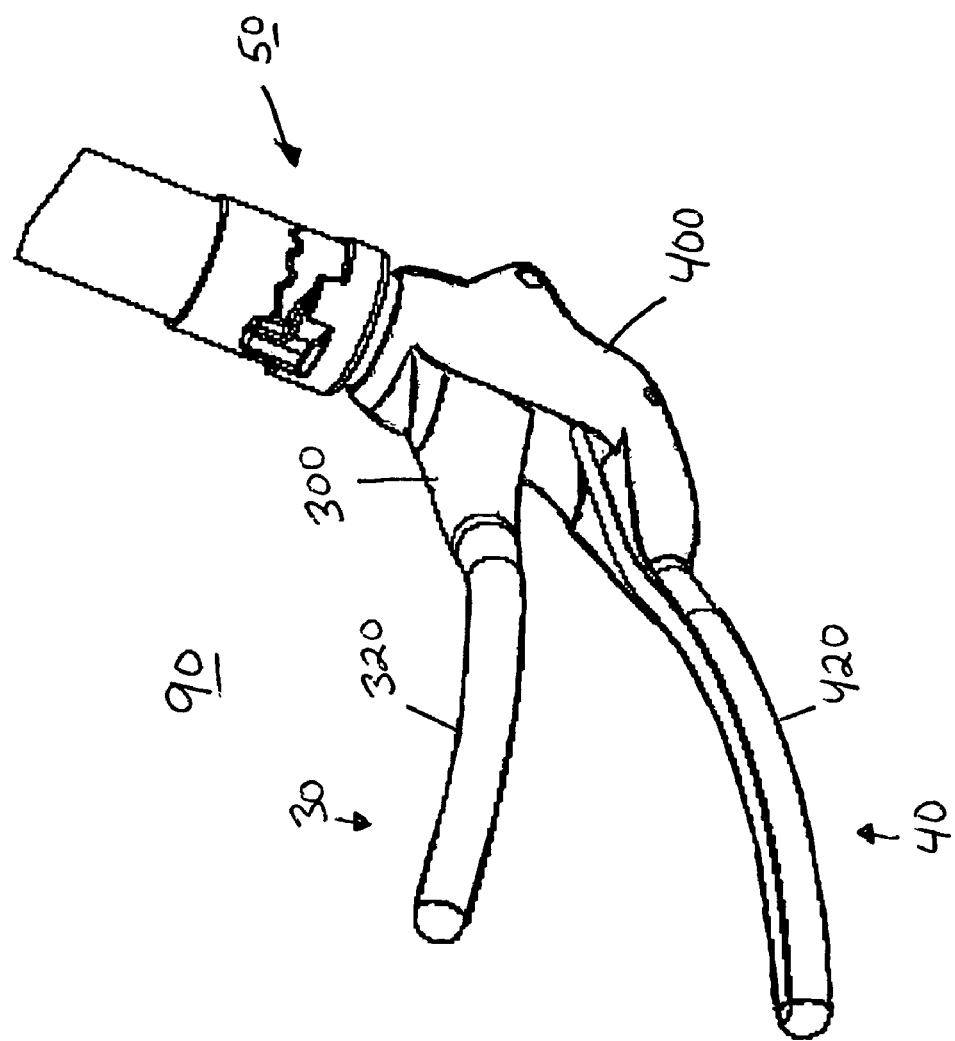
FIG. 30 is a view of the jaw assembly of one embodiment of the present invention.
Figure 31:
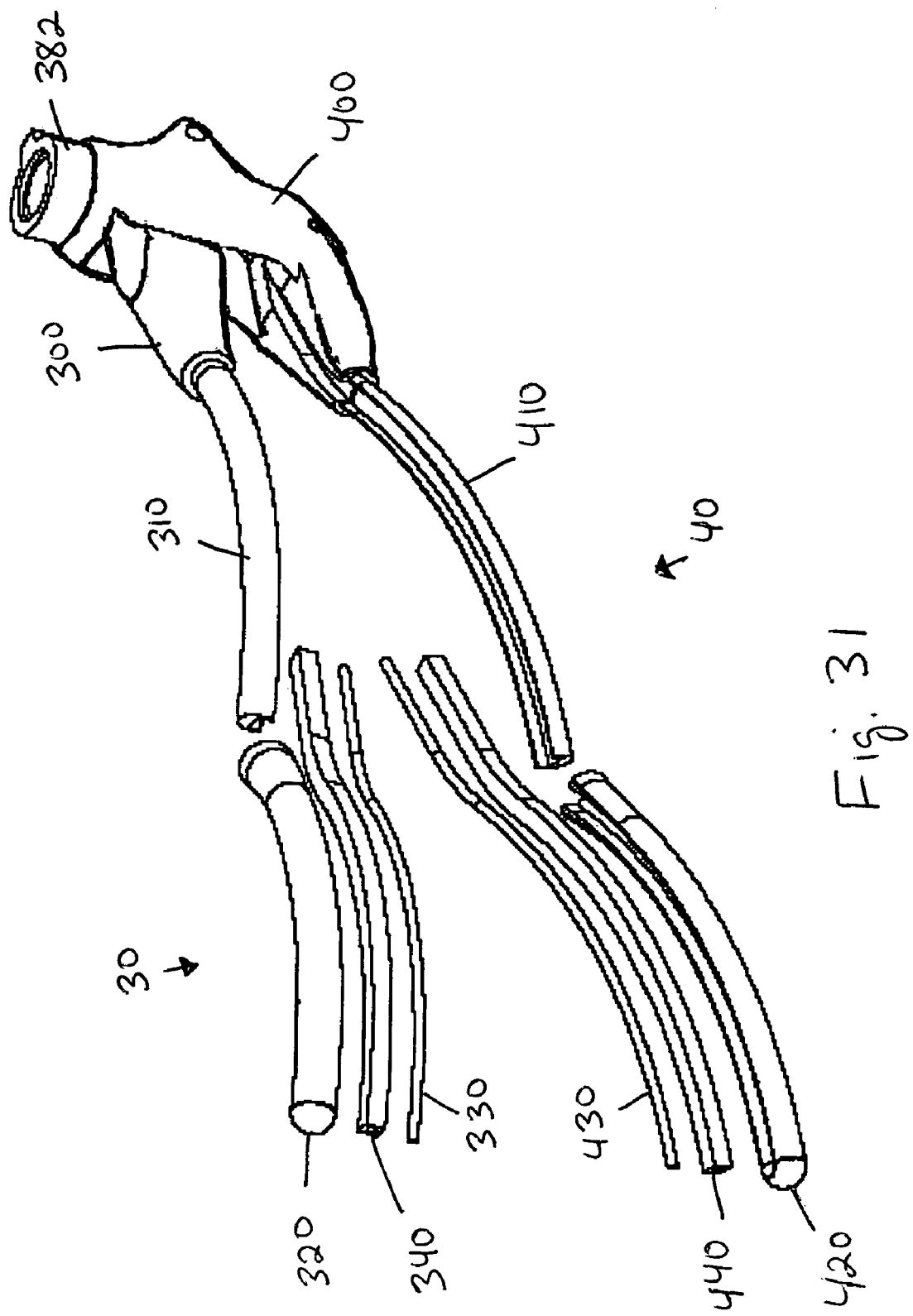
FIG. 31 is an exploded view of a jaw assembly of one embodiment of the present invention.

Referring to FIGS. 30 and 31, in one embodiment of the invention, upper and lower jaws 35 and 45 have a predetermined corresponding curved shape and are relatively rigid so as not to be malleable. Upper jaw 35 includes a relatively rigid, upper jaw mount 300, an elongated relatively rigid backbone 310, an elongated insulated electrode sheath 320, an elongated conductive electrode 330, and an elongated electrode support 340. Upper jaw mount 300 may be fabricated of plastic or other insulated material, and in preferred embodiments may be fabricated of Teflon filled polycarbonate plastic. Backbone 310 is made of rigid stainless steel or other rigid metal and is attached at a proximal end to upper jaw mount 300. An insulated electrode sheath 320 is fitted over spine 310 with its proximal end located adjacent upper jaw mount 300. The elongated conductive electrode 330 comprises a length of conductive metal tubing fitted into a lumen of the elongated electrode support 340. The insulated electrode sheath 320 is formed with a channel that receives the sub-assembly of the elongated conductive electrode 330 and electrode support 340 disposed along the jaw 35. Electrode sheath 320 may be fabricated of a flexible, electrically insulating, material, for example, silicone rubber or PVC. Elongated electrode support 340 is preferably fabricated of a porous material, such as Porex™ plastic, allowing for conductive fluid infiltration through its sidewall along its length and correspondingly delivery of conductive fluid along the length of jaw 35.

The lower jaw assembly 40 also includes a relatively rigid, lower jaw mount 400, an elongated relatively rigid backbone 410, an elongated insulated electrode sheath 420, an elongated conductive electrode 430, and an elongated electrode support 440 that are all formed of the same materials as the corresponding elements of the upper jaw assembly 30.

Figure 32:
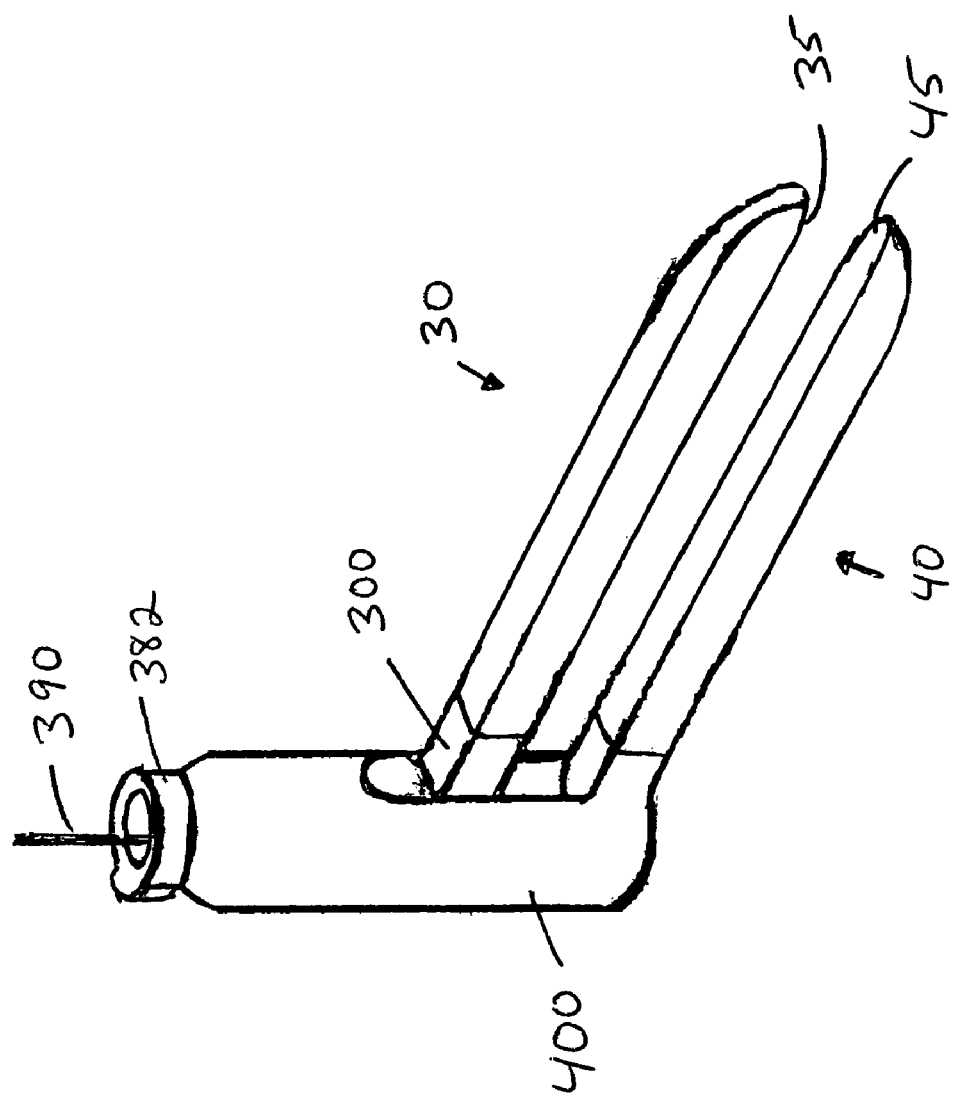
FIG. 32 is a view of the jaw assembly of one embodiment of the present invention.
Figure 33:
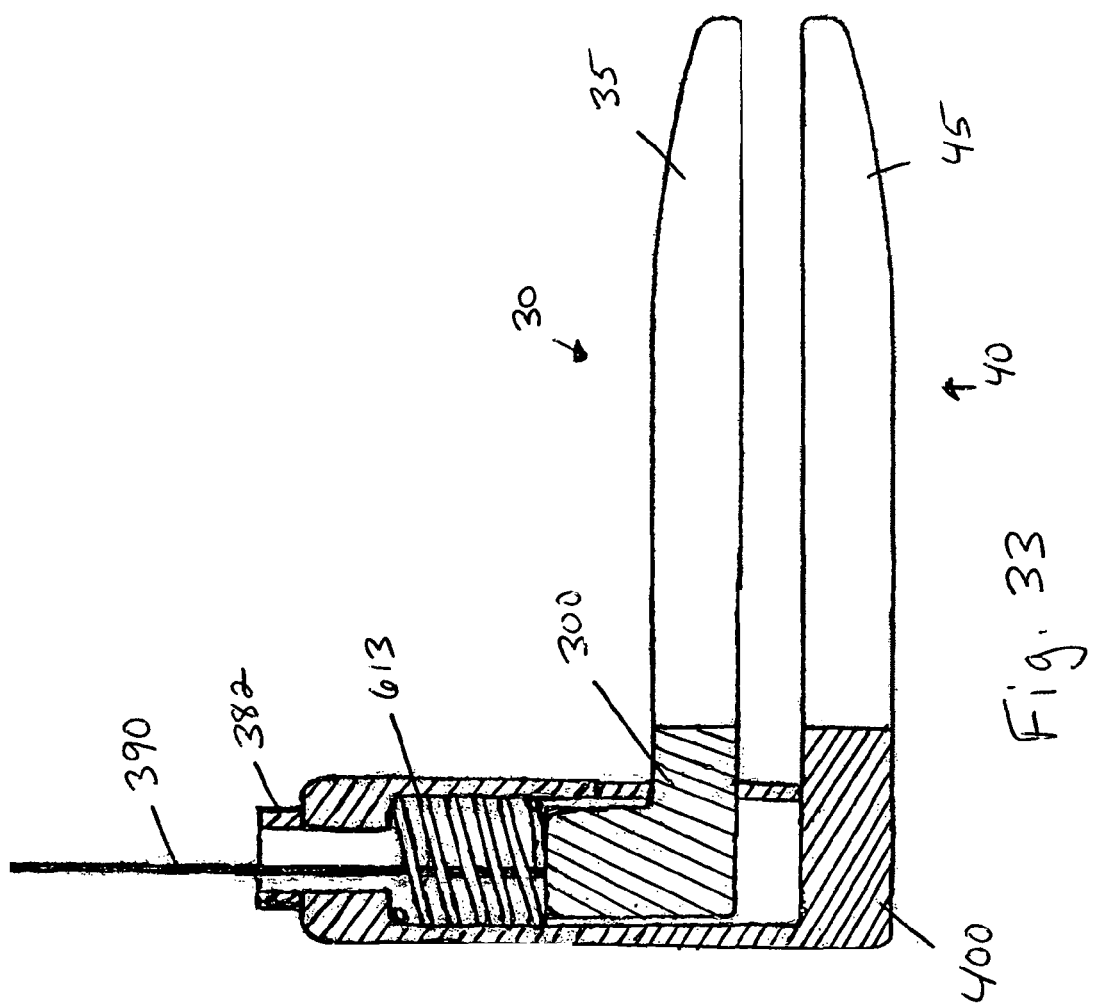
FIG. 33 is a cross-section view of the jaw assembly of one embodiment of the present invention.

Referring to FIGS. 32 and 33, an alternative configuration of upper and lower jaw assemblies may be used according to one embodiment of the invention. Upper and lower jaw assemblies 30 and 40 are configured so that upper jaw 35 moves in a parallel fashion relative to lower jaw 45. Upper jaw 35 includes upper jaw mount 300 having a portion contained within a lumen of lower jaw mount 400. The portion of upper jaw mount 300 contained within a lumen of lower jaw mount 400 is free to travel within lower jaw mount 400. The distal end of cable 390 is attached to upper jaw mount 300. A spring washer 613 is interposed between the distal end of collar 382 and the proximal end of upper jaw mount 300. Spring washer 613 urges the upper and lower jaws 35 and 45, respectively, into a closed configuration, i.e., spring washer 613 urges the upper jaw 35 towards the lower jaw 45.

Figure 34:
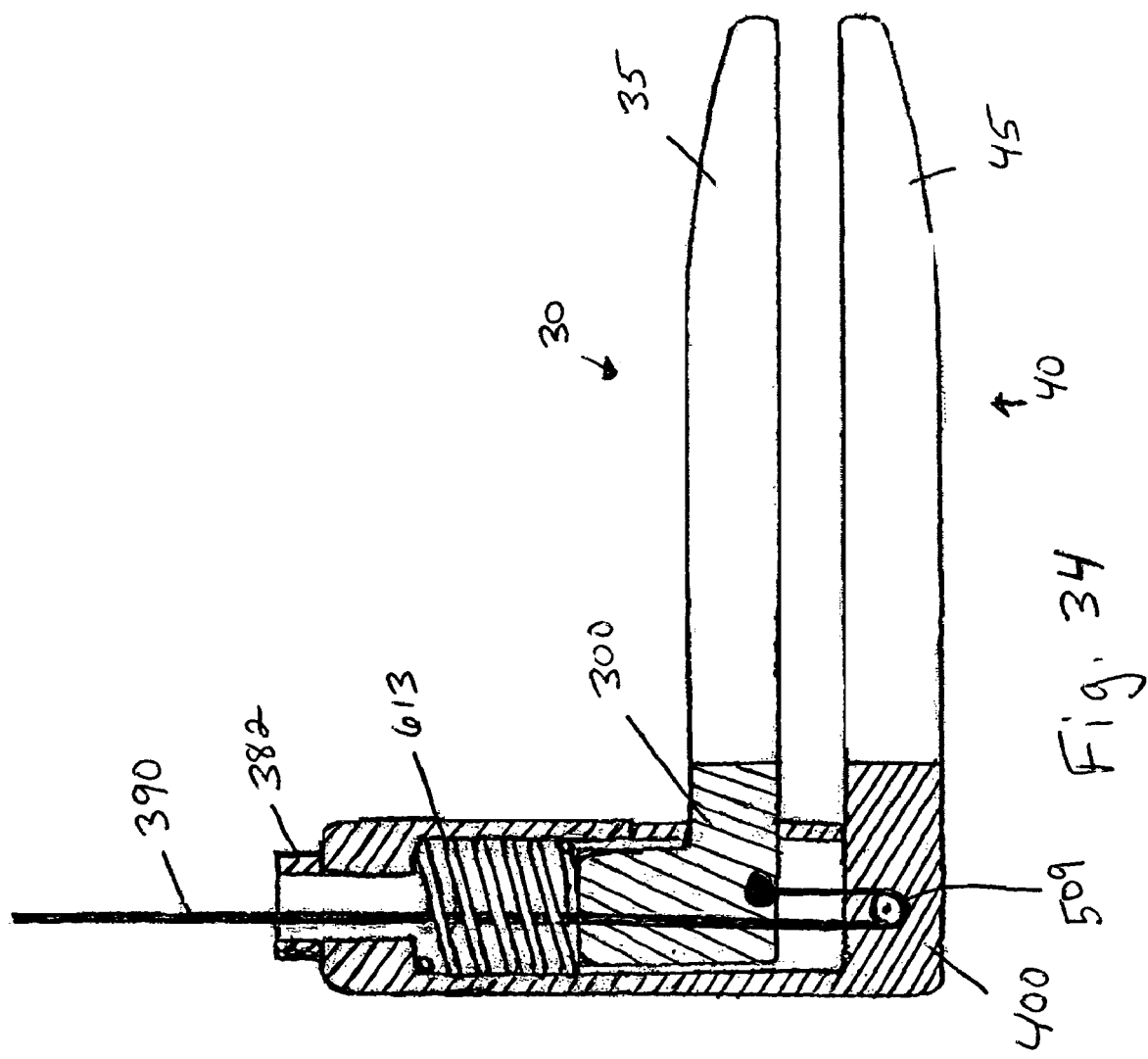
FIG. 34 is a cross-section view of the jaw assembly of one embodiment of the present invention.

Cable 390 extends from the trigger 20 and is employed to open and close the jaws 35 and 45. In one embodiment of the invention, when the cable 390 is tensioned by squeezing trigger 25, cable 390 is pulled in a proximal direction thereby pulling upper jaw 35 in a parallel direction away from lower jaw 45. Therefore, tensioning cable 390 opens jaws 35 and 45 while releasing the tension in cable 390 closes the jaws 35 and 45. It should be noted that during this operation, the lower jaw mount 400 remains fixed relative to the swivel assembly 50 and only upper jaw mount 300 moves relative to the swivel assembly 50 or the handle 10. Proximal movement of cable 390 does not affect the position of the lower jaw 45 relative to the handle 10, nor does it affect the selected roll R adjustment of swivel 500. Rotation of the jaw assembly 90 and swivel 500 about the roll axis does not affect the operation of the cable 390 because the cable 390 passes through the swivel 500 and enters the jaw assembly 90 along the roll axis. Alternatively, the trigger mechanism may be designed so that the squeezing of trigger 25 opens the jaws 35 and 45. Alternatively, as shown in FIG. 34, cable 390 may run through a lumen or channel in upper jaw mount 300, around a pulley 509 mounted within a recess in lower jaw mount 400 and back to upper jaw mount 300 where cable 390 is fixed. In the embodiment shown in FIG. 34, tensioning of cable 390 will close jaws 35 and 45.

Figure 35:
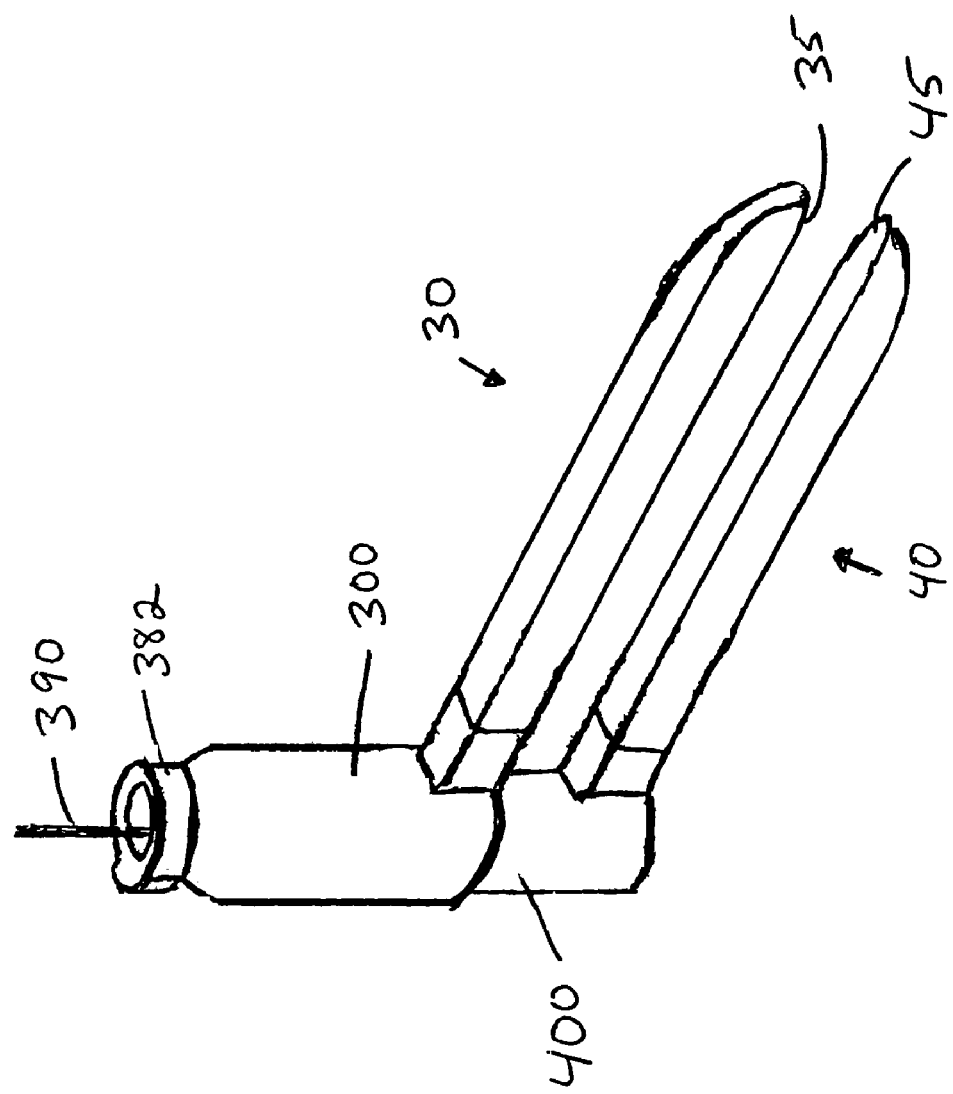
FIG. 35 is a view of the jaw assembly of one embodiment of the present invention.
Figure 36:
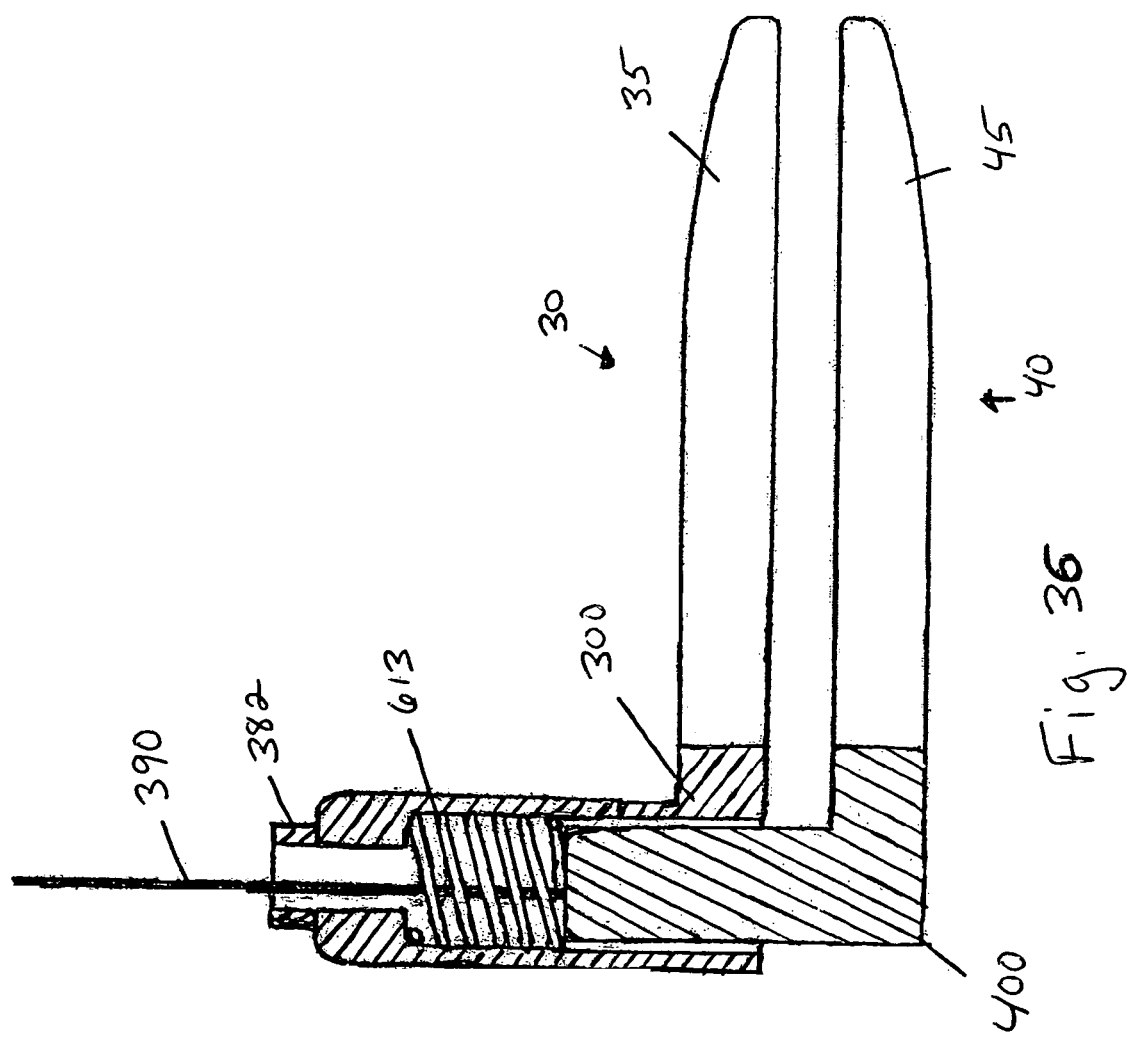
FIG. 36 is a cross-section view of the jaw assembly of one embodiment of the present invention.

Referring to FIGS. 35 and 36, an alternative configuration of upper and lower jaw assemblies may be used according to one embodiment of the invention. Upper and lower jaw assemblies 30 and 40 are configured so that lower jaw 45 moves in a parallel fashion relative to upper jaw 35. Upper jaw 35 includes upper jaw mount 300 having a portion comprising a lumen for receiving a proximal portion of lower jaw mount 400. The portion of lower jaw mount 400 contained within a lumen of upper jaw mount 300 is free to travel within upper jaw mount 300. Upper jaw mount 300 includes collar 382. The distal end of cable 390 is attached to lower jaw mount 400. A spring washer 613 is interposed between the distal end of collar 382 and the proximal end of lower jaw mount 400. Spring washer 613 urges the upper and lower jaws 35 and 45, respectively, into an open configuration, i.e., spring washer 613 urges the lower jaw 45 away from the upper jaw 35.

Cable 390 extends from the trigger 20 and is employed to open and close the jaws 35 and 45. In one embodiment of the invention, when the cable 390 is tensioned by squeezing trigger 25, cable 390 is pulled in a proximal direction thereby pulling lower jaw 45 in a parallel direction towards upper jaw 35. Therefore, tensioning cable 390 closes jaws 35 and 45 while releasing the tension in cable 390 opens the jaws 35 and 45. It should be noted that during this operation, the upper jaw mount 300 remains fixed relative to the swivel assembly 50 and only lower jaw mount 400 moves relative to the swivel assembly 50 or the handle 10. Proximal movement of cable 390 does not affect the position of the upper jaw 35 relative to the handle 10, nor does it affect the selected roll R adjustment of swivel 500. Rotation of the jaw assembly 90 and swivel 500 about the roll axis does not affect the operation of the cable 390 because the cable 390 passes through the swivel 500 and enters the jaw assembly 90 along the roll axis.

Figure 37:
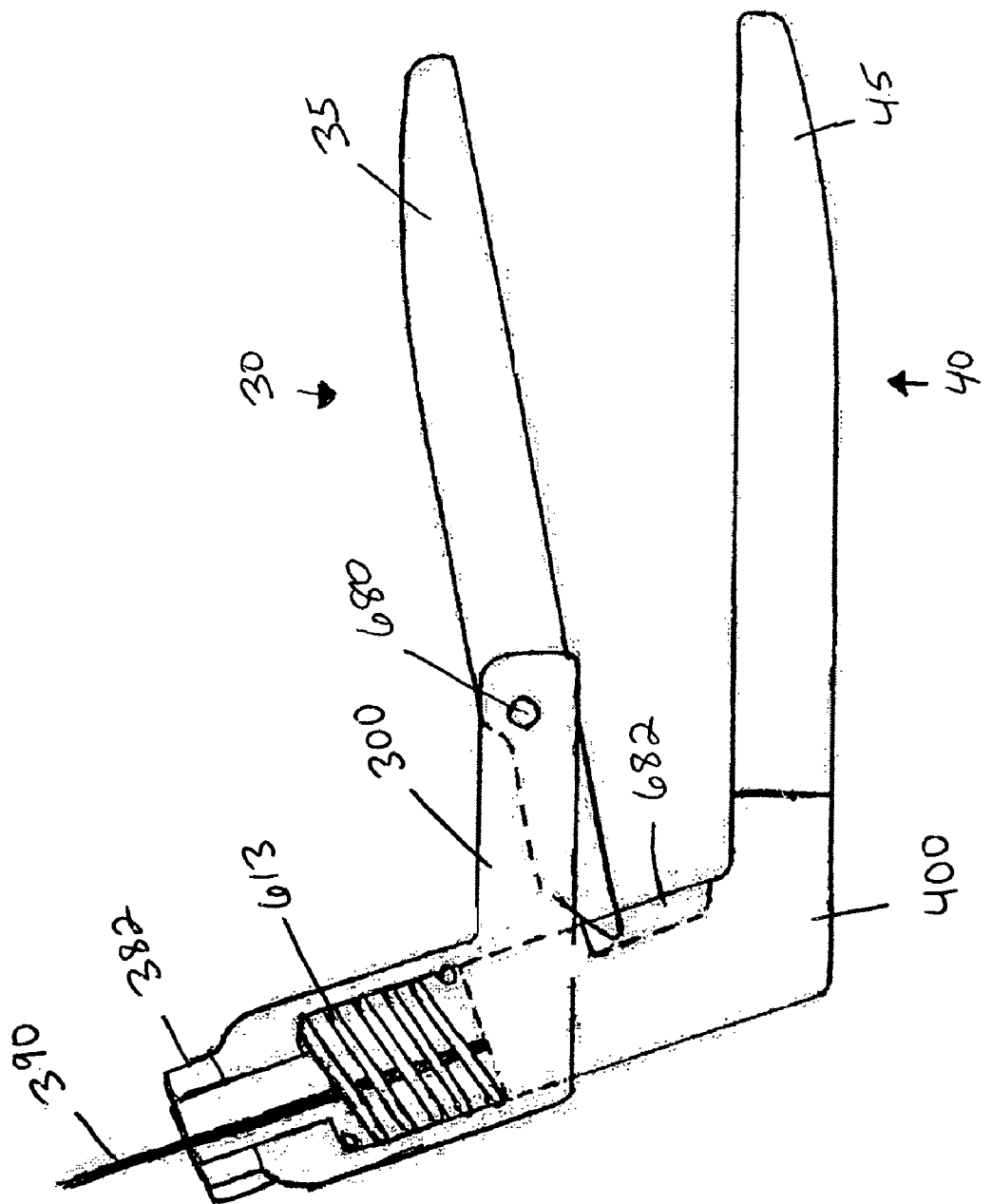
FIG. 37 is a cross-section view of the jaw assembly of one embodiment of the present invention.

Referring to FIG. 37, an alternative configuration of upper and lower jaw assemblies may be used according to one embodiment of the invention. Upper and lower jaw assemblies 30 and 40 are configured so that lower jaw 45 moves in a parallel fashion relative to upper jaw mount 300. Upper jaw 35 includes upper jaw mount 300 having a portion comprising a lumen for receiving a proximal portion of lower jaw mount 400. The portion of lower jaw mount 400 contained within a lumen of upper jaw mount 300 is free to travel within upper jaw mount 300. Upper jaw mount 300 includes collar 382. The distal end of cable 390 is attached to lower jaw mount 400. A spring washer 613 is interposed between the distal end of collar 382 and the proximal end of lower jaw mount 400. Spring washer 613 urges the upper and lower jaws 35 and 45, respectively, into an open configuration, i.e., spring washer 613 urges the lower jaw 45 away from the upper jaw 35. A pin 680 extends through aligned holes through the distal portion of upper jaw mount 300 and upper jaw 35. The ends of pin 680 are fixed to the upper jaw mount 300 thereby allowing upper jaw 35 to rotate about pin 680. The distal end of jaw 35 fits within a groove or recess 682 within lower jaw mount 400. Having upper jaw 35 rotatably attached to upper jaw mount 300 allows jaws 35 and 45 to be opened wider, thereby making it easier to place tissue in between the upper and lower jaws 35 and 45. Further, as tissue is compressed between jaws 35 and 45, jaw 35 is capable of rotating into parallel alignment with jaw 45, thereby more evenly compressing tissue between jaws 35 and 45. Recess 682 may be configured so that jaw 35 is rotated into a fully open position as spring washer 613 urges lower jaw 45 away from the upper jaw 35.

Cable 390 extends from the trigger 20 and is employed to open and close the jaws 35 and 45. In one embodiment of the invention, when the cable 390 is tensioned by squeezing trigger 25, cable 390 is pulled in a proximal direction thereby pulling lower jaw 45 in a direction towards upper jaw 35. Therefore, tensioning cable 390 closes jaws 35 and 45 while releasing the tension in cable 390 opens the jaws 35 and 45. It should be noted that during this operation, the upper jaw mount 300 remains fixed relative to the swivel assembly 50 and only lower jaw mount 400 moves relative to the swivel assembly 50 or the handle 10. Proximal movement of cable 390 does not affect the position of the upper jaw 35 relative to the handle 10, nor does it affect the selected roll R adjustment of swivel 500. Rotation of the jaw assembly 90 and swivel 500 about the roll axis does not affect the operation of the cable 390 because the cable 390 passes through the swivel 500 and enters the jaw assembly 90 along the roll axis.

As shown in FIG. 33, in one embodiment of the invention, jaw assembly 90 may be designed so that lower jaw 45 is fixedly oriented about 90 degrees relative to swivel assembly 50. Alternatively, as shown in FIG. 25, jaw assembly 90 may be designed so that lower jaw 45 is fixedly oriented in a range between about 90 degrees and about 180 degrees relative to swivel assembly 50.

As shown in FIG. 36, in one embodiment of the invention, jaw assembly 90 may be designed so that upper jaw 35 is fixedly oriented about 90 degrees relative to swivel assembly 50. Alternatively, as shown in FIG. 37, jaw assembly 90 may be designed so that upper jaw 35 is fixedly oriented in a range between about 90 degrees and about 180 degrees relative to swivel assembly 50.

To help prevent rotation of jaw mounts 300 and 400 relative to each other in jaw assemblies shown in FIGS. 33, 36 and 37, jaw mounts 300 and 400 may include interlocking features. For example, jaw mount 400 may comprise a slot or groove wherein fits a boss or pin, for example, of jaw mount 300, thereby preventing rotation of jaw mounts 300 and 400 relative to each other yet still allowing a sliding or translational movement to occur.

Figure 38:
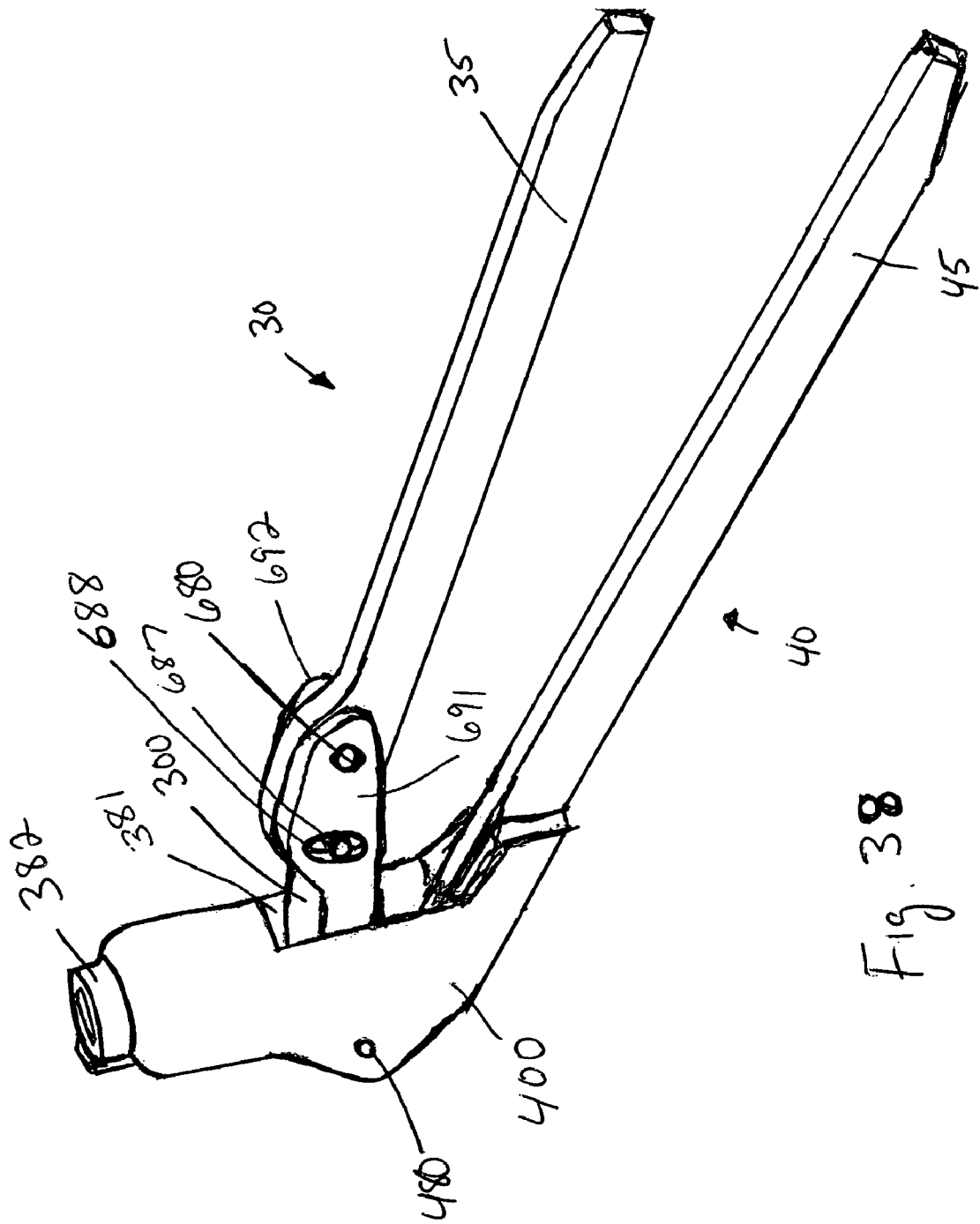
FIG. 38 is a view of the jaw assembly of one embodiment of the present invention.

Referring to FIG. 38, an alternative configuration of upper and lower jaw assemblies may be used according to one embodiment of the invention. Upper jaw mount 300 comprises a pair of parallel plates or flanges 691 and 692. A pin 680 extends through aligned holes through flanges 691 and 692 and upper jaw 35. The ends of pin 680 are fixed to flanges 691 and 692 thereby allowing upper jaw 35 to rotate about pin 680. The distal end of jaw 35 includes a pin or boss 687 that fits within a slot 688 within flanges 691 and 692. Pin 687 and slot 688 limit the amount of movement jaw 35 has relative to jaw mount 300. The lower jaw mount 400 is formed with an opening 381 for receiving the proximal end of upper jaw mount 300. When assembled, a proximal portion of the upper jaw mount 300 is fitted within the opening 381. A pin 480 extends through aligned holes through the proximal portion of upper jaw mount 300 and the lower jaw mount 400. The ends of pin 480 are fixed to the lower jaw 400 thereby allowing the proximal portion of the upper jaw mount 300 to be rotated about the pin 480, thereby allowing jaws 35 and 45 to open and close. Having upper jaw 35 rotatably attached to upper jaw mount 300 allows jaw 35 to be capable of assuming a parallel alignment relative to jaw 45 even as upper jaw mount 300 is rotated about pin 480 as jaws 35 and 45 are opened and closed. For example, as tissue is compressed between jaws 35 and 45, jaw 35 is capable of rotating into parallel alignment with jaw 45, thereby more evenly compressing tissue between jaws 35 and 45. The pivoting upper jaw 35 may be spring loaded using a spring or other elastic material, for example, to bias the jaw 35 into an open configuration.

Figure 39:
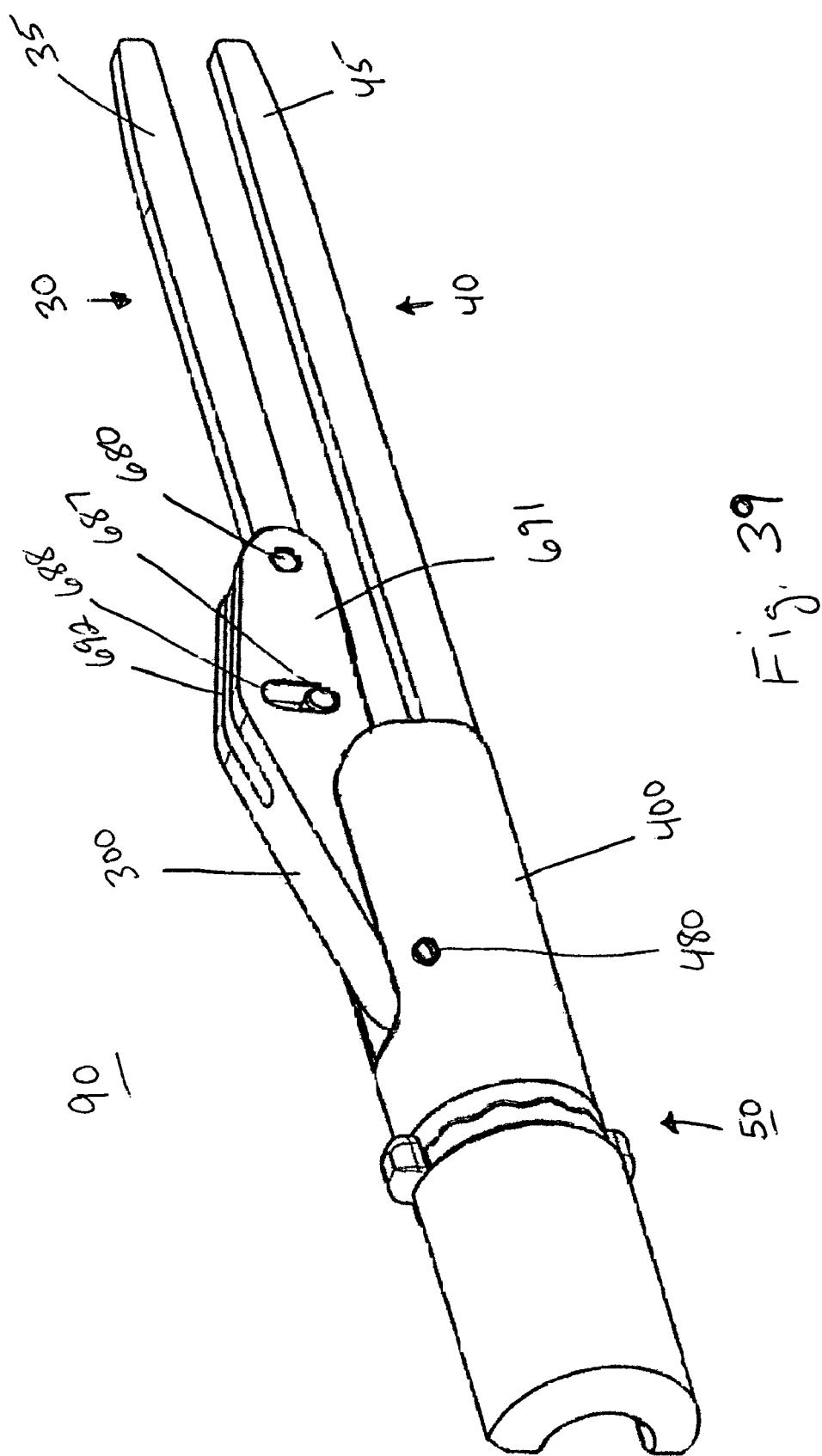
FIG. 39 is a view of the jaw assembly of one embodiment of the present invention.

In one embodiment of the invention, jaw assembly 90 may be designed so that either the upper jaw 35 or the lower jaw 45 is fixedly oriented about 180 degrees relative to swivel assembly 50. For example, lower jaw mount 400 and lower jaw 45 are shown in FIG. 39 to be fixed about 180 degrees relative to swivel assembly 50. Having jaws 35 and 45 in alignment with shaft 11 of handle 10, as shown in FIG. 39, would make the device suitably configured for delivery through a small, percutaneous penetration, for example a small cut, incision, stab wound, hole, port, cannula, trocar sleeve or the like. The term "trocar sleeve" appearing herein also refers to cannulae and ports.

Figure 40:
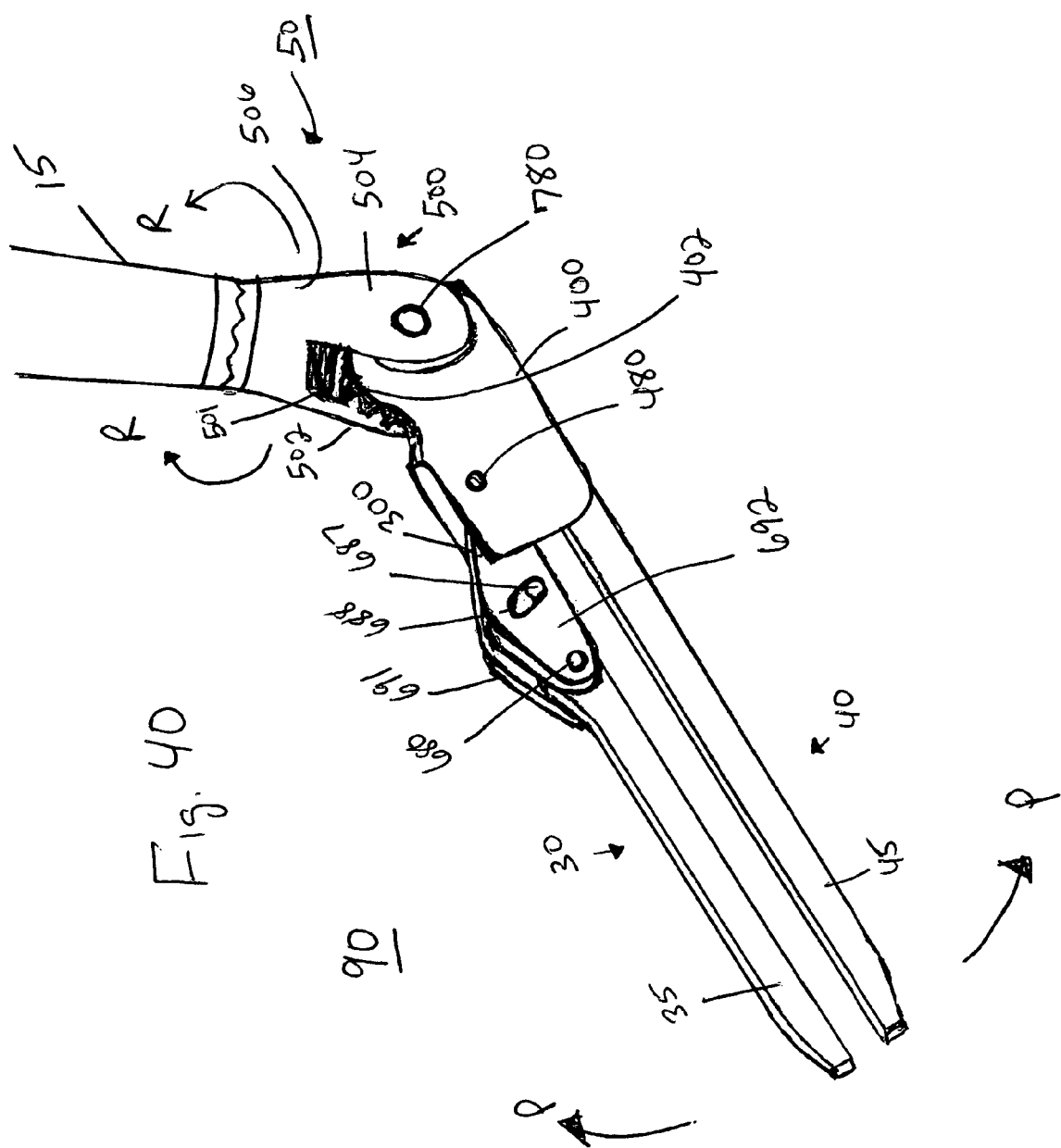
FIG. 40 is a view of the jaw assembly of one embodiment of the present invention.

Alternative embodiment of jaw assembly 90 is shown in FIG. 40, wherein jaw assembly 90 includes an upper jaw assembly 30, a lower jaw assembly 40, and a swivel assembly 50. The upper jaw and lower jaw assemblies 30 and 40 have opposed upper and lower jaws 35 and 45. The swivel assembly 50 provides the physician with the opportunity to position the jaw assembly 90 in a variety of orientations relative to the handle 10. In one embodiment, the physician may manually grasp and rotate the swivel assembly 50 and the jaw assembly 90 to provide a roll adjustment R, preferably through an arc of at least 300 degrees, relative to the axis of the distal end 15 of the handle 10 through interaction of components of the handle and swivel assembly described further above. In one embodiment, the physician may manually grasp the jaw assembly 90 and adjust it in pitch P relative to the swivel assembly 50 through the interaction of components of the jaw assembly 90 and the swivel assembly 50. In one embodiment, the available arc of pitch P adjustment extends over at least 90 degrees. As shown in FIG. 40, upper jaw mount 300 may comprise a pair of parallel plates or flanges 691 and 692. A pin 680 extends through aligned holes through flanges 691 and 692 and upper jaw 35. The ends of pin 680 are fixed to flanges 691 and 692 thereby allowing upper jaw 35 to rotate about pin 680. The distal end of jaw 35 includes a pin or boss 687 that fits within a slot 688 within flanges 691 and 692. Pin 687 and slot 688 limit the amount of movement jaw 35 has relative to jaw mount 300. Having upper jaw 35 rotatably attached to upper jaw mount 300 allows jaw 35 to be capable of assuming a parallel alignment relative to jaw 45 even as upper jaw mount 300 is rotated about pin 480 as jaws 35 and 45 are opened and closed. For example, as tissue is compressed between jaws 35 and 45, jaw 35 is capable of rotating into parallel alignment with jaw 45, thereby more evenly compressing tissue between jaws 35 and 45.

As shown in FIG. 40, the swivel assembly 50 includes a swivel 500 that has a pair of parallel plates or flanges 502 and 504 extending distally from swivel proximal portion 506 and a extending detent 501 extending laterally between flanges 502 and 504. The lower jaw mount 400 is mounted to the swivel assembly 50 by fitting the proximal end of lower jaw mount 400 in swivel flanges 502 and 504. The lower jaw mount 400 is pivotably mounted to the swivel 500 by pin 780. Therefore, the upper and lower jaw assemblies 30 and 40 may be pivoted together relative to the swivel 500, allowing for movement of the jaws 35 and 45 together through the range of pitch P adjustment. The selected pitch P adjustment is maintained by the engagement of the detent 501 into an opposed pair of notches 402 located at the proximal end of lower jaw mount 400, stabilizing the upper and lower jaws 35 and 45 in a desired orientation relative to the swivel assembly 50, as described above. In use, the physician adjusts the relative positions of the jaws 35 and 45 relative to the swivel assembly 50 by simply manually moving the jaw assemblies 30 and 40 in the pitch P direction around the pivot axis pin 780. The detent 501 simply rides over the ridges separating adjacent notches 402.

As shown in FIG. 40, upper jaw mount 300 may comprise a pair of parallel plates or flanges 691 and 692. A pin 680 extends through aligned holes through flanges 691 and 692 and upper jaw 35. The ends of pin 680 are fixed to flanges 691 and 692 thereby allowing upper jaw 35 to rotate about pin 680. The distal end of jaw 35 includes a pin or boss 687 that fits within a slot 688 within flanges 691 and 692. Pin 687 and slot 688 limit the amount of movement jaw 35 has relative to jaw mount 300. The lower jaw mount 400 is formed with an opening for receiving the proximal end of upper jaw mount 300. When assembled, a proximal portion of the upper jaw mount 300 is fitted within the opening. A pin 480 extends through aligned holes through the proximal portion of upper jaw mount 300 and the lower jaw mount 400. The ends of pin 480 are fixed to the lower jaw 400 thereby allowing the proximal portion of the upper jaw mount 300 to be rotated about the pin 480, thereby allowing jaws 35 and 45 to open and close. Having upper jaw 35 rotatably attached to upper jaw mount 300 allows jaw 35 to be capable of assuming a parallel alignment relative to jaw 45 even as upper jaw mount 300 is rotated about pin 480 as jaws 35 and 45 are opened and closed. For example, as tissue is compressed between jaws 35 and 45, jaw 35 is capable of rotating into parallel alignment with jaw 45, thereby more evenly compressing tissue between jaws 35 and 45.

Figure 41:
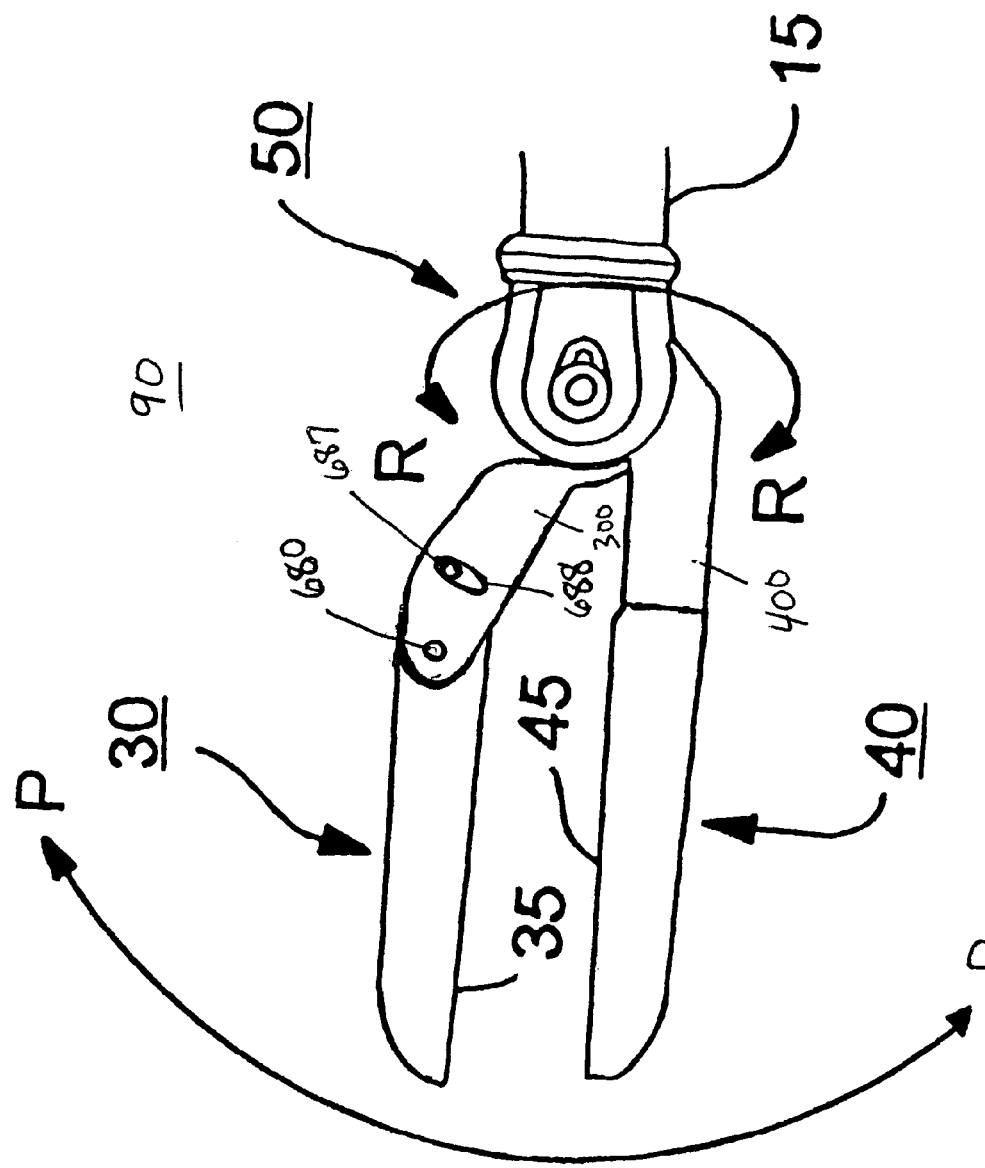
FIG. 41 is a view of the jaw assembly of one embodiment of the present invention.

As shown in FIG. 41, one embodiment of the jaw assembly 90, as described above and shown in FIGS. 1 and 2, may include an upper jaw mount 300 comprising a pair of parallel plates or flanges as described above. A pin 680 extends through aligned holes through the pair of flanges of upper jaw mount 300 and upper jaw 35. The ends of pin 680 are fixed to the flanges thereby allowing upper jaw 35 to rotate about pin 680. The distal end of jaw 35 includes a pin or boss 687 that fits within a slot 688 within the flanges. Pin 687 and slot 688 limit the amount of movement jaw 35 has relative to jaw mount 300. Having upper jaw 35 rotatably attached to upper jaw mount 300 allows jaw 35 to be capable of assuming a parallel alignment relative to jaw 45 even as upper jaw mount 300 is pivoted relative to lower jaw mount 400 as jaws 35 and 45 are opened and closed. For example, as tissue is compressed between jaws 35 and 45, jaw 35 is capable of rotating into parallel alignment with jaw 45, thereby more evenly compressing tissue between jaws 35 and 45.

As shown in FIGS. 42 and 43, one embodiment of the jaw assembly 90 suitably configured for delivery through a small, percutaneous penetration, for example a small cut, incision, stab wound, hole, port, cannula, trocar sleeve or the like. FIG. 42 is a bottom view of an alternative embodiment of jaw assembly 90 with jaws 35 and 45 a closed position, whereas FIG. 43 is a bottom view of jaw assembly 90 with jaws 35 and 45 an open position. As seen in FIGS. 42 and 43, in this embodiment of the invention, jaws 35 and 45 are oriented parallel to each other during the entire process of opening and closing the jaws. In addition, neither jaw is fixed in place, but instead move relative to each other. Cable 390 may extend between jaw assembly 90 and handle 10 through shaft 11. The proximal end of cable 390 is connected to actuator lever or trigger 20 on handle 10. The distal end of cable 390 is connected to jaw assembly 90. Trigger 20 may be used to remotely and controllably actuate the jaw assembly 90 as described below.

As shown in FIGS. 42 and 43, cable 390 passes through collar 382 of anchor 840. The jaw assembly 90 may be mounted to the swivel assembly 50 (as described above) by fitting the distal end of swivel 500 into collar 382 of anchor 840. The distal end of cable 390 is coupled to slide 850 which is slidably coupled to anchor 840. Referring to FIGS. 44 and 45, plan views of upper and lower jaw mounts 300 and 400 are shown with a portion of jaw 35 coupled to jaw mount 300 and a portion of jaw 45 coupled to jaw mount 400. In this embodiment, jaw mounts 300 and 400 include first, second and third slots 871, 872, 873 with the second slot 872 being oriented substantially perpendicular to the jaws 35 and 45. The second slot 872 of jaw mounts 300 and 400 are aligned so that a pin passing through the second slots 872 helps maintain jaws 35 and 45 parallel to one another throughout movement between a closed and an open position. The first and third slots 871, 873 of each of jaw mounts 300 and 400 are parallel to one another and oriented 45 degrees relative to the jaws 35 and 45. Referring to FIG. 42, first, second and third pins 875, 876, 877 pass through the first, second and third slots 871, 872, 873.

Referring to FIGS. 46 and 47, side and plan views of slide 850 are shown. Slide 850 includes throughhole 880 for receiving cable 390. The distal end of cable 390 preferably has an anchor (not shown) which prevents withdrawal of cable 390 through throughhole 880. Slide 850 includes first and second holes 881, 882 extending through first and second sides 883, 884. The first and third pins 875, 877 extend through first and second holes 881, 882 of slide 850 and first and third slots 871, 873 of jaw mounts 300 and 400 for moving spreader members 860, 870 when slide 850 is moved. Slide 850 also includes grooves 890 extending between the first and second holes 881, 882.

Referring to FIGS. 48 and 49, side and plan views of anchor 840 are shown. Anchor 840 includes central guides 900 which are positioned in grooves 890 of slide 850. Central guides 900 and grooves 890 cooperate to help maintain the linearly slidable relationship between slide 850 and anchor 840. Central guides 900 also include holes 901 therethrough for receiving the second pin 876 which extends through second slots 872 in spreader members 860, 870. Anchor 840 includes throughhole 902 for receiving cable 390 and the distal end of swivel 500. Proximal end 910 of anchor 840 includes four arms 815, three of which are shown in FIGS. 48 and 49, which extend between central guides 900 and proximal end 910.

Figure 52:
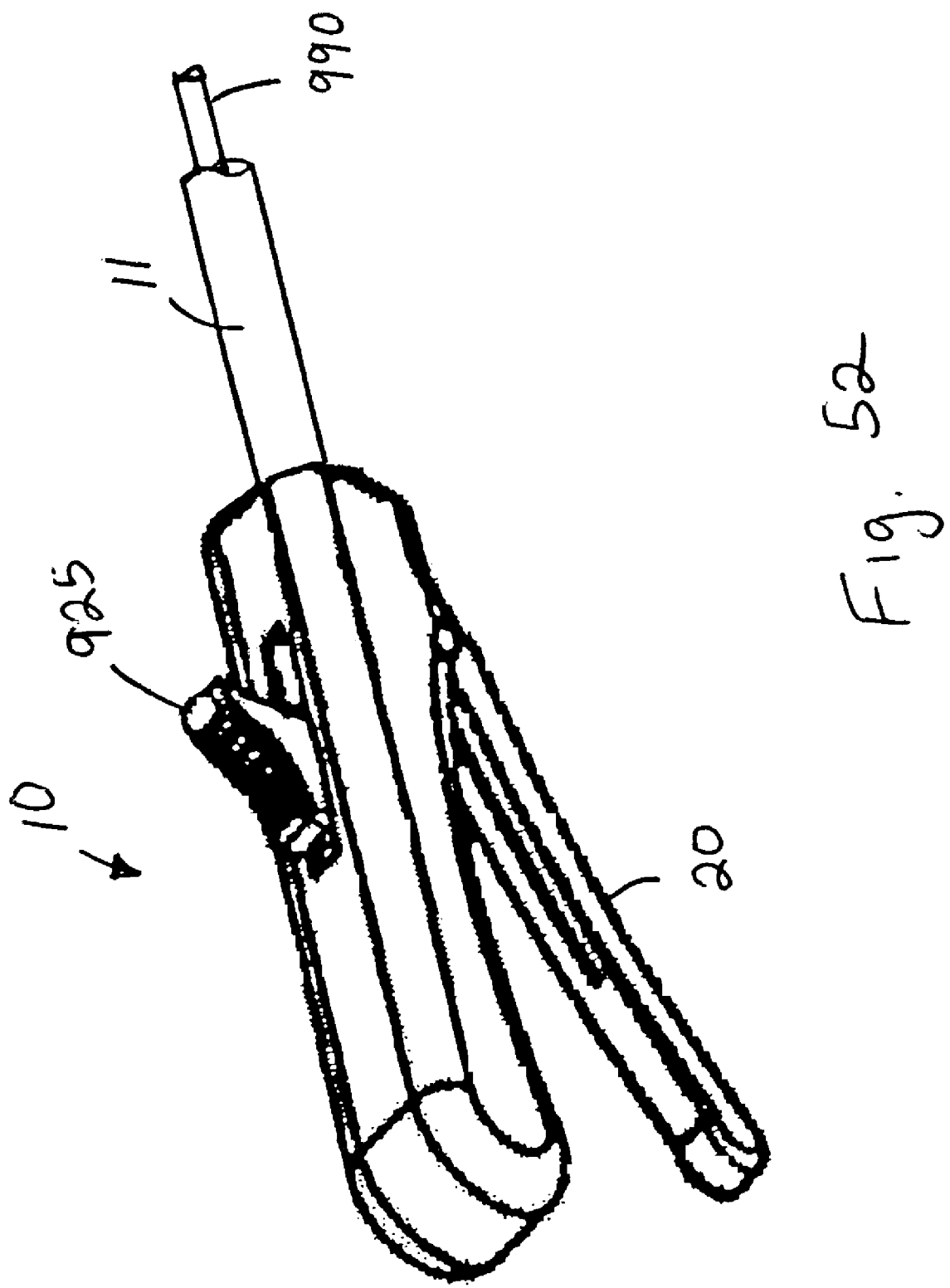
FIG. 52 is a view of a portion of a hemostat according to one embodiment of the present invention.

Referring to FIGS. 50 and 51, in an alternative embodiment of the invention, anchor 840 may be connected to coupling member 983 of linkage 950. Linkage 950 comprises longitudinal cable or rod 990 slidably disposed within shaft 11 of handle 10 and a link 980 having a first and second ends 981, 982. The proximal end of rod 990, as shown in FIG. 52, is coupled to handle 10. Coupling member 983 of linkage 950 has a bifurcated proximal end with first and second coupling points 984 and 985. First end 981 of link 980 is coupled to the distal end of rod 990 and second end 982 of link 980 is coupled to coupling member 983 at coupling point 985. Shaft 11 has an angled opening 1000 (as seen in FIGS. 50 and 51) at its distal end to allow jaw assembly 90 to pivot into an orientation transverse to shaft 11. Second coupling point 984 of coupling member 983 is pinned to distal end of shaft 11 to form a pivot point 910. Jaw assembly 90 which is connected to coupling member 983 will therefore pivot about a transverse axis through pivot point 910. Fluid and/or electrical power may be routed through conduit 960 to jaws 35 and 45.

Referring to FIG. 52, in one embodiment of the invention, a thumb slide 925, for example, a slidable button within a longitudinal slot, may be used to move cable or rod 990 in proximal and distal directions, thereby remotely and controllably actuate jaw assembly 90 to pivot or rotate about pivot point 910. An actuator knob may be used instead of a thumb slide 925, for example, to remotely and controllably actuate linkage 950. The knob may be fixed to rod 990. The proximal end of rod 990 would be threaded at so that rod 990 mates with a threaded inner bore within handle 10. Rotation of an actuator knob would move knob and rod 990 in an axial direction with respect to shaft 11. Movement of rod 990 in an axial direction with respect to shaft 11 would controllably pivot jaw assembly 90 about pivot point 910, thereby allowing a surgeon to remotely control the orientation of jaws 35 and 45 relative to shaft 11 of handle 10. Note that handle 10 may alternatively include another type of actuator mechanism to remotely control linkage 850, for example, a plunger mechanism, a pair of scissor-type handles or a lever mechanism.

In an alternative embodiment of the invention, the ablation device may comprise multiple joints may comprises one or more remotely actuated variable linkages or joints, as described above. Shaft 11 may include, for example, a plurality of remotely actuable variable joints such as elbows, wrists, hinges, linkages and/or ball and sockets, as is well known in the art. These joints may be remotely actuable via cables or rods, for example, extending between the joint and the proximal portion of handle 10 through shaft 11. The distal end of the cables or rods would be connected to the joint. The proximal end of the cables or rods would be connected to an actuator mechanism on handle 10. The actuator mechanism used to remotely control a joint may be, for example, a knob, a lever mechanism, a plunger mechanism, a pair of scissor-type handles, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. The joint may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

Figure 53:
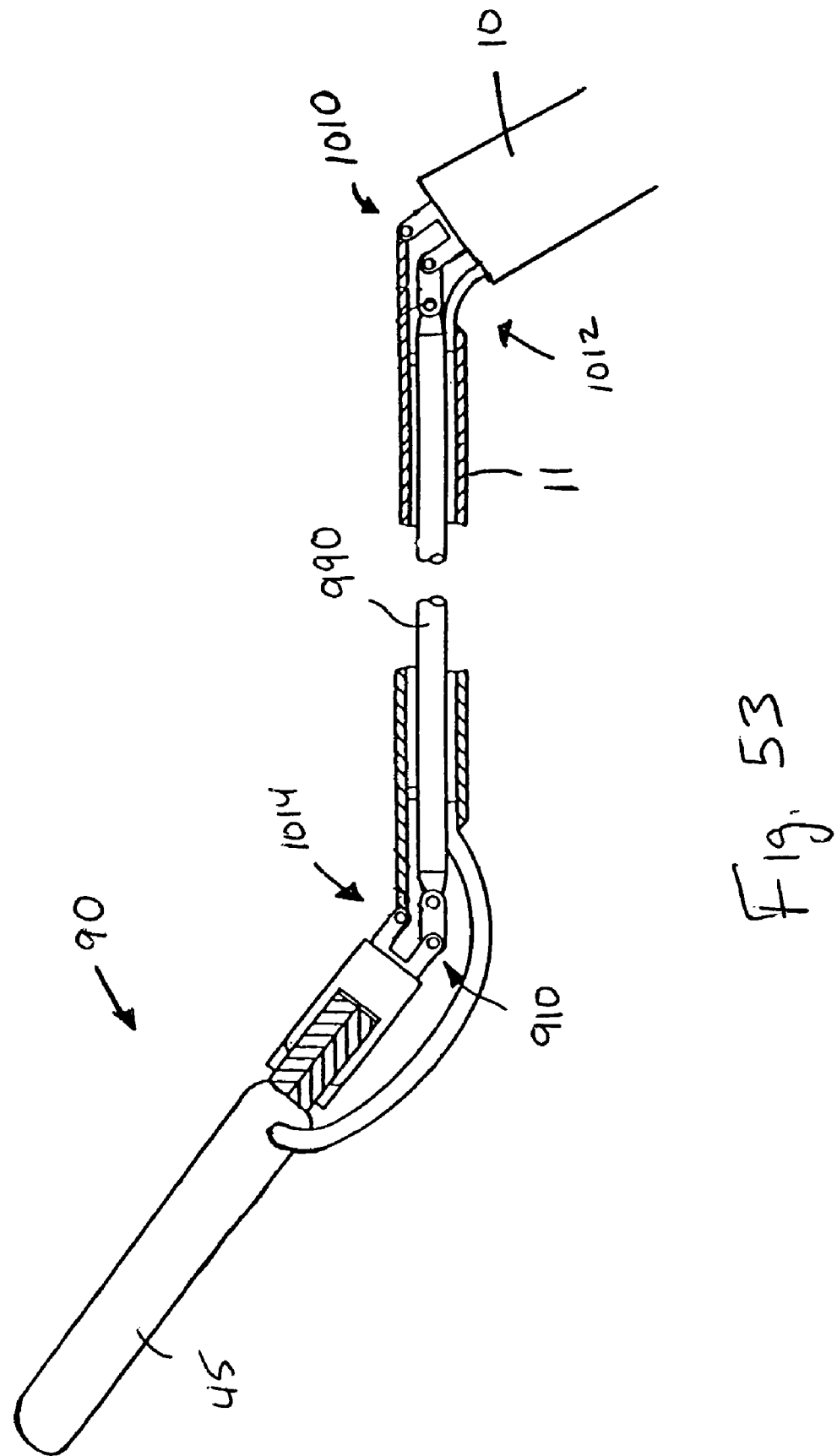
FIG. 53 is a view of a portion of a hemostat according to one embodiment of the present invention.
Figure 54:
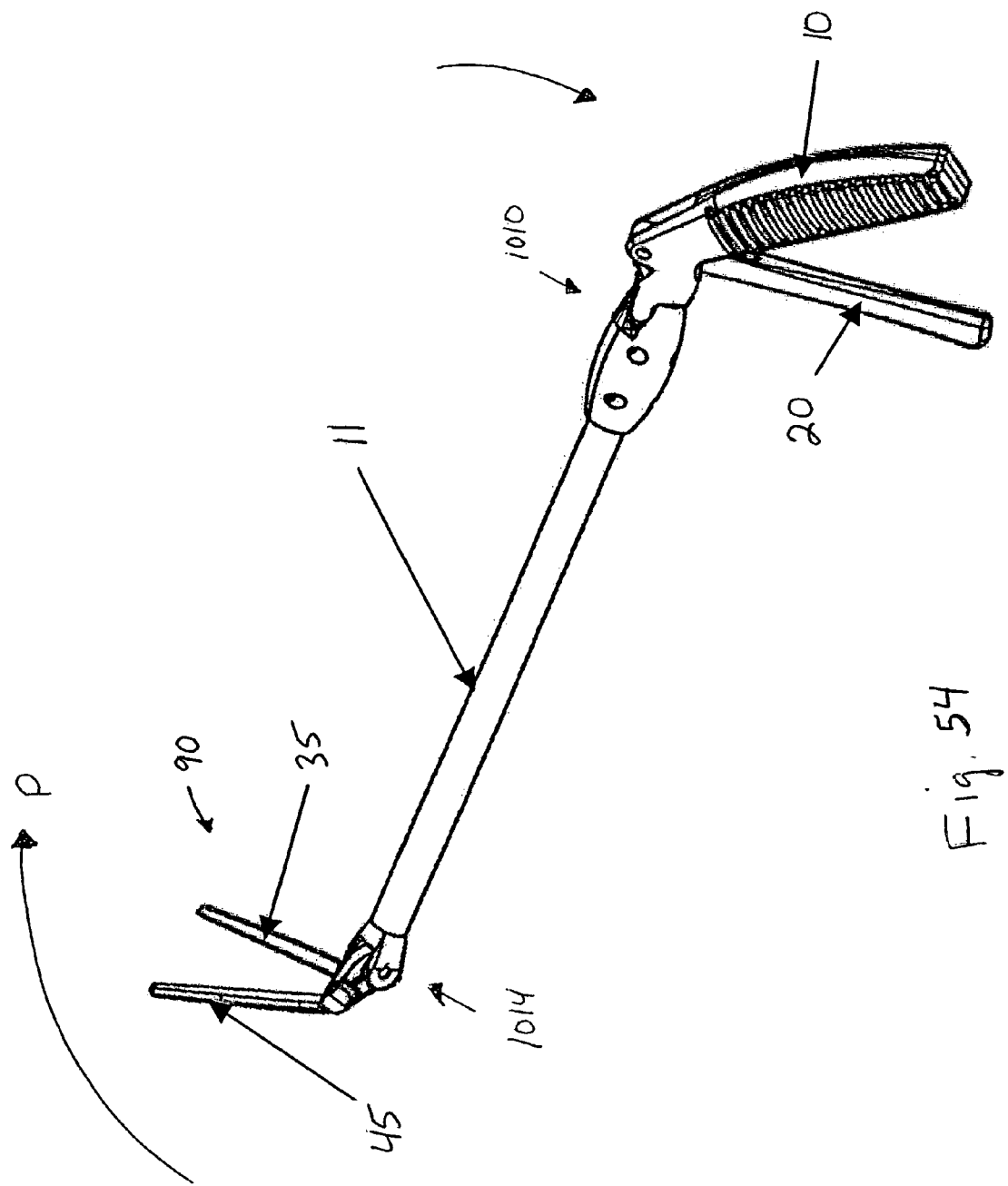
FIG. 54 is a view of a hemostat according to one embodiment of the present invention.
Figure 55:
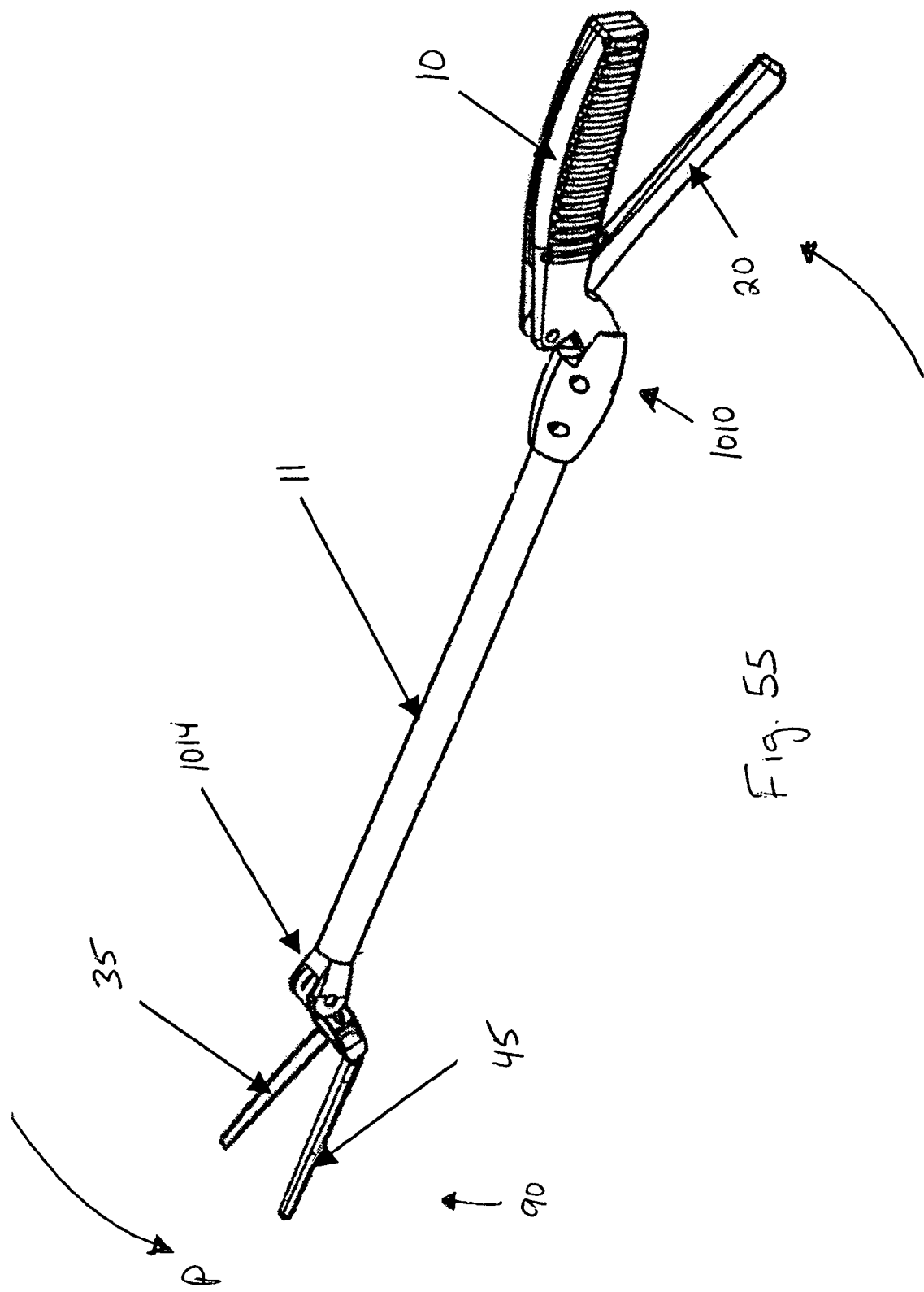
FIG. 55 is a view of a hemostat according to one embodiment of the present invention.

Referring to FIGS. 53, 54 and 55, in an alternative embodiment of the invention, the ablation device may comprise a pair of joints, one located at the distal end of shaft 11 and the other located at the proximal end of shaft 11. The joint 1014 located at the distal end of shaft 11 is coupled to jaw assembly 90 while the joint 1012 coupled at the proximal end is coupled to handle 10. The distal end of cable or rod 990 is coupled to joint 1014 while the proximal end of cable or rod 990 is coupled to joint 1012. Rod 990 is coupled to both joints so that movement of one joint creates movement in the other joint. As shown in FIG. 53, jaw assembly 90 will pivot about a transverse axis through pivot point 910 while handle 10 will pivot about a transverse axis through pivot point 1010. In this embodiment, movement of jaw assembly 90 is remotely controlled or actuated via movement of handle 10. In one embodiment as shown in FIGS. 53, 54 and 55, pivoting of handle 10 in one direction will pivot jaw assembly 90 in the opposite direction. In an alternative embodiment, the two joints may be coupled together so that pivoting of handle 10 in one direction will pivot jaw assembly 90 in the same direction.

Figure 56:
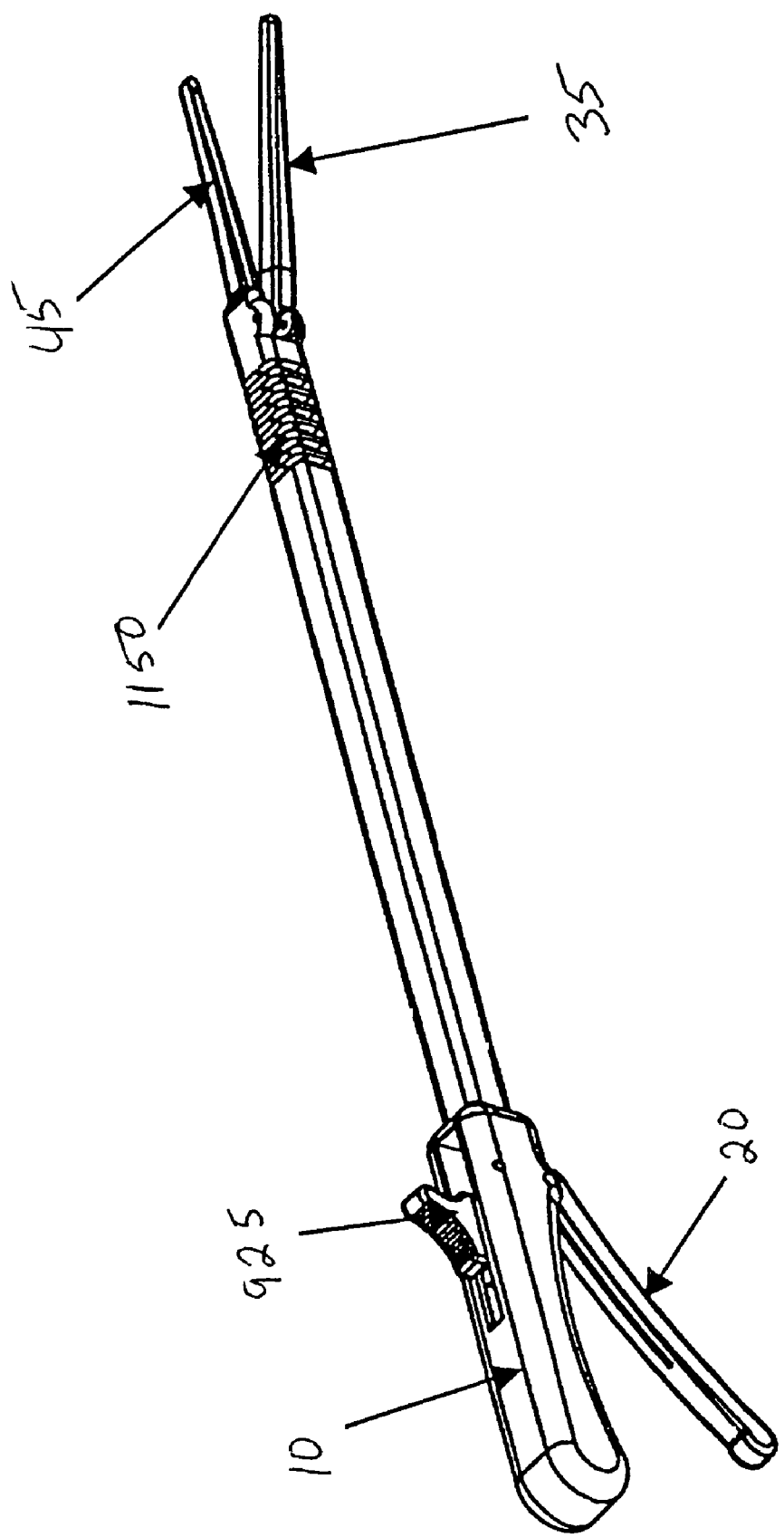
FIG. 56 is a view of a hemostat according to one embodiment of the present invention.

In one embodiment of the invention, shaft 10 may comprise a flexible neck portion 1150 as shown in FIGS. 56, 57 and 58. The device may be used to ablate cardiac tissue using a sub-xiphoid approach. The flexible neck enables the device to be inserted through a small incision while enabling jaw assembly 90 to be orientated in the proper position to ablate cardiac tissue such as tissue around the pulmonary veins. A cable 1152 that is connected to the thumb slide 925 actuates the flexible neck. The cable 1152 runs through the neck off center, as shown in FIG. 58, and is attached at the distal end. Pulling back on the thumb slide 925 angles up the jaws, as shown in FIG. 57, the memory of the material that the flexible neck is made of is what pulls it back to its home position, although some type of spring assist may be used. The handle 10 may be notched in the thumb slide groove to allow the flexible neck to be incrementally locked, for example, at 10-degree increments. The flexible neck has one or more lumens to allow wires, conductors, tubes and/or conduits, for example, to pass through.

Handle 10 may alternatively include another type of actuator mechanism 20 to remotely control the opening and closing of jaws 35 and 45, for example, a knob, a plunger mechanism, a pair of scissor-type handles, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. Jaw assembly 90 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. Jaw assembly 90 may be coupled to gearing, which in turn, is coupled to a motor. The motor is further coupled to a power source. The motor and power source which may be used together are coupled to a controller which detects and controls the opening and closing of jaws 35 and 45. Of course, further designs to control the opening and closing of jaws 35 and 45 may also be used, such as other mechanical or hydraulic activated or controlled systems.

One or more embodiments of the present invention may be used for small incision or port access ablation procedures. For these types of procedures, the size of the distal portion of the device including the jaw assembly and swivel assembly must be sized to fit within the desired port size or incision length. In addition, the length of the handle shaft must be of a sufficient length to reach the desired anatomy. In one embodiment of the present invention, the jaw assembly, swivel assembly, and any joints the device comprises may be manipulated and positioned with the aid of a second endoscopic instrument, such as an endoscopic forceps. Alternatively, the use of "pull wires", "push rods" or other means of integrated steering and/or manipulation may be used to remotely, from outside of the patient's body, manipulate and control various components of the ablation device including the jaw assembly, the swivel assembly and any joints that the device comprises.

In an alternative embodiment, jaw assembly 90 may be designed so that the electrode assemblies of jaws 35 and 45 are replaceable, i.e., the device would be "resposable." For example, the electrode assemblies, i.e., the assembly of the electrode, the porous electrode support and the insulated electrode sheath, may be removable from the backbone or spine of the upper and lower jaws, thereby allowing the electrode assemblies to be replaced between procedures. Alternatively, the entire jaw assembly may be designed to be replaceable. For example, the jaw assemblies including the backbone or spine may be designed to snap into position with upper and lower jaw mounts 300 and 400.

Shaft 11 may be comprised of several elements. For example, it may comprise one or more lumens or a tube having one or more lumens. The lumens may be used to route one or more electrical conductors, fluid lines, drive cables and/or rods. Shaft 11 may be used to direct or steer the jaw assembly 90. Shaft 11 may be of sufficient rigidity to support the weight of jaw assembly 90 while being malleable enough to be shaped for manipulating around a patient's anatomy. Shaft 11 may be comprised of one or metals, such as stainless steel, or other materials such as polymers or composites.

In one embodiment of the invention, a means for controlling the ablation energy, e.g., a switch, may be incorporated into handle 10. Alternatively, a switch remote from the device, e.g. a foot pedal, may be used to control the delivery of ablation energy. In one embodiment, the hand piece has a trigger that closes the electrode jaws. Simultaneous with the actuation of the trigger and closing the jaws, the trigger will activate the ablation energy. Therefore, the ablation energy will only be delivered when the jaws are in a closed configuration. Alternatively, a sensor may used to determine if the jaws are in a closed or open configuration. If the sensor determines the jaws are in an open configuration, ablation energy may be delivered to the electrodes. If the jaws are sensed to be in an open configuration, the delivery of ablation energy to the electrodes is not allowed, will not occur or is stopped from occurring. The delivery of ablation energy may also be, for example, voice-activated comprising voice-recognition technologies. A visual and/or audible signal, such as a flashing light and/or beeping tone, may be incorporated to alert a surgeon to the completion or resumption of the delivery of ablation energy. A delivery of ablation energy to the device may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. In one embodiment of the invention, built into electrical connector 85 may be a small fuse and/or EEPROM that can be used to prevent re-use.

In one embodiment of the invention, a means to control the flow of fluid to the electrodes, e.g., a fluid controller such as a valve, may be incorporated into handle 10. Alternatively, a fluid controller remote from the ablation device may be used. A fluid controller may also be, for example, voice-activated comprising voice-recognition technologies. A visual and/or audible signal, such as a flashing light and/or beeping tone, may be incorporated to alert a surgeon to the completion or resumption of fluid delivery. A fluid controller may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. Fluid, such as saline, may be delivered to the device, for example, from an infusion pump or from a saline bag pressurized with a pressure cuff. In one embodiment, the hand piece has a trigger that closes the electrode jaws. Simultaneous with the actuation of the trigger and closing the jaws, the trigger will activate the fluid delivery. Therefore, fluid will only be delivered when the jaws are in a closed configuration. Alternatively, a sensor may used to determine if the jaws are in a closed or open configuration. If the sensor determines the jaws are in an open configuration, fluid may be delivered to the electrodes. If the jaws are sensed to be in an open configuration, the delivery of fluid to the electrodes is not allowed, will not occur or is stopped from occurring.

The ablation device of the present invention may include additional features, for example, a light means to provide light to where the surgical procedure will be performed, for example, via an optical fiber coupled to a remote light source. The ablation device may feature one or more cutting means or visual means. The ablation device may include one or more sensors. For example, a sensor may be used to determine if the shaft of a device having an articulating shaft is in a locked position. If the sensor determines the articulating shaft is not in a locked position the sensor could prevent the delivery of fluid and/or ablation energy to the electrodes or ablation elements. A sensor could be used to determine if tissue is present between the jaws. If tissue is not present, the sensor could prevent the delivery of fluid and/or ablation energy to the ablation elements. In one embodiment of the invention, the ablation device may include one or more temperature-sensitive elements, such as a thermocouple, to allow a surgeon to monitor temperature changes of a patient's tissue. The ablation device may include one or more sensors for sensing voltage, amperage, wattage and/or impedance. The ablation device may include one or more sensors suitable for sensing blood pressure or flow, for example a Doppler ultrasound sensor system.

The ablation device may include one or more biosensors, for example, comprising an immobilized biocatalyst, enzyme, immunoglobulin, bacterial, mammalian or plant tissue, cell and/or subcellular fraction of a cell. For example, a biosensor may comprise a mitochondrial fraction of a cell, thereby providing the sensor with a specific biocatalytic activity. The ablation device may include one or more sensors based on potentiometric technology or fiber optic technology. For example, a sensor may comprise a potentiometric or fiber optic transducer. An optical sensor may be based on either an absorbance or fluorescence measurement and may include an UV, a visible or an IR light source.

The ablation device may include one or more sensors used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc. The ablation device may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

One or more sensors may be incorporated into the ablation device of the present invention, for example, in or one the handle 10 or the jaw assembly 90. The ablation device may be slaved to one or more sensors. For example, the ablation device may be designed to automatically stop ablation if a sensor measures a predetermined sensor value, e.g., a particular temperature value. In one embodiment of the invention, if a sensor of the present invention indicates that ablated tissue has reached a particular temperature, ablation is stopped automatically, thereby preventing charring of the tissue.

One or more sensors of the present invention may include a visual and/or audible signal used to alert a surgeon to any change in the one or more characteristics the sensor is monitoring. For example, a beeping tone or flashing light that increases in frequency as tissue temperature rises may be used to alert the surgeon.

In one embodiment of the invention, the tissue contacting surfaces of jaws 35 and 45 may be slightly curved such that the surface will conform generally to the curvature of the heart. The heart contacting surfaces of jaws 35 and 45 may comprise one or more conformable materials such as a pliable polymer to facilitate conforming to the shape of the tissue to be ablated. The conformable or pliable material may comprise of one or more materials, for example, polymers, such as silicon, low durometer PVC or polyurethane, which are pliable and biocompatible may be used. In one embodiment of the invention, jaws 35 and 45 may comprise one or more ablating elements used to ablate tissue via RF ablation, cryo ablation, microwave ablation and/or ultrasound ablation.

In one embodiment of the invention, the ablation device is a handheld, single-patient use, bipolar, RF ablation device. The device may be used to ablate soft tissue during general surgery using radiofrequency energy. The device may be a dual linear electrode device that has integral fluid delivery to both electrodes. It may be able to rapidly create linear transmural lesions in both atria of the heart during cardiac surgical procedures. The device may comprise one or more articulating joints to allow a wide range of flexibility and positioning. The electrodes may be malleable to allow contouring of the electrode to match specific physiologies. Therefore, the device may be designed to have a wide range of flexibility to access virtually all lesions required for the currently defined Maze III procedure. The device may be used in stopped-heart and beating-heart procedures. The device may be used in conjunction with a concomitant procedure such as a mitral valve surgery.

The embodiments of the electrosurgical hemostat described above contain a number of valuable features and components, all of which contribute to provide a hemostat, which is convenient to use while providing substantial flexibility in use. However, many of the features of the hemostat could be employed in hemostats of other designs. For example, the trigger mechanism and/or the trigger lock mechanism of the above-described hemostat would certainly be of use in conjunction with cable activated hemostats having jaws of alternative designs to that described above. Similarly, the jaw assembly of the present hemostat might well be employed in conjunction with alternative trigger mechanisms. And/or in conjunction with alternative electrode designs, including electrodes which might not include provision for fluid irrigation and/or in the context of the hemostat having jaws that are rigid and not malleable by the physician to assume desired configurations. Further the specific electrode design employed in the hemostat design described above would be of significant use in conjunction with other hemostat types, including hemostats having jaws which are moved toward one another by alternative mechanisms. Similarly, a strain relief of the type described above including an LED indicator is believed to be of value in conjunction with any number of electrosurgical tools, particularly those in which the strain relief is within the physician's field of view, during normal operation of the hemostat.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A device for performing a surgical procedure, comprising
   a handle comprising a malleable shaft;
   a pair of closeable jaws on a distal portion of the malleable shaft;
   means on at least one of the jaws for ablative treatment of tissue;
   means for closing the jaws on tissue
   means for adjusting roll of the pair of jaws relative to the malleable shaft; and
   means for retaining a selected roll position of the pair of jaws relative to the handle in one of a limited number of selectable predetermined positions such that the jaws can be closed without changing the selected roll position.

2. The device according to claim 1 wherein roll is manually adjustable.

3. The device according to claim 1 wherein each of the jaws are manually shapeable.

4. The device according to claim 1 wherein each of the jaws include at least one malleable component.

5. The device according to claim 1 wherein each of the jaws are rigid.

6. The device according to claim 1 wherein each of the jaws are curved.

7. The device according to claim 1 wherein the means for closing the jaws includes a trigger mounted on the handle.

8. The device according to claim 1 wherein a first, upper jaw of the pair of jaws includes a pivot.

9. The device according to claim 1 wherein the means for closing the jaws includes means for closing a first, upper jaw of the pair of jaws while maintaining the second, lower jaw of the pair of jaws in a stationary position.

10. The device according to claim 9 wherein a trigger is operatively coupled to the upper jaw and not the lower jaw.

11. The device according to claim 1 wherein the means for closing the jaws includes means for closing a first, lower jaw of the pair of jaws while maintaining the second, upper jaw of the pair of jaws in a stationary position.

12. The device according to claim 11 wherein a trigger is operatively coupled to the lower jaw and not the upper jaw.

13. The device according to claim 1 wherein the means for ablative treatment of tissue includes a fluid channel.

14. The device according to claim 1 wherein the means for ablative treatment of tissue includes an electrode.

15. A device for performing a surgical procedure within the body of a patient, comprising a handle including an elongated housing wherein the elongated housing rotates with the handle and not relative to the handle;

a pair of closeable jaws on a distal portion of the handle;

means on at least one of the jaws for ablative treatment of tissue;

means for closing the jaws on tissue;

means for adjusting pitch of the pair of jaws relative to the handle from outside the body of the patient while the jaws are located within the body of the patient; and means for retaining a selected roll position of the pair of jaws relative to the handle in one of a limited number of selectable predetermined positions such that the jaws can be closed without changing the selected roll position.

16. The device according to claim 15 wherein pitch is manually adjustable.

17. The device according to claim 15 also comprising means for retaining a selected pitch position such that the jaws can be closed on tissue without changing the selected pitch position.

18. The device according to claim 15 also comprising means for retaining a selected pitch position such that the jaws can be opened from a closed position without changing the selected pitch position.

19. The device according to claim 15 wherein the jaws may be closed on tissue in a pre-selected curved or straight configuration.

20. The device according to claim 15 wherein each of the jaws are manually shapeable.

21. The device according to claim 15 wherein each of the jaws include at least one malleable component.

22. The device according to claim 15 wherein each of the jaws are rigid.

23. The device according to claim 15 wherein each of the jaws are curved.

24. The device according to claim 15 wherein the means for closing the jaws includes a trigger mounted on the handle.

25. The device according to claim 15 wherein a first, upper jaw of the pair of jaws includes a pivot.

26. The device according to claim 15 wherein the means for closing the jaws includes means for closing a first, upper jaw of the pair of jaws while maintaining the second, lower jaw of the pair of jaws in a stationary position.

27. The device according to claim 26 wherein a trigger is operatively coupled to the upper jaw and not the lower jaw.

28. The device according to claim 15 wherein the means for closing the jaws includes means for closing a first, lower jaw of the pair of jaws while maintaining the second, upper jaw of the pair of jaws in a stationary position.

29. The device according to claim 28 wherein a trigger is operatively coupled to the lower jaw and not the upper jaw.

30. The device according to claim 15 wherein the means for ablative treatment of tissue includes a fluid channel.

31. The device according to claim 15 wherein the means for ablative treatment of tissue includes an electrode.

32. The device according to claim 15 wherein the handle includes at least one malleable component.

33. A method for performing a surgical procedure, comprising:

providing a device having an elongated shapeable handle and a pair of jaws on a distal portion of the handle;

shaping the handle into a selected configuration;

adjusting roll of the pair of jaws to a selected roll position relative to the elongated shapeable handle;

retaining the selected roll position in one of a limited number of selectable predetermined positions relative to the handle such that the jaws can be closed without changing the selected roll position;

introducing the distal portion of the device into a surgical incision;

placing a portion of tissue between the pair of open jaws;

closing the jaws into contact with the portion of tissue;

performing an ablative treatment on the portion of tissue; and opening the jaws.

34. The method according to claim 33 wherein adjusting roll of the pair of jaws is performed manually.

35. The method according to claim 33 wherein shaping the handle is performed manually.

36. The method according to claim 33 wherein closing the jaws includes closing a first, upper jaw of the pair of jaws while maintaining the second, lower jaw of the pair of jaws in a stationary position.

37. The method according to claim 36 wherein the first jaw is substantially parallel to the second jaw in an open configuration and a closed configuration.

38. The method according to claim 33 wherein closing the jaws includes closing a first, lower jaw of the pair of jaws while maintaining the second, upper jaw of the pair of jaws in a stationary position.

39. The method according to claim 38 wherein the first jaw is substantially parallel to the second jaw in an open configuration and a closed configuration.

40. The method according to claim 38 wherein first and second jaws of the pair of jaws are substantially parallel to each other when the jaws are open and when the jaws are closed.

41. The method according to claim 33 wherein shaping the handle is performed remotely.

42. The method according to claim 33 wherein at least a portion of the handle is malleable.

* * * * *